(12) United States Patent
Chang et al.

(10) Patent No.: US 9,546,367 B2
(45) Date of Patent: Jan. 17, 2017

(54) SIRNA COMPOSITIONS AND METHODS FOR INHIBITING GENE EXPRESSION IN TUMOR INITIATING CELLS OF BREAST CANCER

(71) Applicants: Jenny Chee Ning Chang, Houston, TX (US); Bhuvanesh Dave, Pearland, TX (US)

(72) Inventors: Jenny Chee Ning Chang, Houston, TX (US); Bhuvanesh Dave, Pearland, TX (US)

( * ) Notice: Subject to any disclaimer, the term of this patent is extended or adjusted under 35 U.S.C. 154(b) by 0 days.

(21) Appl. No.: 14/363,545

(22) PCT Filed: Dec. 7, 2012

(86) PCT No.: PCT/US2012/068596
§ 371 (c)(1),
(2) Date: Jun. 6, 2014

(87) PCT Pub. No.: WO2013/086433
PCT Pub. Date: Jun. 13, 2013

(65) Prior Publication Data
US 2015/0037401 A1    Feb. 5, 2015

Related U.S. Application Data

(60) Provisional application No. 61/567,917, filed on Dec. 7, 2011.

(51) Int. Cl.
*C07H 21/02* (2006.01)
*C12N 15/11* (2006.01)
*C12N 15/113* (2010.01)
*A61K 31/337* (2006.01)
*A61K 31/713* (2006.01)

(52) U.S. Cl.
CPC .......... *C12N 15/1135* (2013.01); *A61K 31/337* (2013.01); *A61K 31/713* (2013.01); *C12N 15/113* (2013.01); *C12N 2310/11* (2013.01); *C12N 2310/14* (2013.01); *C12N 2310/531* (2013.01)

(58) Field of Classification Search
None
See application file for complete search history.

(56) References Cited

U.S. PATENT DOCUMENTS

2005/0255487 A1* 11/2005 Khvorova ............ A61K 31/713 435/6.11
2008/0113351 A1* 5/2008 Naito .................. A61K 31/713 435/6.11

OTHER PUBLICATIONS

Piggott et al (Breast Cancer Res. 13:R88, 15 pages 2011).*
GenBank Accession NM_014983.1, 2009.*

* cited by examiner

*Primary Examiner* — Richard Schnizer
(74) *Attorney, Agent, or Firm* — Buche & Associates, P.C.; John K. Buche; Bryce A. Johnson

(57) ABSTRACT

Disclosed are methods and compositions for siRNA-mediated therapy of mammalian diseases. In particular, compositions and methods are disclosed for treatment of therapy-resistant human breast cancers. In exemplary embodiments, siRNA molecules are presented that effectively knock down gene expression of one or more polynucleotides in breast cancer tumor initiating cells.

10 Claims, 28 Drawing Sheets

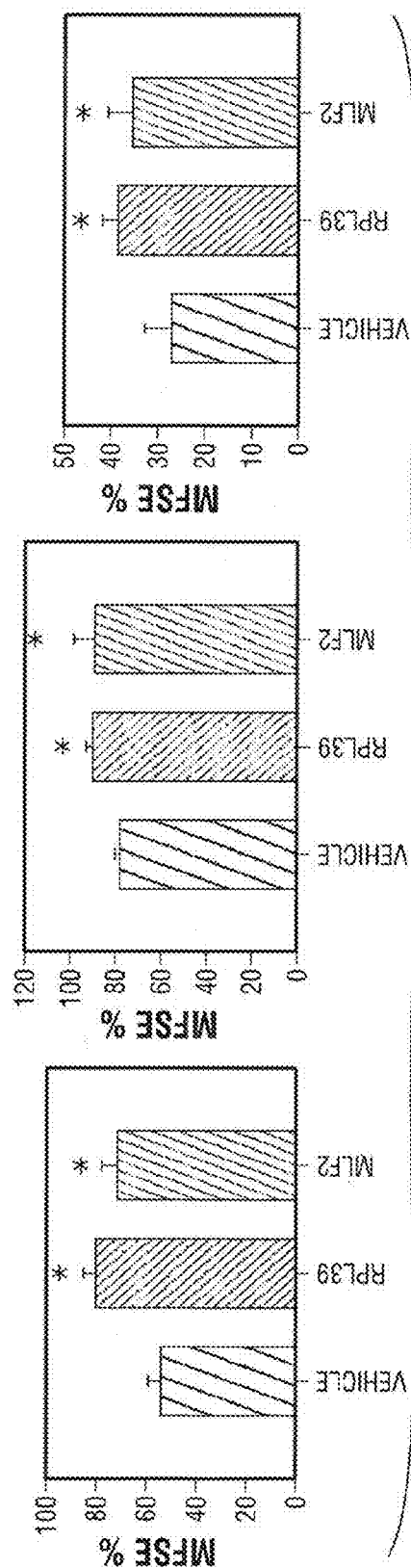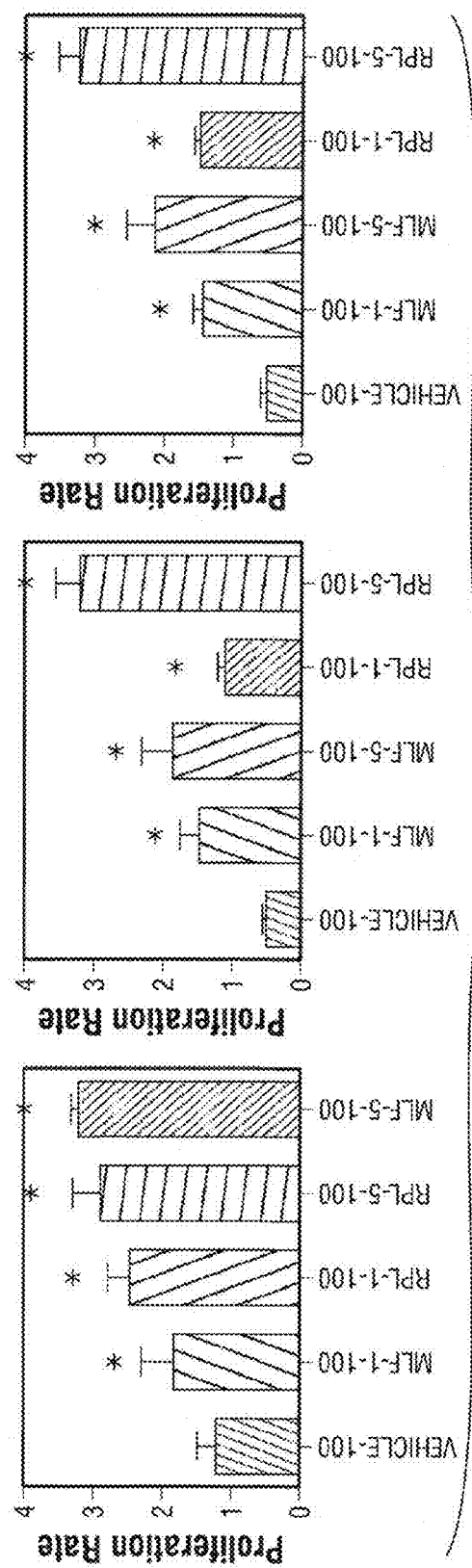
FIG. 11B
FIG. 11C

SEQUENCE LISTING

```
<160> NUMBER OF SEQ ID NOS: 32

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
atctcgcttg ggcgagagta ag                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 2
ccaagttcat ggccttaggt ag                                              22

<210> SEQ ID NO 3
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 3
ccctgatgga tcccttttgct at                                              22

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 4
cccttctgag gtctacctga aa                                               22

<210> SEQ ID NO 5
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 5
accttctttg ctggctttat ta                                               22

<210> SEQ ID NO 6
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 6
cgcctgtatt tggaagattt aa                                               22

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 7
cggctgagaa gtttcagata tt                                               22

<210> SEQ ID NO 8
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 8
cgctaagtgt cttggtattt aa                                               22

<210> SEQ ID NO 9
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 9
cgctcagtac ctgaaaggaa ta                                               22
```

```
<210> SEQ ID NO 10
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 10
acccttcagt ctccacttca tt                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 11
atcttacata atgtatttat aa                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 12
atgctactat ccgttattta at                                              22

<210> SEQ ID NO 13
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 13
aaccctgagt tgtgaacaga at                                              22

<210> SEQ ID NO 14
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 14
acggcgtcca gttcactact aa                                              22

<210> SEQ ID NO 15
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 15
acgattcctg gccaagaaac aa                                              22

<210> SEQ ID NO 16
<211> LENGTH: 19
<212> TYPE: DNA
<213> ORGANISM: Artificial Sequence
<220> FEATURE:
<223> OTHER INFORMATION: Synthetic Oligonucleotide
```

```
<400> SEQUENCE: 16
gcctgtctat gtggtagat                                              19

<210> SEQ ID NO 17
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 17
cttactctcg cccaagcgag ag                                          22

<210> SEQ ID NO 18
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 18
ctacctaagg ccatgaactt ga                                          22

<210> SEQ ID NO 19
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 19
atagcaaagg gatccatcag ga                                          22

<210> SEQ ID NO 20
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 20
tttcaggtag acctcagaag ga                                          22

<210> SEQ ID NO 21
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 21
taataaagcc agcaaagaag gg                                          22

<210> SEQ ID NO 22
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 22
ttaaatcttc caaatacagg ca                                          22
```

```
<210> SEQ ID NO 23
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 23
aatatctgaa acttctcagc ct                                              22

<210> SEQ ID NO 24
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 24
ttaaatacca agacacttag ct                                              22

<210> SEQ ID NO 25
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 25
tattcctttc aggtactgag ca                                              22

<210> SEQ ID NO 26
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 26
aatgaagtgg agactgaagg gc                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 27
ttataaatac attatgtaag ag                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 28
attaaataac ggatagtagc ag                                              22

<210> SEQ ID NO 29
<211> LENGTH: 22
<212> TYPE: DNA
<213> ORGANISM: Artificial Sequence
<220> FEATURE:
<223> OTHER INFORMATION: Synthetic Oligonucleotide
```

```
<400> SEQUENCE: 29
attctgttca caactcaggg tc                                            22

<210> SEQ ID NO 30
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 30
ttagtagtga actggacgcc gg                                            22

<210> SEQ ID NO 31
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 31
ttgtttcttg gccaggaatc gc                                            22

<210> SEQ ID NO 32
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 32
atctaccaca tagacaggc                                                19
```

SIRNA COMPOSITIONS AND METHODS FOR INHIBITING GENE EXPRESSION IN TUMOR INITIATING CELLS OF BREAST CANCER

CROSS-REFERENCE TO RELATED APPLICATIONS

The present application claims priority to U.S. Provisional Patent Application 61/567,917, filed Dec. 7, 2011. the entire contents of which is specifically incorporated herein by reference in its entirety.

STATEMENT REGARDING FEDERALLY SPONSORED RESEARCH OR DEVELOPMENT

This invention was made with government support under Grant Nos. ROI-CA112305, and ROI CA138197 awarded by the National Institutes of Health, and Grant No. W81XWH-04-1-0468 awarded by the United States Army Medical Research and Materiel Command. The government has certain rights in the invention.

NAMES OF THE PARTIES TO A JOINT RESEARCH AGREEMENT

Not Applicable.

BACKGROUND OF THE INVENTION

1. Field of the Invention

The present invention relates generally to the fields of biochemistry and medicine. In particular, the invention provides methods and compositions for treatment of therapy-resistant human breast cancer, and in particular, provides siRNA compositions that inhibit gene expression in tumor initiating cells of human breast cancer.

2. Description of Related Art

There were approximately 180,000 new cases of breast cancer diagnosed in the United States in 2007. About 15% of these, accounting for 25,000 to 30,000 cases each year, are "triple-negative breast cancer" (TNBC) in that the tumors do not express the estrogen receptor (ER), progesterone receptor (PR), or HER-2/neu (DeSantis et al., 2010). Unlike therapies targeted against steroid hormone receptors or HER2, there is no Food and Drug Administration (FDA) approved targeted drugs for the treatment of TNBC, and hence these cancers are associated with the worst prognosis. The identification of new therapeutic targets against TNBC is crucial to improving the outcome of this subtype. Use of liposome-mediated nanoparticles in order to mediate siRNA/shRNA therapy is a new approach for targeting novel non-druggable targets for which traditional therapies do not exist.

Developing therapies that are capable of attacking and destroying the "lethal seeds" driving these cancers, the "tumor initiating cells" (TICs)", represent a significant advancement over conventional therapies.

BRIEF SUMMARY OF THE INVENTION

The present invention overcomes these and other limitations inherent in the prior art by providing an inventive therapeutic siRNA molecules for the treatment of mammalian cancers, and human breast cancer in particular.

In a first embodiment, the invention provides small interfering RNA molecules that include (a) a first duplex region; and (b) either no overhang region or at least one overhang region, wherein each overhang region has six or fewer nucleotides (preferably five or fewer, more preferably, four or fewer, even more preferably, three or fewer, or even more preferably still, two or fewer), wherein the duplex region consists of a first sense region and a first antisense region that together form the duplex region, and further wherein the first antisense region and the first sense region are each from abort 19 to about 30 nucleotides in length (preferably about 20, about 21, about 22, about 23, about 24, about 25, about 26, about 27, about 28, about 29, or about 30), and the antisense region comprises (or alternatively, consists essentially of, or consists of) a nucleotide sequence that is substantially complementary (preferably at least about 95% or greater complementary, more preferably at least about 96% or greater complementary, at least about 97% complementary, at least about 98% complementary, or at least about 99% or greater complementary) to the sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8. SEQ ID NO:9, SEQ ID NO:10. SEQ ID NO:11, SEQ ID NO:12. SEQ ID NO:13, SEQ ID NO:14, SEQ ID NO:15, SEQ ID NO:16, SEQ ID NO:17. SEQ ID NO:18. SEQ ID NO:19, SEQ ID NO:20, SEQ ID NO:21, SEQ ID NO:22, SEQ ID NO:23, SEQ ID NO:24, SEQ ID NO:25, SEQ ID NO:26. SEQ ID NO:27, SEQ ID NO:28, SEQ ID NO:29, SEQ ID NO:30, SEQ ID NO:31 and SEQ ID NO:32 (see e.g., Table 1).

Preferably, such small interfering RNA molecules are shRNA or siRNAs, and preferably, the antisense region and the sense region are each about 21 to about 30 (alternatively, about 20 to about 29 nucleotides in length, about 22 to about 28, or any intermediate range, or any individual integer therein) nucleotides in length.

Preferably, the small interfering RNA molecules of the present invention comprises, consists essentially of, or alternatively, consists of, at least one overhang region, and the antisense region preferably comprises, consists essentially of, or alternatively consists of, a nucleotide sequence that is about 100% complementary to the sequence of any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14. SEQ ID NO:15, SEQ ID NO:16. SEQ ID NO:17, SEQ ID NO:18, SEQ ID NO:19. SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32 (see e.g. Table 1).

In illustrative embodiments, the inventors have prepared small interfering RNA molecules that include: (a) a first duplex region; and (b) either no overhang region or at least one overhang region, wherein 1) each overhang region has six or fewer nucleotides; 2) the duplex region consists of a sense region and an antisense region that together form the duplex region, 3) the antisense region and the sense region are each 19 to about 30 nucleotides in length; and 4) the antisense region comprises a nucleic acid sequence that is at least substantially complementary to the nucleotide sequence of any one of SEQ ID NO:1. SEQ ID NO:2, SEQ ID NO:3, SEQ ID NO:4, SEQ ID NO:5, SEQ ID NO:6. SEQ ID NO:7, SEQ ID NO:8, SEQ ID NO:9, SEQ ID NO:10, SEQ ID NO:11, SEQ ID NO:12. SEQ ID NO:13, SEQ ID NO:14, SEQ ID NO:15, SEQ ID NO:16, SEQ ID NO:17. SEQ ID NO:18, SEQ ID NO:19, SEQ ID NO:20. SEQ ID NO:21, SEQ ID NO:22, SEQ ID NO:23, SEQ ID NO:24, SEQ ID NO:25, SEQ ID NO:26, SEQ ID NO:27. SEQ ID NO:28, SEQ ID NO:29. SEQ ID NO:30, SEQ ID NO:31 and SEQ ID NO:32.

In exemplary embodiments, the small interfering RNA molecules of the present invention include an antisense region that comprises, consists essentially of, or alternatively consists of, a nucleotide sequence that is 100% complementary to the sequence of any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15. SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32.

In another embodiment, the invention provides a chemically-synthesized, double-stranded siRNA molecule, wherein: (a) each strand of the siRNA molecule is between 19 and about 30 nucleotides in length; and (b) one strand of the siRNA molecule comprises a sequence that is substantially complementary to the sequence of any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32. In exemplary embodiments, the chemically-synthesized, double-stranded siRNA molecule includes one strand that consists of an isolated nucleotide sequence that is 100% complementary to the nucleic acid sequence disclosed in any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25. SEQ ID NO:26, SEQ ID NO:27, SEQ ID NO:28, SEQ ID NO:29, SEQ ID NO:30, SEQ ID NO:31 and SEQ ID NO:32.

In a further embodiment, the invention provides a population of two or more siRNA molecules, wherein the population includes at least a first siRNA molecule that one strand of which comprises a sequence that is substantially complementary to the sequence of any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32, and at least a second, distinct siRNA molecule, whose one strand of which comprises a sequence that is substantially complementary to at least a second, distinct sequence from any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:2, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32. Such populations of mixed siRNA molecules are particularly contemplated to be useful in "multicomponent" therapy wherein two or more genes of interest (including, for examples, those identified herein) are simultaneously targeted by two or more distinct siRNAs.

The invention also provides a method for targeting gene expression in a therapy-resistant human breast cancer tumor-initiating cell (TIC). In an overall and general sense, the method generally includes at least the step of introducing a therapeutically-effective amount of a small interfering RNA in accordance with the present invention into a population of mammalian (and preferably human) cells in need thereof, wherein the antisense sequence of the small interfering RNA consists of a nucleotide sequence in accordance with any one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20. SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32, or a complement thereof, and further wherein the small interfering RNA selectively binds to at least a first polynucleotide that is present in, and preferably expressed by, the cell. In exemplary embodiments, such an antisense sequence is preferably selected from one or more of the sequences as set forth in any one or more of SEQ ID NO:1, SEQ ID NO:2. SEQ ID NO:3, SEQ ID NO:4, SEQ ID NO:5, SEQ ID NO:6, SEQ ID NO:7, SEQ ID NO:8. SEQ ID NO:9, SEQ ID NO:10, SEQ ID NO:11, SEQ ID NO:12, SEQ ID NO:13, SEQ ID NO:14, SEQ ID NO:15, and SEQ ID NO:16.

The inventors have demonstrated that the disclosed methods involve the silencing, "knock-down," and/or reduction in expression of one or more specific genes (e.g. a "gene of interest" or a "targeted gene" or a "selected gene", etc.). In gene "silencing," expression of the gene product is reduced, minimized, lowered, or eliminated, in comparison to a corresponding control gene that is not being silenced. One of ordinary skill in the art is familiar with the concept of comparing results obtained with control vs. experimental results, and such studies need not be detailed further herein. Without being bound by theory, the inventors contemplate that the RNAi is characterized by specific mRNA degradation after the introduction of homologous double stranded RNA (dsRNA) into cells. This dsRNA is then recognized and processed into small interfering RNAs (siRNAs) of 19-25 nucleotides in length by an endonuclease enzyme dimer termed "Dicer" (RNase III family). These siRNAs, in turn, target homologous RNA for degradation by recruiting the protein complex, RNA-induced silencing complex (RISC). The complex recognizes and cleaves the corresponding mRNA (see, e.g., Dykxhoom et al. 2003).

Thus, the invention also provides an interfering RNA molecule that includes at least a first nucleotide sequence that encodes at least one short hairpin RNA(shRNA) or one small interfering (siRNA) molecule that can alter, inhibit, prevent, delay, knock-down, or substantially inhibit the expression of at least one mammalian gene, and preferably one or more such mammalian genes, including those that are expressed in one or more mammalian tumor initiating cells (such as human breast cancer tumor initiating cells), when the molecule is contacted with a population of such cells that express at least one such target gene of interest.

The invention also provides a method for treating, reducing, alleviating, and/or ameliorating one or more symptom of a cancer in a mammal, and of breast cancer in a human in particular. This method generally involves at least the step of providing to a mammal in need thereof, an amount of a composition that comprises, consists essentially of, or alternatively, consists of, a therapeutically-effective amount of a small interfering RNA (preferably a shRNA or a siRNA), wherein the antisense sequence of the small interfering RNA comprises, consists essentially of, or alternatively consists of, a nucleotide sequence in accordance with any one of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32, or any complement thereof, and further wherein the small interfering RNA inhibits breast cancer, or the expression of at least a first gene in a tumor-initiating cell in the mammal, for a time effective to treat, reduce, alleviate, and/or ameliorate one or more symptoms of the cancer in the mammal. Preferably, the small interfering RNA is an shRNA or an siRNA in which the antisense sequence is selected from one or more sequences set forth in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31 and SEQ ID NO:32, and preferably from one or more sequences set forth in one or more of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, and SEQ ID NO:16. Preferably, the cancer is human breast cancer, and in particular therapy-resistant human breast cancer.

In a further embodiment, the invention also provides compositions and pharmaceutical formulations that include one or more of the disclosed siRNA molecules, and a pharmaceutically-acceptable excipient, carrier, buffer, or diluent. In another embodiment, the invention also provides a therapeutic kit that includes one or more of the disclosed siRNA molecules, one or more pharmaceutical excipients, diluents, vehicles or buffers, and a set of instructions for using the siRNA molecules, alone, or in combination with one or more additional chemotherapeutic agents, for treating a mammalian breast cancer, such as therapy-resistant human breast cancer.

To that end, the invention also provides a method for treating, reducing, alleviating, and/or ameliorating one or more symptoms of a therapy-resistant breast cancer in a human. Such a method generally involves, in an overall and general sense, at least the step of providing to a human in need thereof, a therapeutically-effective amount of one or more of the siRNA compositions disclosed herein.

Preparation of Medicaments

Another important aspect of the present invention concerns methods for using the disclosed multistage vectors (as well as compositions or formulations including them) in the preparation of medicaments for treating or ameliorating the symptoms of one or more diseases, dysfunctions, or deficiencies in an animal, such as a vertebrate mammal. Use of the disclosed nanoparticle gold-in-silicon compositions is also contemplated in therapy and/or treatment of one or more diseases, disorders, dysfunctions, conditions, disabilities, deformities, or deficiencies, and any symptoms thereof.

Such use generally involves administration to an animal in need thereof one or more of the disclosed compositions, either alone, or further in combination with one or more additional therapeutic agents, in an amount and for a time sufficient to treat, lessen, or ameliorate one or more of a disease, disorder, dysfunction, condition, disability, deformity, or deficiency in the affected animal, or one or more symptoms thereof, including, without limitation one or more tumors, such as those of the mammalian breast.

Compositions including one or more of the disclosed pharmaceutical formulations also form part of the present invention. Particularly included are those compositions that further include at least a first pharmaceutically acceptable excipient, suitable for administration to a mammal, and particularly, suitable for use in the therapy and/or imaging of one or more diseases, dysfunctions, disorders, or such like, including, without limitation, one or more cancers or tumors of the human body.

Use of the disclosed compositions is also contemplated, particularly in the manufacture of medicaments and methods involving one or more therapeutic (including chemotherapy, phototherapy, laser therapy, etc.) prophylactic (including e.g. vaccines), or diagnostic regimens, (including, without limitation, in diagnostic imaging, such as CT, MRI, PET, ultrasonography, or the like).

The use of such a small interfering RNA molecule to treat cancer or to ameliorate at least one symptom thereof in a human, and the use of such compositions in the manufacture of medicaments for treating breast cancers (including, for example, therapy-resistant human breast cancers), or ameliorating one or more symptoms thereof are also important aspects of the invention.

The pharmaceutical formulations of the present invention may optionally further include one or more additional distinct active ingredients, detection reagents, vehicles, additives, adjuvants, therapeutic agents, radionuclides, gases, or fluorescent labels as may be suitable for administration to an animal. Such routes of administration are known to and may be selected by those of ordinary skill in the art, and include, without limitation, delivery devices including intramuscular, intravenous, intra-arterial, intrathecal, intracavitary, intraventricular, subcutaneous, or direct injection into an organ, tissue site, or population of cells in the recipient animal.

The use of one or more of the disclosed compositions in the manufacture of a medicament for therapy of one or more mammalian cancer is also an important aspect of the invention. Formulation of such compositions for use in administration to an animal host cell, and to a mammalian host cell in particular, is also provided by the invention. In certain embodiments, the invention also provides formulations of the disclosed siRNA compositions for use in the administration to a human, or to one or more selected human host cells, tissues, organs in situ, or to an in vitro or ex situ culture thereof.

The present invention also provides for the use of one or more of the disclosed siRNA compositions in the manufacture of a medicament for the treatment of one or more mammalian cancers, including the preparation of one or more therapeutic regimens for the treatment or ameliorate of one or more symptoms of mammalian tumors such as triple-negative human breast tumors.

The pharmaceutical compositions of the present invention may be administered to a selected animal using any of a number of conventional methodologies, including, without limitation, one or more of parenteral, intravenous, intraperitoneal, subcutaneous, transcutaneous, intradermal, subdermal, transdermal, intramuscular, topical, intranasal, or other suitable route, including, but not limited to, administration, by injection, insertion, inhalation, insufflation, or ingestion.

Yet another advantage of the present invention may include active ingredient(s) and pharmaceutical formulations and compositions that include one or more of such active ingredients useful in treating or ameliorating one or more symptom(s) of an infection, disease, disorder, dysfunction, trauma, or abnormality in a mammal. Such methods generally involve administration to a mammal, and in particular, to a human, in need thereof, one or more of the pharmaceutical compositions, in an amount and for a time sufficient to treat, ameliorate, or lessen the severity, duration, or extent of, such a disease, infection, disorder, dysfunction, trauma, or abnormality in such a mammal.

As described herein, the disclosed pharmaceutical compositions may also be formulated for diagnostic and/or therapeutic uses, including their incorporation into one or more diagnostic or therapeutic kits packaged for clinical, diagnostic, and/or commercial resale. The compositions disclosed herein may further optionally include one or more detection reagents, one or more additional diagnostic reagents, one or more control reagents, one or more targeting reagents, ligands, binding domains, or such like, and/or one or more therapeutic or imaging compounds, including, without limitation, radionucleotides, fluorescent moieties, and such like, or any combination thereof. In the case of diagnostic reagents, the compositions may further optionally include one or more detectable labels that may be used in both in vitro and/or in vivo diagnostic, therapeutic, and/or prophylactic modalities.

Pharmaceutical Compositions

The siRNA molecules of the present invention are preferably formulated into one or more pharmaceutical compositions suitable for administration to an animal, and to a mammal such as a human in particular. Such compositions can be a suspension that includes one or more of the siRNA molecules described herein, and may find particular utility in delivering or facilitating administration of one or more such therapeutic compounds to one or more biological cells, tissues, organs, or one or more regions of interest within, or about, the body of an animal.

Preferably, the compounds of the present invention will generally be formulated for systemic and/or localized administration to an animal, or to one or more cells or tissues thereof, and in particular, will be formulated for systemic and/or localized administration to a mammal, or to one or more cells or tissues thereof. In certain embodiments, the compounds and methods disclosed herein will find particular use in the therapy of cancerous cells or tissues, such as a tumor, within or about the body of a mammal, and preferably, in the treatment of breast cancer in a human being.

The present invention also provides for the use of one or more of the disclosed pharmaceutical compositions in the manufacture of a medicament for therapy, and particularly for use in the manufacture of a medicament for treating, and/or ameliorating one or more symptoms of a disease, dysfunction, or disorder in a mammal, and particularly for the treatment and/or amelioration of one or more symptoms of in human breast cancer in particular.

The present invention also provides for the use of one or more of the disclosed pharmaceutical compositions in the manufacture of a medicament for therapy or amelioration of symptoms of one or more cancers, including, human breast cancers, and therapy-resistant human breast cancers in particular, either alone, or in combination with one or more additional therapeutic and/or diagnostic agents.

In certain embodiments, the present invention concerns formulation of one or more therapeutic siRNA compounds in a pharmaceutically acceptable composition for administration to a cell or an animal, either alone, or in combination with one or more other modalities of prophylaxis and/or therapy. The formulation of pharmaceutically acceptable excipients and carrier solutions is well known to those of ordinary skill in the art, as is the development of suitable dosing and treatment regimens for using the particular compositions described herein in a variety of treatment regimens.

In certain circumstances it will be desirable to deliver the therapeutic siRNA compositions disclosed herein in suitably-formulated pharmaceutical vehicles by one or more standard delivery devices, including, without limitation, subcutaneously, intraocularly, intravitreally, parenterally, intravenously, intracerebroventricularly, intramuscularly, intrathecally, orally, intraperitoneally, transdermally, topically, by oral or nasal inhalation, or by direct injection to one or more cells, tissues, or organs. The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

For administration of an injectable aqueous solution, without limitation, the solution may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, a sterile aqueous medium that can be employed will be known to those of ordinary skill in the art in light of the present disclosure. For example, one dosage may be dissolved in 1 mL of isotonic NaCl solution, and either added to 1000 mL of hypodermoclysis fluid or injected at the proposed site of infusion, (see, e.g., "Remington's Pharmaceutical Sciences" 15th Edition, pages 1035-1038 and 1570-1580). Some variation in dosage will necessarily occur depending on the condition of the subject being treated. The person responsible for administration will determine, in any event, the appropriate dose for the individual subject. Moreover, for human administration, preparations should meet sterility, pyrogenicity, and the general safety and purity standards as required by FDA Office of Biologics standards.

Sterile injectable compositions including one or more of the siRNA molecules disclosed herein may be prepared by incorporating the disclosed molecules in the required amount of an appropriate solvent, followed by filtered sterilization. Generally, dispersions of such compounds can be prepared by incorporating the selected sterilized active ingredient(s) into a sterile vehicle that contains the basic dispersion medium and the required active ingredients from those enumerated above. The siRNA compositions disclosed herein may also be formulated in a neutral or salt form, with pharmaceutically-acceptable salts including, without limitation, acid addition salts, salts formed from an inorganic acid (including, without limitation, hydrochloric or phosphoric acids) or an organic acid (such as, without limitation, acetic, oxalic, tartaric, or mandelic acids, and/or the like). Salts formed with the free carboxyl groups can also be derived from inorganic bases such as, without limitation, sodium, potassium, ammonium, calcium, or ferric hydroxides, and such organic bases as isopropylamine, trimethylamine, histidine, procaine, and the like. Upon formulation, such solutions may be administered to the recipient animal in a manner compatible with the dosage formulation, and in such amount as is effective for the intended application. The siRNA compositions and formulations thereof as described herein may be readily administered in a variety of dosage forms such as injectable solutions, and the like.

The amount, dosage regimen, formulation, and administration of the compositions disclosed herein will be within the purview of the ordinary-skilled artisan having benefit of the present teaching. It is likely, however, that the administration of a therapeutically-effective amount of the disclosed siRNA compositions may be achieved by a single administration, such as, without limitation, a single injection of a sufficient quantity of the delivered siRNA to provide the desired benefit to the patient undergoing such a procedure. Alternatively, in some circumstances, it may be desirable to provide multiple, or successive administrations of the disclosed anti-cancer compositions, either over a relatively short, or even a relatively prolonged period of time, as may be determined by the medical practitioner overseeing the administration of such compositions to the selected individual.

Typically, formulations of one or more siRNA therapeutic agents disclosed herein will contain an effective amount of the therapeutic suitable for administration to the selected recipient animal. Preferably, such formulations will contain at least about 0.001% of each active ingredient, and preferably at least about 0.01% of the active ingredient, although the percentage of the active ingredient(s) may, of course, be varied, and may conveniently be present in amounts from about 0.01 to about 90 weight % or volume %, or from about 0.1 to about 80 weight % or volume %, or more preferably, from about 0.2 to about 60 weight % or volume %, based upon the total formulation. Naturally, the amount of active compound(s) in each pharmaceutical composition may be prepared in such a way that a suitable dosage of the therapeutic molecules will be obtained using any given unit dose of the compound. Factors such as solubility, bioavailability, biological $t_{1/2}$, route of administration, product shelf life, as well as other pharmacological considerations will be contemplated by one of ordinary skill in the art of preparing such pharmaceutical formulations, and as such, a variety of dosages and treatment regimens may be desirable.

The pharmaceutical compositions disclosed herein may be administered by any effective method, including, without limitation, by parenteral, intravenous, intramuscular, or even intraperitoneal administration as described, for example, in U.S. Pat. Nos. 5,543,158, 5,641,515 and 5,399,363, each of which is specifically incorporated herein in its entirety by express reference thereto. Solutions of the disclosed compositions (either alone, or in combination with one or more additional active compounds) prepared free-base or in one or more pharmacologically acceptable buffer or salt solutions may be mixed with one or more surfactants, such as e.g. hydroxypropylcellulose, depending upon the particular application. The pharmaceutical forms adapted for injectable administration of the disclosed compositions include, without limitation, sterile aqueous solutions or dispersions, as well as one or more sterile powders for the extemporaneous preparation of sterile injectable solutions or dispersions including without limitation those described in U.S. Pat. No. 5,466,468 (which is specifically incorporated herein in its entirety by express reference thereto). In most applications of the invention, the pharmaceutical formulations will preferably be provided as a sterile solution, and one that is sufficiently fluid to permit easy syringability of the composition. Such formulations are also preferably sufficiently stable under the conditions of normal manufacture, storage, and transport, and are preferably preserved against the contaminating action of one or more microorganisms, such as viruses, bacteria, fungi, yeast, and such like.

The carrier(s) or vehicle(s) employed for delivery of the disclosed siRNA molecules may be any conventional pharmaceutical solvent and/or dispersion medium including, without limitation, water, alcohols such as ethanol, polyols such as glycerol, propylene glycol, and liquid polyethylene glycol, and the like, or a combination thereof), one or more vegetable oils, or any combination thereof. Additional pharmaceutically acceptable components may be included, such as to improve fluidity, prevent dissolution of the reagents, and such like.

Proper fluidity of the siRNA-based pharmaceutical formulations disclosed herein may be maintained, for example, by the addition of one or more carrier agents, such as e.g., a lecithin, or one or more surfactants, or any combination thereof. The inhibition or prevention of the action of microorganisms in the disclosed formulations can be achieved by the addition of one or more antibacterial or antifungal agents (for example, without limitation, a paraben, chlorobutanol, phenol, sorbic acid, thimerosal, or the like) to the composition during formulation. In many cases, it will be preferable to include one or more isotonic agents, for example, without limitation, one or more sugars or sodium chloride, or any combination thereof. Prolonged absorption of the injectable compositions can be brought about by the use in the compositions of agents delaying absorption, for example without limitation, aluminum monostearate, gelatin, or a combination thereof.

Systemic administration of the compounds and pharmaceutical formulations of the present invention is particularly contemplated to be an effective mode of providing the therapeutic compounds to the cells and/or tissues of interest, either alone, or in combination with one or more additional therapeutic and/or diagnostic reagents. However, in many embodiments of the invention, it is also contemplated that formulations of the disclosed compositions may be suitable for direct injection into one or more organs, tissues, tumors, or cell types in the body. Such injection sites include (without limitation) the circulatory system, the spinal cord, the lymphatic system, muscle, as well as direct administration to an organ or tissue site such as the breast, the heart, liver, lung, pancreas, intestine, brain, bladder, kidney, or other site within the patient's body, including, for example, without limitation, introduction of the delivered therapeutic or diagnostic agent(s) via intra-abdominal, intra-thoracic, intravascular, or by direct or indirect intra-tumoral/peri-tumoral delivery of the compositions disclosed herein to one or more tissues or sites within the animal body. In particular applications, the inventors contemplate the direct application of the siRNA anti-cancer therapeutics disclosed herein to one or more solid tumors or to one or more cancerous tissues or organs within, or about the body of the animal undergoing treatment, and in particular, to humans undergoing treatment for breast cancers, such as therapy-resistant breast cancers, and the like.

Administration of the disclosed compositions need not be restricted to one or more of these particular delivery modes, but in fact, the compositions may be delivered using any suitable delivery mechanism, including, for example, those known to the one of ordinary skill in the pharmaceutical and/or medical arts. In certain embodiments, the active ingredients of the invention may be formulated for delivery by needle, catheter, and related means, or alternatively, may be included within a medical device, including, without limitation, a drug-eluting implant, a catheter, or any such like device that may be useful in directing the compositions to the selected target site in the animal undergoing treatment. While the pharmaceutical formulations disclosed herein find particular use in the treatment of humans, in certain embodiments the methods and compositions disclosed herein may also be employed for treatment of non-human primates, or other mammalian or non-mammalian animal species. In such embodiments, the compositions disclosed herein may be provided in formulations that are acceptable for veterinary administration, including, without limitation, to selected livestock, exotic or domesticated animals, companion animals (including pets and such like), non-human primates, as well as zoological or otherwise captive specimens, and such like.

The siRNA compounds of the present invention may be combined with one or more therapeutic, diagnostic, or prophylactic compounds, reagents, formulations, or compositions, and in particular embodiments, the compounds may be formulated with one or more cytotoxic anti-cancer agents such as (without limitation) asparaginase, bleomycin, carboplatin, carmustine, chlorambucil, cisplatin, colaspase, cyclophosphamide, cytarabine, dacarbazine, dactinomycin, daunorubicin, doxorubicin (adriamycine), epirubicin, etoposide, 5-fluorouracil, hexamethylmelamine, hydroxyurea, ifosfamide, irinotecan, leucovorin, lomustine, mechlorethamine, 6-mercaptopurine, mesna, methotrexate, mitomycin C, mitoxantrone, prednisolone, prednisone, procarbazine, raloxifen, streptozocin, tamoxifen, thioguanine, topotecan, vinblastine, vincristine, vindesine, and any combination thereof.

Alternatively, the disclosed siRNA compositions may form a part of a combination treatment regimen, and may be further combined with one or more other antineoplastic agents such as, without limitation, aminoglutethimide, Lasparaginase, azathioprine, 5azacytidine cladribine, busulfan, diethylstilbestrol, 2',2'-difluorodeoxycytidine, docetaxel, erythrohydroxynonyladenine, ethinyl estradiol, 5-fluorodeoxyuridine, 5-fluorodeoxyuridine monophosphate, fludarabine phosphate, fluoxymesterone, flutamide, hydroxyprogesterone caproate, idarubicin, interferon, medroxyprogesterone acetate, megestrol acetate, melphalan, mitotane, paclitaxel, pentostatin, N-phosphonoacetyl-L-aspartate (PALA), plicamycin, semustine, teniposide, testosterone propionate, thiotepa, trimethylmelamine, uridine, vinorelbine, oxaliplatin, gemcitabine, capecitabine, epothilone and its natural or synthetic derivatives, temozolomide, tositumomab, trabedectin, and any combination thereof.

In practicing particular aspects of the invention, double-stranded antisense compounds may include overhanging nucleic acids, or alternatively, blunt-ended nucleic acids. As used herein, the term "blunt-ended" is intended to mean that the nucleic acid has no terminal overhangs. That is, at least one end of the double-stranded compound is blunt, siRNAs, whether canonical or blunt-ended, act to elicit dsRNAse enzymes and trigger the recruitment or activation of the RNAi antisense mechanism. In some aspects of the invention, single-stranded RNAi (ssRNAi) compounds that act via the RNAi antisense mechanism are also contemplated to be useful in certain applications.

In addition to the nucleotide sequences denoted herein, one or more additional modifications can be made to the double-stranded RNA compounds of the present invention, including, for example, 1) conjugating one or more functional groups to one of both of the termini; 2) altering, modifying, or conjugating one or more functional groups to one or more selected nucleobases, one or more sugar moieties, or to one or more of the internucleoside linkages within the siRNA molecule of interest: or 3) a combination thereof. Alternatively, the two strands (i.e., the "*sense" and the "antisense" strands) of a double-stranded nucleic acid molecule can be operably linked via one or more non-nucleic acid moieties or linker groups to each other, or to one or more additional molecules, moieties, labels, therapeutics, diagnostics, or such like.

When formed from a single strand, such nucleic acids can take the form of a self-complementary (sc) hairpin-type molecule that doubles back on itself to form a duplex. Thus, the RNA compounds disclosed herein can be fully or partially double-stranded molecules. When formed from two strands (or a single strand that takes the form of a self-complementary hairpin-type molecule doubled back on itself to form a duplex), the two strands (or duplex-forming regions of a single strand) are complementary when they base pair in Watson-Crick fashion.

BRIEF DESCRIPTION OF THE DRAWINGS

For promoting an understanding of the principles of the invention, reference will now be made to the embodiments, or examples, illustrated in the drawings and specific language will be used to describe the same. It will, nevertheless be understood that no limitation of the scope of the invention is thereby intended. Any alterations and further modifications in the described embodiments, and any further applications of the principles of the invention as described herein are contemplated as would normally occur to one of ordinary skill in the art to which the invention relates. The following drawings form part of the present specification and are included to demonstrate certain aspects of the present invention. The invention may be better understood by reference to the following description taken in conjunction with the accompanying drawings, in which like reference numerals identify like elements, and in which:

In FIG. 1A, ingenuity analysis shows green arrows which mark genes whose targeting reduced MSFE, e.g., Stat3 (within black box), while the red arrows mark genes whose targeting increased MSFE relative to control in SUM159 cells. In FIG. 1B, the same results are shown using the BT549 cell line;

FIG. 3A and FIG. 3B show the respective results of 1128 shRNA screen in SUM159 and BT549 cell lines that identified 128 shRNAs representing 108 unique genes and 78 shRNAs representing 72 genes which showed significant alteration in the MSFE in SUM159 and BT549, respectively; and FIG. 3C shows the significance analysis of genes in SUM159 and BT549 cell lines at p<0.05 to determine whether the genes had significantly changed in both cell lines; the genes identified by significance analysis are shown in Table 3:

FIG. 6A shows a schematic representation of high throughput mammosphere formation assay and lentiviral screen for tumorigenic signature in two triple negative breast cancer cell lines. SUM159 and BT549 and assayed for mammosphere forming efficiency; FIG. 6B illustrates a dose-dependent decrease in mammosphere forming efficiency with increasing concentration of positive control Notch inhibitor (MRK-003) added to SUM159 cells; and FIG. 6C demonstrates the efficiency of lentiviral transduction using pGIPZ vector system incorporated with GFP signal. SUM159 cells treated with control (no virus), or Bmi-1 shRNA encoded by pGIPZ lentiviral vector, showing mammosphere formation under bright field (BF) image and FITC image (green fluorescence) shows the percentage of transduction. pGIPZ vector system encoding Bmi-1 shRNA as transduction control demonstrated −85% efficiency of transduction under mammosphere formation conditions;

FIG. 7A shows a list of candidate genes identified by shRNA screen; FIG. 7B illustrates validation of BCSC targets with a low titer of virus (pGIPZ vector), at a multiplicity of infection (MOI) of 10, assayed by MSFE; and FIG. 7C shows the targeting BCSCs using siRNA with the sequence derived from pGIPZ vector shRNA against MLF2 and RPL39 genes in three triple negative cell lines, (MDAMB231, SUM159 and BT549) in 24-well, ultra-low-attachment plates, followed by analysis of secondary MSFE on Day 8. Data analyzed by one-way ANOVA and plotted as mean±SEM for n=6 replicates; *p<0.05;

FIG. 8A, FIG. 8B, and FIG. 5C show long-term, in vivo treatment in siRNA MDAMB231 xenografts. Triple-negative breast cancer cell line, MDAMB231 was injected into the mammary fat pad of SCID beige mice (n=9). These tumors were randomized into six groups: vehicle+scrambled siRNA, vehicle+RPL39 siRNA, vehicle 4 MLF2 siRNA, docetaxel (20 mg/kg, i.p.)+scrambled siRNA, docetaxel (20 mg/kg, i.p.)+RPL39 siRNA, docetaxel (20 mg/kg, i.p.)+MLF2 siRNA. Tumor volume was measured twice weekly and reported as tumor volume fold-change over time. FIG. 8A shows the tumor volume fold change in xenografts treated with scrambled. RPL39 and MLF2 siRNA, respectively; FIG. 8B shows the tumor volume xenografts treated with docetaxel in combination with scrambled, RPL39 and MLF2 siRNA, respectively over three cycles.

FIG. 9A shows the tumor volume fold change in xenografts treated with scrambled, RPL39 and MLF2 siRNA, respectively; FIG. 9B shows the tumor volume xenografts treated with docetaxel in combination with scrambled, RPL39 and MLF2 siRNA respectively. Mice were sacrificed after two weeks, and tumors collected and processed for MSFE and ALDF+ cells; FIG. 9C shows 10,000 cells/well were plated in 24-well ultralow attachment plates and primary and secondary MSFE was determined on Day 14 and Day 28, respectively; and FIG. 9D shows the % ALDF+ positive cells were determined using Aldefluor® assay followed by flow cytometry. Data were analyzed by one-way ANOVA, and plotted as mean±SEM for n=9 replicates; *p<0.05;

FIG. 10A shows the tumor volume fold change in xenografts treated with scrambled. RPL39 and MLF2 siRNA, respectively; FIG. 10B shows the tumor volume xenografts treated with docetaxel in combination with scrambled. RPL39 and MLF2 siRNA respectively. Mice were sacrificed after two weeks, and tumors were collected and processed for MSFE and ALDF (Aidefluor®-positive) cells; FIG. 10C shows 40,000 cells/well plated in a 6-well, ultra-low-attachment plates: primary, as well as secondary, MSFE was determined on Day 14 and Day 28, respectively: and FIG. 10D shows % ALDF+ cells were determined using the Aldefluor® assay followed by flow cytometry. Data were analyzed by one-way ANOVA, and are plotted as mean±SEM for n=9 replicates; *p<0.05;

FIG. 11A, FIG. 11B, and FIG. 11C show overexpression of RPL39 and MLF2 demonstrates an increase in wound healing, MSFE and proliferation. Triple-negative breast cancer cell lines. BT549 and MDAMB231, were transfected with MLF2 and RPL39 plasmids at 2 μg/mL concentration. FIG. 11A shows a representative image of MDAMB231 and BT549 cells treated with vehicle, MLF2, and RPL39 respectively. RPL39 and MLF2 overexpression demonstrates a statistically significant increase in the migration index of these cells; FIG. 11B shows the % MSFE was determined upon overexpression of MLF2 and RPL39 plasmid DNA in mammosphere growth media; and FIG. 11C shows the dose-dependent increase in proliferation was observed with 1 μg and 5 μg of plasmid DNA being transfected in the three TNBC cell lines. Data were analyzed by one-way ANOVA, and plotted as mean±SEM for n=9 replicates;*p<0.05;

FIG. 12A illustrates immunohistochemical images of triple negative cell lines transfected with 2 μg RPL39 and MLF2 plasmid DNA demonstrating an epithelial phenotype.; FIG. 12B shows the gene expression of MET markers SNAIL, N-cadherin (N-cad), vimentin (vim), fibronectin-1 (IFN-1), E-cadherin (E-cad), occludin (Occl) in two triple-negative cell lines, SUM159 and BT549;

In FIG. 13B, MLF2 siRNA was compared to scrambled siRNA, with a fold change >1.5 and p<0.005;

FIG. 14A shows the Western blot analysis of control compared to samples with overexpression of RPL39/MLF2 genes show an increase in both iNOS and eNOS with no changes in nNOS in three triple negative cell lines. SUM159. BT549, and MDAMB231 and FIG. 14B shows the Western blot analysis of triple negative cell lines treated in vitro with scrambled, RPL39 and MLF2 siRNAs, respectively; a decrease in iNOS and eNOS, with no substantial change in nNOS, was observed; FIG. 15A shows a representative image of RPL39 and MLF2 treated mice 6 weeks after primary tumor injection. FIG. 15B shows exemplary luminescence data that demonstrate a significant reduction in luciferase activity upon RPL39 and MLF2 siRNA treatment; FIG. 15C shows damaging mutations identified in RPL39 and MLF2 human lung metastasis using RNA-Seq and confirmed using allele-specific PCR; FIG. 15D is a cartoon that depicts a potential mechanism by which RPL39 and MLF2 siRNA are effective in reducing lung metastasis. These siRNAs block nitric oxide signaling which is required for mesenchymal to epithelial transition (MET), thereby preventing lung metastasis.

DESCRIPTION OF ILLUSTRATIVE EMBODIMENTS

Figure 1A:
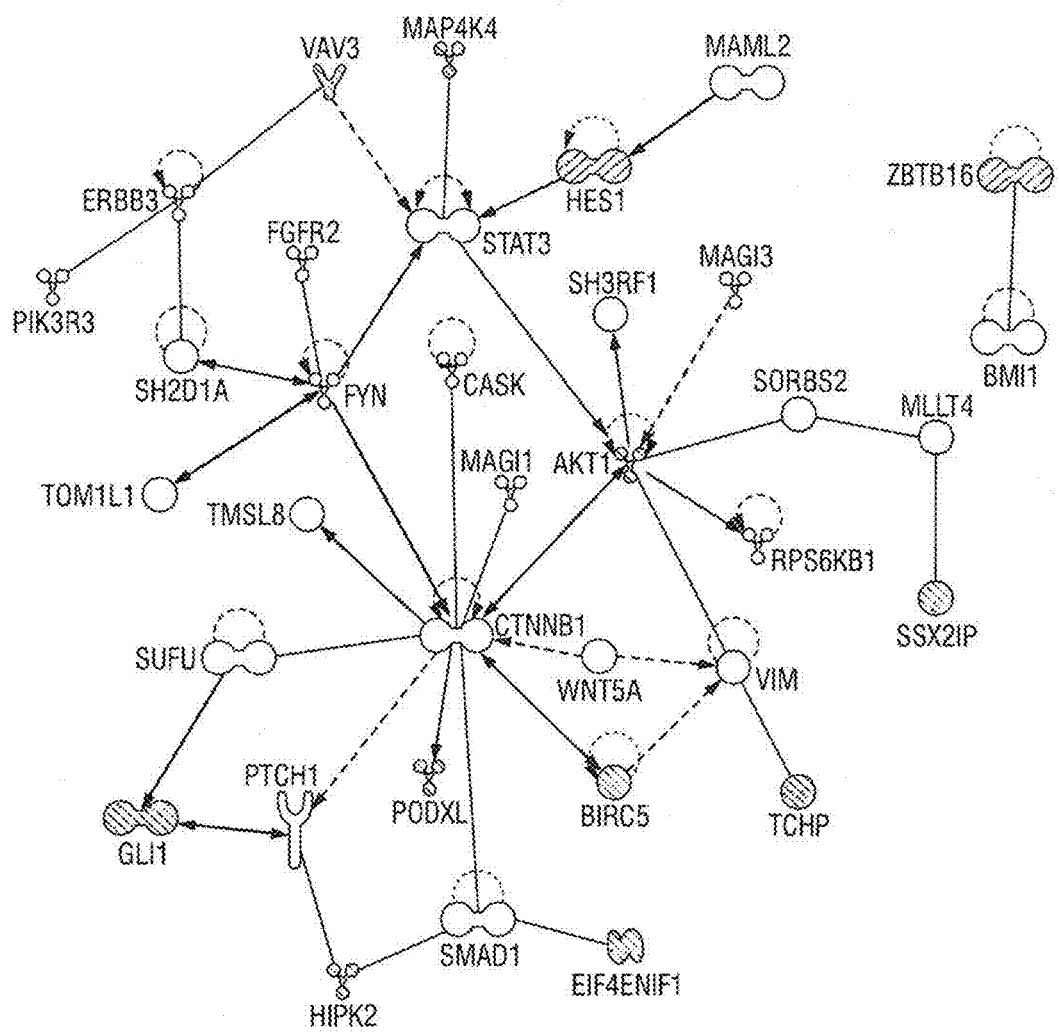
FIG. 1A and FIG. 1B show high-throughput MS-forming screen identifiers STAT3 as an important target of breast cancer stem cells. Breast cancer cells SUM159 (FIG. 1A) and BT549 (FIG. 1B) were plated (2,000 cells/well) and transduced with lentiviral vector pGIPZ (Open Biosystems, MA) containing individual shRNA's (~2/target) that targeted each of 493 breast CSC "signature" genes (see Creighton et al., 2009) or control shRNA. MSFE were counted 3 days after infection and the percentage of mammospheres calculated and compared to control.
Figure 1B:
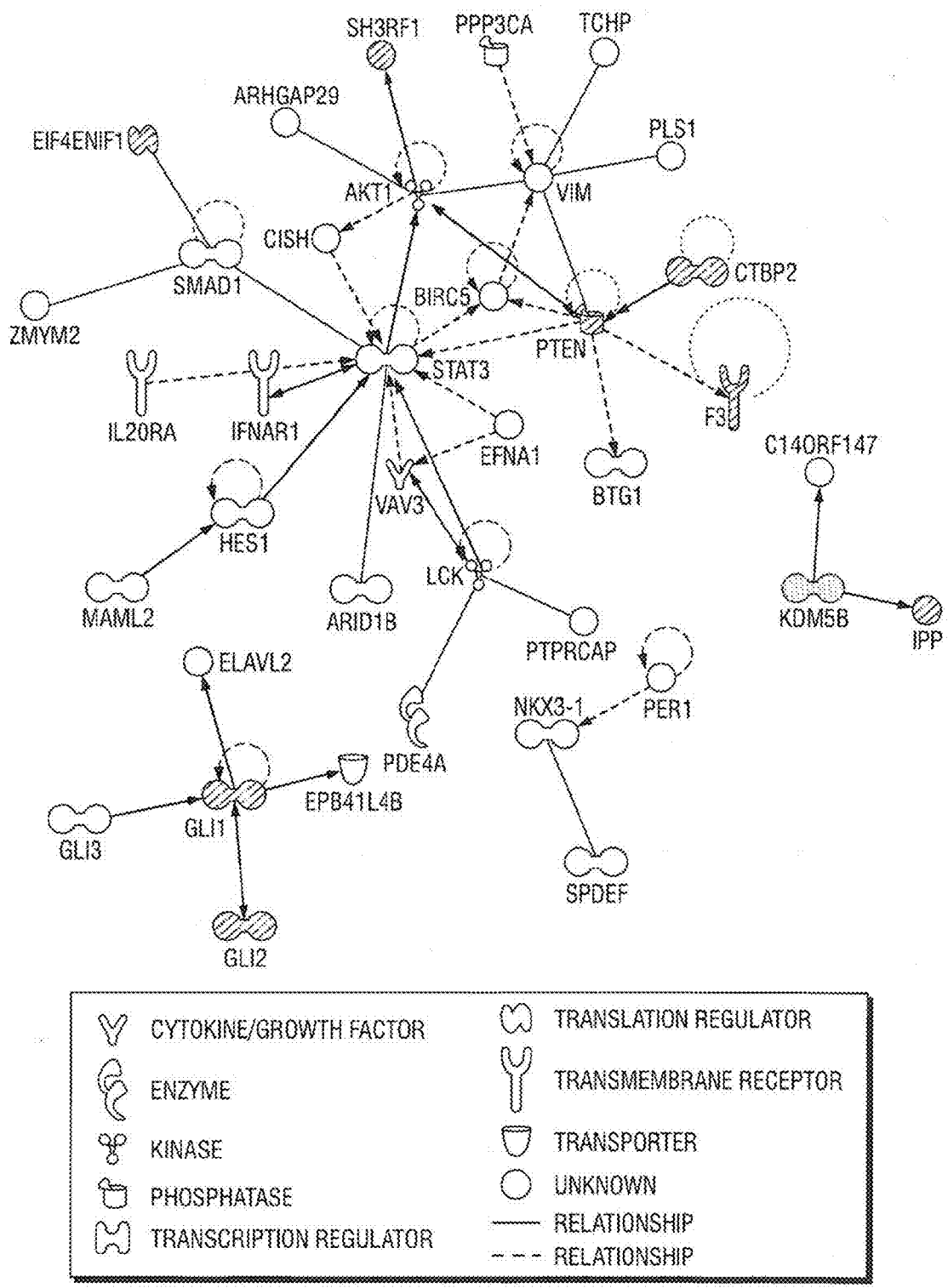
Figure 2A:
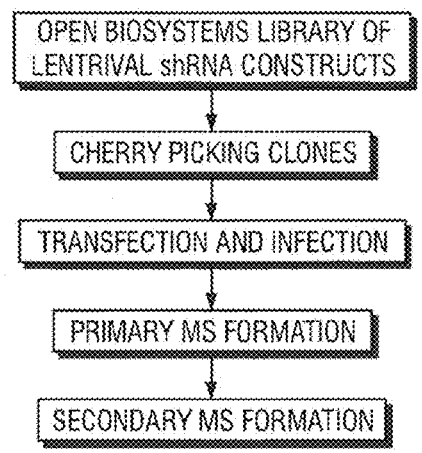
FIG. 2A and FIG. 2B show a schematic of lentiviral screen for tumorigenic signature using Open Biosystems GIPZ™ (Thermo Scientific) vector system using the high-throughput mammosphere formation assay (FIG. 2A); and a positive control notch inhibitor inhibiting MS formation in SUM159 cells.
Figure 2B:
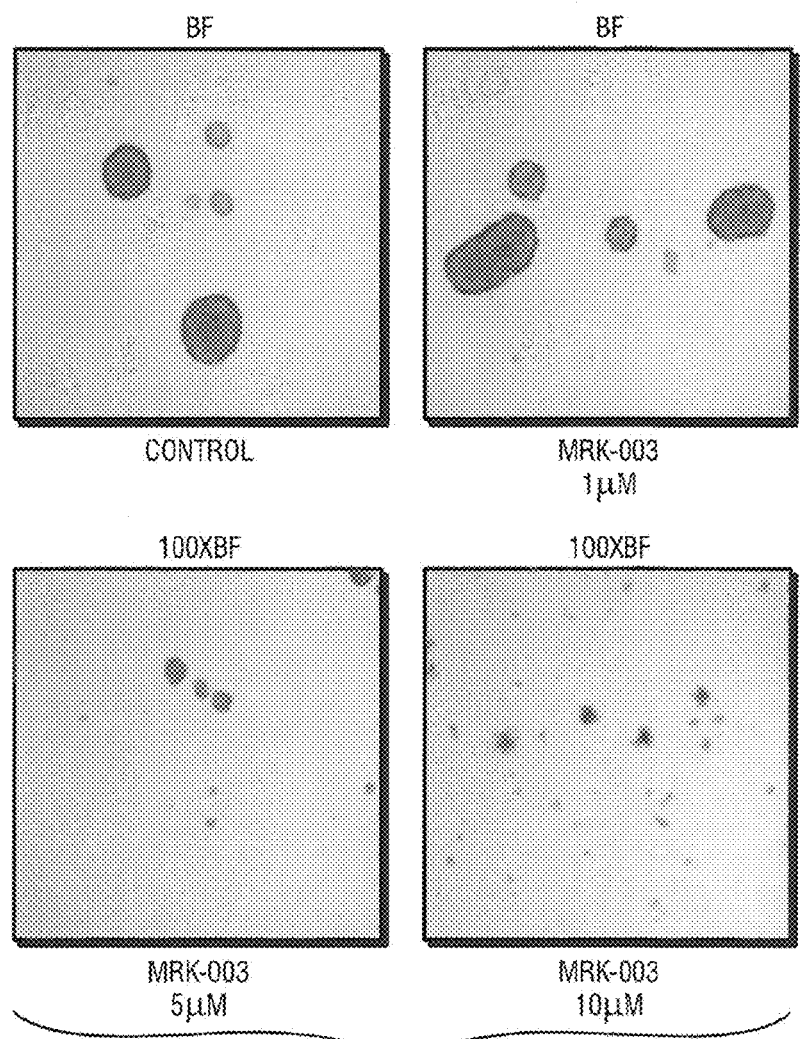
Figure 2C:
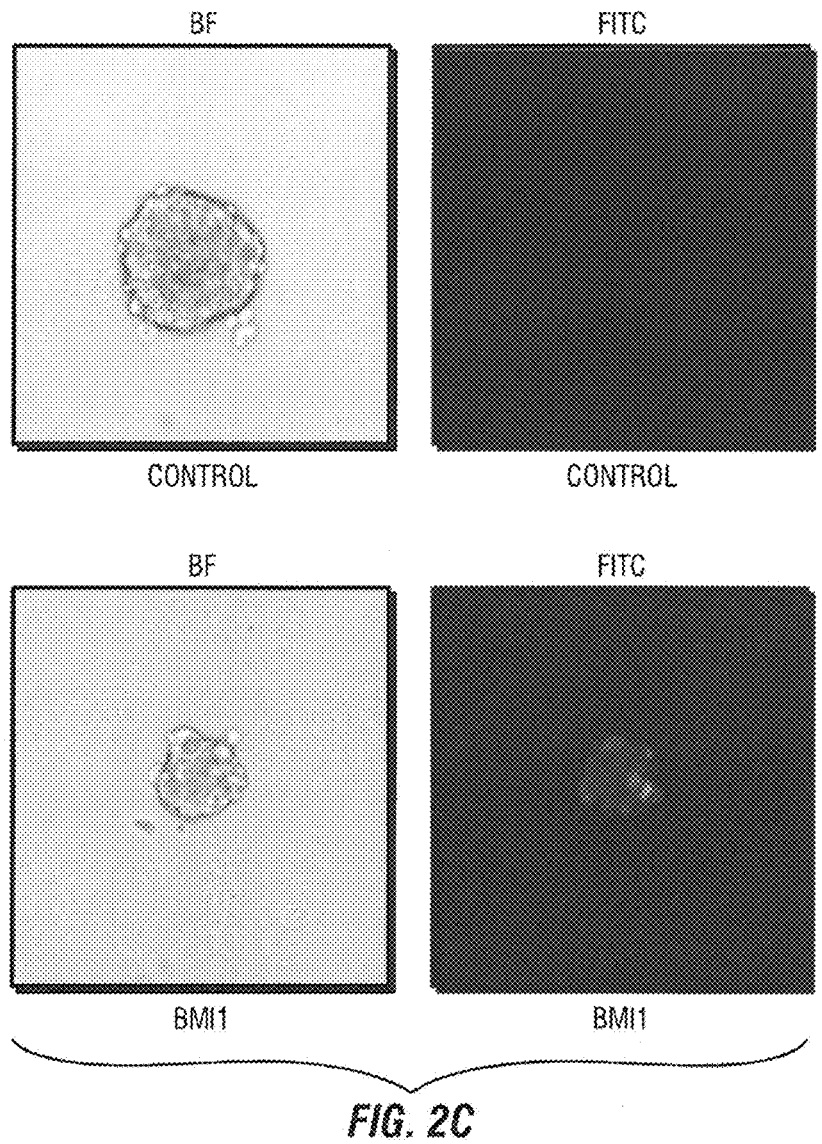
FIG. 2C shows lentiviral infection of Bmi-1 demonstrating ~85% efficiency of transduction in the mammosphere formation assay (FIG. 2B)
Figure 3A:
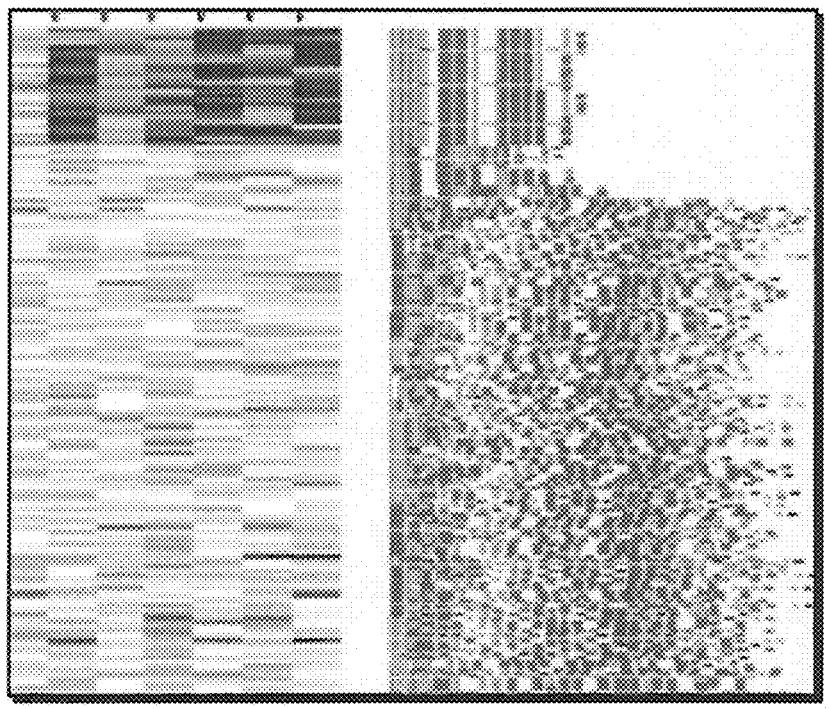
FIG. 3A, FIG. 3B, and FIG. 3C illustrate experimental results obtained from a study involving one exemplary embodiment of the present invention.
Figure 3B:
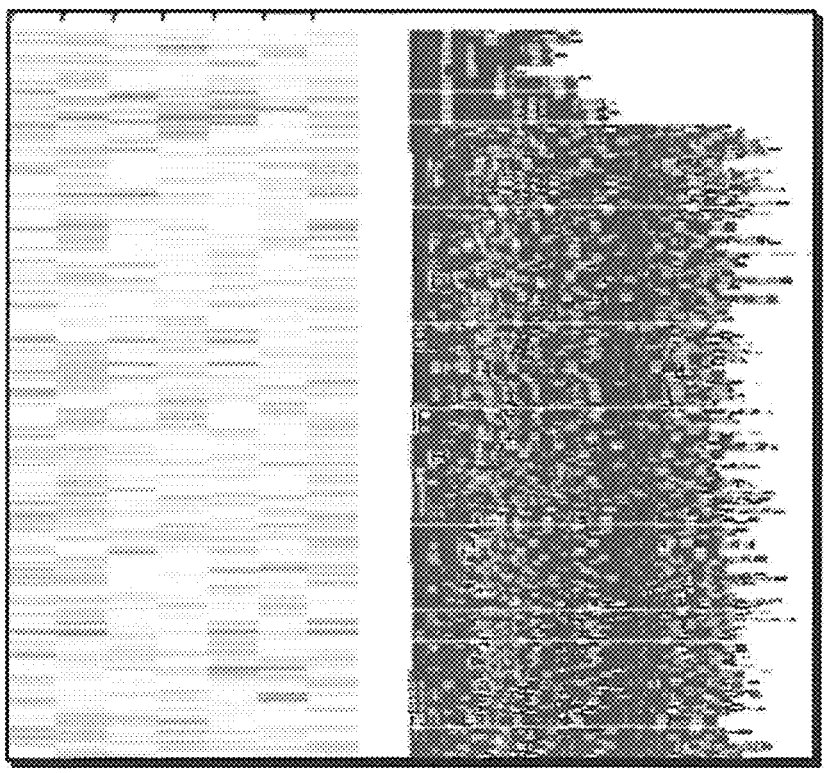
Figure 3C:
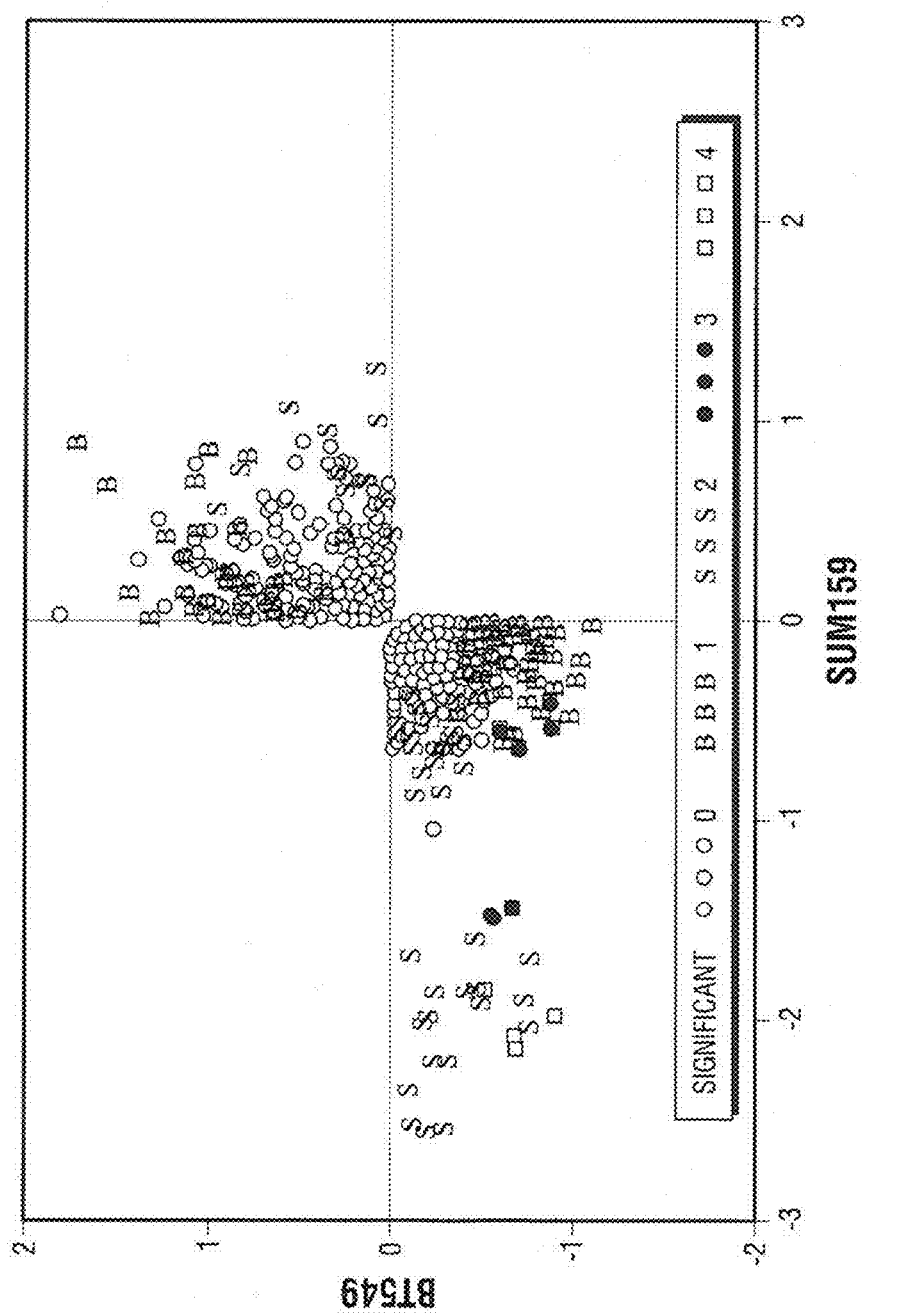

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would be a routine undertaking for those of ordinary skill in the art having the benefit of this disclosure.

Residual human breast tumor cells after conventional therapies are enriched in tumor-initiating cells characterized by CD44$^+$/CD24$^{-/low}$/lineage$^-$ with self-renewal capacities. Gene expression analyses in those cells and in breast cancer cells propagated as mammospheres (MSs) reveal an epithelial-mesenchymal-transition (EMT) signature mainly found in "claudin-low" molecular subtype human breast tumors (Creighton et al., 2009). In order to clarify the effect of silencing several genes found in the above mentioned signature over the self-renewal capacity on MSs with "claudin-low" features, the present study describes the knock-down in expression of three candidate genes based on preliminary screening. To this end, duplex small interfering RNA (siRNA) these three genes and scrambled siRNA as control, were introduced into neutral nanoliposomes (dioleoyl-phosphatidylcholine; "DOPC"), and using mesoporous microscale biodegradable silicon particles as carriers. This multistage siRNA delivery system has been reported as a good approach for sustained gene silencing (Tanaka et al., 2010).

"Claudin-low"-like human breast cancer cell lines (SUM159 and BT549) were plated in 24-well ultralow attachment plates with mammary epithelial growth medium (MEGM) (5,000 cells/well). Both cell lines were then treated with 1 μg/well/6 wells of silicon particles loaded with DOPC nanoliposomes/siRNA. The primary MSs were allowed to grow for 3 days. MFs were counted on Day 3 with a GelCount colony counter (Oxford Optronix, Oxford, UK). Mammosphere-Forming Efficiency (MSFE) was calculated by dividing the number of MSs by the number of seeded cells. In addition, established MSs were serially passaged by dissociation, and single cells were re-plated on fresh 24-well, ultra-low-attachment plates to form secondary mammospheres, which were counted after 3 days. One-way ANOVA and Tukey tests were performed. A p-value of less than 0.05 was considered significant. These results showed that silencing all three genes significantly reduced MSFE in both primary (1%, 0.9%, and 1.7% respectively) and secondary MSs (0.49%, 0.51%, and 0.45% respectively) when compared to the scrambled control (2.4% and 1% respectively) in BT549 cells.

Knocking-down of these genes significantly decreased the self-renewal capacity in mammospheres derived from "claudin-low"-like human breast tumor cells, being BT549 cells more sensitive than SUM159 cells to that silencing with siRNA loaded in DOPC nanoliposomes into silicon particles as carriers.

Dioleoylphosphatidylcholine (DOPC) nano-liposomes have been developed for the delivery of shRNA or siRNA oligonucleotides and shown to be efficient in siRNA incorporation as well as in viva delivery. SUM159 and BT549 breast cancer cells internalized particles efficiently as evidenced by the strong fluorescent signals, with fluorescent signals that remained strong for up to 10 days in tumor cells. Two key genes, Ribosomal protein L39-like (RPL39L) and Myeloid Leukemia factor 2 (NTN4/MLF2), have been identified, and the pathways that regulate growth and viability of tumor initiating cells were elucidated. Expression of the target genes was examined by Western blot analysis on days 3, 5, and 7, with these cells also being stained with Annexin V, and separated by FACS analysis for signs of cellular apoptosis. TIC assays, including, for example, flow cytometric analysis of CD44$^+$/CD24$^{-/low}$, ALDH1 and MSFE, may also be performed on target tissues as required.

The inventors contemplate that further mechanistic studies may be performed on the identified target genes, as desired, to elucidate the mechanism(s) of action of these proteins. For example, reverse-phase-protein arrays (RPPA) may be used to define resistant pathways, which may arise from such therapeutic regimens. RNA may also be isolated from tumor xenografts removed from mice treated with docetaxel, shRNA/siRNA alone, combination or vehicle (4 each) for use in gene expression profiling, to confirm proteomic findings at the transcriptional level demonstrating that there was successful inhibition of gene of interest transcriptional activity following treatment with shRNA probes. Such studies may also be useful in complementing proteomic studies to identify possible TIC escape pathways on a global level. Transcriptome analyses may also be performed to identify candidate genes within escape signaling pathways within the larger tumor survival network that may emerge to maintain tumor cell survival in the setting of shRNA/siRNA inhibition.

Therapy Resistant Tumor Initiating Cells (TICs) in Breast Cancer

Conventional chemotherapy and radiation therapy are effective initially in controlling breast cancer growth, yet patients frequently relapse over time. An explanation for relapse, which is gaining broad acceptance, is the existence of a rare sub-population of TIC that is intrinsically resistant to conventional therapy and has the potential of self-renewal giving them the ability to drive tumor growth and metastases at a later time (Stratford et al., 2010; Giatromanolaki et al., 2010; Resetkova et al., 2010: Klopp et al., 2010). Consistent with this hypothesis, it has been demonstrated that the CD44$^+$/CD24$^{-/low}$ lineage of breast cancer cells are resistant to conventional treatment, including chemotherapy, hormonal therapy, and radiation therapy (Al-Hajj et al., 2003; Al-Hajj et al., 2004; Yu et al., 2007), and are enriched in breast cancer metastasis (Tiezzi et al., 2011). In a recent neoadjuvant, breast cancer trial, the inventors have demonstrated a three-fold increase in the population of CD44$^+$/CD24$^{-/low}$ cells following chemotherapy in women with locally advanced breast cancer (Li et al., 2008). These observations stress the necessity to develop novel therapies to target TICs for the treatment of human breast cancer. Development of therapies against TICs will keep tumors static and prevent dissemination.

Gene Expression Signature of Enriched TIC Populations and Signaling Pathways

"Therapy resistant/tumor initiating cell signatures" have been identified from clinical samples (Creighton et al., 2009; Liu et al., 2007; Shipitsin et al., 2007). CD44$^+$/CD24$^{-/low}$ cells were isolated from biopsies obtained from women with primary breast cancer (Creighton et al., 2009). Populations enriched for tumorigenic cells were obtained by two methods: CD44$^+$/CD24$^{-/low}$ and the ability to form mammospheres (MS). Comparative gene expression analysis was performed in populations enriched for tumorigenic cells (CD44$^+$/CD24$^{-/low}$ or MS) vs. non-tumorigenic cells ("other" flow-sorted populations or bulk tumor cells, respectively). 154 transcripts were identified that were overexpressed both in the CD44+/CD24–/low population and in MS and 339 transcripts with decreased expression. Thus, a "CD44+/CD24–/low-MS gene signature" was defined which comprised the relative "up" and "down" patterns of the 493 transcripts present in the significant overlap between both comparisons. Using a systems-biology-based analysis, a network-based signature was generated for TICs (CD44+/CD24–/low) vs. non-TICs (all "other" flow-sorted fractions). From this signature, many important pathways were identified, which were associated with normal embryonic and organ development. For example, the Notch pathway (TACE→Notch→NICD→HES), the Hedgehog pathway (HH→PTCH→|SMO→SUFU-|GLI), the Wnt pathway (Wnt→Frizzled→DVL-GSK-3δ-β-catenin→TCF), the PI3K/Akt pathway (PI3K→PKD1→AKT-GSK-3δ-β-catenin), the p53 pathway (TERT-ATM→p53), and the JAK/Stat pathway (IL6→GP130→JAK→STAT3).

Essential Genes and Pathways in TICs

The gene expression signatures and pathways provide opportunities to develop treatment strategies that target TIC. However, most of the identified genes are considered "non-druggable", as no assay is available to measure their activities. High throughput lentiviral shRNA-based screening has been performed using two triple negative, human, breast cancer cell lines (SUM159 and BT549), to evaluate the role of genes that are overexpressed in TIC by measuring mammosphere-forming efficiency (MSFE). Briefly, shRNAs targeting all the ~500 genes from the existing tumorigenic signature (Creighton et al., 2009) were assembled into a lentiviral sub-library containing approximately 2 to 3 shRNAs for each gene to perform a high throughput, shRNA screen. These shRNAs were encapsulated in a lentiviral vector, and two cell lines (SUM159 and BT549) were individually infected with each shRNA (~1200 shRNAs in total). MSFE was then calculated in eight biological replicates using BIOMEK 3000 robotics. The MSFE data obtained from these studies were statistically analyzed for both cell lines, and 75 and 95 genes were identified respectively in SUM159 and BT549 cell lines at p<0.05. These results are described in the following example.

Multistage Delivery System (MDS)

Exemplary multistage delivery systems (MDS) for therapeutic use of the disclosed siRNA molecules may include, for example, a 1$^{st}$-stage porous silicon particle loaded with a 2$^{nd}$-stage nanoparticles (e.g., liposomes, micelles, and gold nanoparticles) incorporated with a 3$^{rd}$-stage therapeutic agent (such as siRNAs, oligonucleotides, chemotherapy agents, as well as combinations thereof).

1$^{st}$-stage particles are preferably optimized with respect to size, shape, surface chemistry, bio-recognition ligands, and porosity to achieve maximal tumor accumulation when delivered intravenously. Exemplary porous silicon particles have been developed that were designed to arrest on the surface of tumor-associated endothelial cells wherein 2$^{nd}$-stage particles contained therein may be released. These 2$^{nd}$-stage nanoparticles accumulate in tumor tissue by enhanced permeability and retention (EPR) effect based on enhanced penetration of nanoparticles through pores and fenestrations in the "leaky" neovasculature of solid tumors (Mukherjee et al. 2005), or via trans-cytosis or exocytosis of nanoparticles across the endothelial barrier. 3$^{rd}$-stage therapeutic agents contained within such nanoparticles are then released inside the tumor tissue for drug action.

Biocompatibility of pSI-Based Multistage Delivery Systems

Porous silicon is degraded inside the human body to orthosilicic acid. The porous structure allows for the release of harmless silicic acid in the aqueous solutions in the physiological pH range through hydrolysis of the Si—O bonds, which is subsequently excreted in the urine through the kidney (Jugdaohsingh et al. 2002). Biocompatibility of intravenously administered silicon particles has recently been investigated (Tanaka et al., 2010a). Unmodified silicon particles are negatively charged, and dissolve in phosphate buffer saline within ~48 hrs. To make silicon particles stable enough for their use in sustained drug delivery systems, standard pSI particles are modified with 3-aminopropyl-triethoxysilane (APTES). The resulting APTES-modified particles have been shown to persist at least as long as three weeks in vivo (Tanaka et al., 2010b).

Mice were treated with the surface-modified or unmodified particles with an acute single dose ($1\times10^7$, $1\times10^8$, or $5\times10^8$ particles/animal) or sub-chronic multiple doses ($1\times10^8$ particles/animal/week for 4 weeks). The treatment did not change plasma levels of renal (BUN and creatinine) or hepatic (LDH) biomarkers, or 23 tested cytokines. Particle treatment did not lead to infiltration of leukocytes into the liver, spleen, kidney, lung, brain, heart, and thyroid (Tanaka et al., 2010a). These results provided evidence of safe intravenous administration of silicon multistage particles as a drug delivery carrier for the therapeutic siRNA molecules disclosed herein, either alone, or in combination with one or more additional therapeutic and/or diagnostic molecules.

MDS for Bypassing Barriers to Drug Delivery

Achieving site-specific delivery of therapeutics is the key to eliminating undesirable side effects as well as enhancing therapeutic efficacy. Exemplary porous silicon particles have been fabricated and the effect of size and shape on biodistribution and cellular uptake have been tested (Decuzzi et al., 2009; Serda et al., 2009a). Successful loading of silicon particles has also been demonstrated for liposomes, micelles, gold nanoparticles, quantum dots, and carbon nanotubes. It has been demonstrated that silicon particles are phagocytosed by vascular endothelial cells and macrophages (Serda et al., 2009a: Serda et al., 2009b; Serda et al. 2009c). MDS are similarly internalized by phagocytic cells, with particles being localized in membrane-bound vesicles. Uptake of the MDS is followed by release of secondary nanoparticles from the porous matrix, and active sorting of the released nanoparticles which is influenced by particle attributes, such as surface chemistry. Endosomal sorting of nanoparticles into unique vesicles that are expelled from the endothelial cells has been demonstrated, thus providing a mechanism for crossing the endothelial barrier. Surface binding and extracellular arrest of silicon particles can alternatively be achieved based on choice of targeting ligand and particle geometry.

Human-Cancer-in-Mouse Tumor Model

Twenty primary xenografts have been established from biopsies of primary breast cancers using immunocompromised SCID/Beige mice. Interestingly, there was a doubling of transplantation efficiency of outgrowths from tissues obtained post-chemotherapy compared to pre-therapy specimens. It is highly possible the enhanced efficiency was due to enriched therapy-resistant cells (TICs) in post-chemotherapy patients (Li et al., 2008). Of these, the inventors have successfully transplanted over twenty different human breast cancers into tertiary xenografts. The gene expression patterns of the primary and tertiary xenografts are similar, thus confirming that a renewable source of human breast cancers has been established that are genotypically identical. These represent some of the best models available to test therapeutic efficacy on human cancer tissues in mice.

EXEMPLARY DEFINITIONS

Unless defined otherwise, all technical and scientific terms used herein have the same meaning as commonly understood by one of ordinary skill in the relevant arts. Singleton et al. (1994) and Hale and Markham (1991) are two examples of references that provide one of ordinary skill in the art with the general meaning of many of the terms used herein. A detailed discussion of the differences and similarities between shRNA and siRNA molecules can be found in Rao et al. (2009). Each of these references is specifically incorporated herein in its entirety by express reference thereto.

Still, certain terms are defined below for the sake of clarity and ease of reference. For example, the term "recombinant" refers to a polynucleotide or polypeptide that does not naturally occur in a host cell. A recombinant molecule may contain two or more naturally-occurring sequences that are linked together in a way that does not occur naturally. A recombinant cell contains at least one recombinant polynucleotide, at least one recombinant polypeptide, at least one recombinant vector, or any combination thereof.

The term "heterologous" refers to elements that are not normally associated with each other. For example, if a host cell produces a heterologous protein, that protein is not normally produced in that host cell. Likewise, a promoter that is operably linked to a heterologous coding sequence is a promoter that is operably linked to a coding sequence that it is not usually operably linked to in a wild-type host cell. The term "homologous," with reference to a polynucleotide or protein, refers to a polynucleotide or protein that occurs naturally in a host cell.

A "vector" refers to a polynucleotide designed to introduce nucleic acids into one or more host cells. A vector can autonomously replicate in different host cells or can integrate into a host cell genome. In certain cases, a vector may be an adenoviral vector or other viral vector that does not replicate or integrate in the host cell. Exemplary vectors include, without limitation, cloning vectors, expression vectors, shuttle vectors, plasmids, phage particles, cassettes, retroviral vectors, and the like. Certain vectors may be transfected into a cell and provide for transient expression of the encoded product. Such transient expression systems are well known in the art.

An "expression cassette" as used herein means a DNA or RNA construct comprising a coding region that is operably linked to a suitable control sequence that is capable of effecting transcription and/or translation the protein in a suitable host cell. Such control sequences may include a promoter to effect transcription, an optional operator sequence to control transcription, and, optionally, enhancers and other sequences that control termination of transcription and translation. Such cassettes can be constructed in a vector in order to transfer the expression cassette into a host cell.

As used herein, the term "promoter" refers to a regulatory sequence that initiates transcription of a downstream nucleic acid. The term "operably-linked" refers to an arrangement of elements that allows them to be functionally related. For example, a promoter is operably linked to a coding sequence if it controls the transcription of that sequence.

As used herein, the term "expression" refers to the process by which a polypeptide is produced based on the nucleic acid sequence of a gene. The process includes both transcription and translation.

The term "hybridization" refers to the process by which a strand of nucleic acid joins with a complementary strand through base pairing as known in the art. A given nucleic acid is considered "selectively hybridizable" to a reference nucleic acid sequence if the two sequences specifically hybridize to one another under moderate to high stringency hybridization and wash conditions. Moderate and high stringency hybridization conditions are known to those of ordinary skill in the molecular biology arts (see, e.g., Ausubel et al., 1995 or Sambrook et al. 2001: each of which is incorporated herein in its entirety by express reference thereto).

A "plurality" contains at least two members. In certain cases, a plurality may have at least 10, at least 100, at least 1000, at least 10,000, at least 100,000, or at least 1,000,000 or more members.

The terms "about" and "approximately" as used herein, are interchangeable, and should generally be understood to refer to a range of numbers around a given number, as well as to all numbers in a recited range of numbers (e.g., "about 5 to 15" means "about 5 to about 15" unless otherwise stated). Moreover, all numerical ranges herein should be understood to include each whole integer within the range.

As used herein, the term "carrier" is intended to include any solvent(s), dispersion medium, coating(s), diluent(s), buffer(s), isotonic agent(s), solution(s), suspension(s), colloid(s), inert(s) or such like, or a combination thereof that is pharmaceutically acceptable for administration to the relevant animal or acceptable for a therapeutic or diagnostic purpose, as applicable.

As used herein, the terms "protein," "polypeptide," and "peptide" are used interchangeably, and include molecules that include at least one amide bond linking two or more amino acid residues together. Although used interchangeably, in general, a peptide is a relatively short (e.g., from 2 to about 100 amino acid residues in length) molecule, while a protein or a polypeptide is a relatively longer polymer (e.g. 100 or more residues in length). However, unless specifically defined by a chain length, the terms peptide, polypeptide, and protein are used interchangeably.

As used herein, the term "buffer" includes one or more compositions, or aqueous solutions thereof, that resist fluctuation in the pH when an acid or an alkali is added to the solution or composition that includes the buffer. This resistance to pH change is due to the buffering properties of such solutions, and may be a function of one or more specific compounds included in the composition. Thus, solutions or other compositions exhibiting buffering activity are referred to as buffers or buffer solutions. Buffers generally do not have an unlimited ability to maintain the pH of a solution or composition; rather, they are typically able to maintain the pH within certain ranges, for example from a pH of about 5 to 7.

As used herein, the term "patient" (also interchangeably referred to as "host" or "subject") refers to any host that can serve as a recipient of one or more of the therapeutic or diagnostic formulations as discussed herein. In certain aspects, the patient is a vertebrate animal, which is intended to denote any animal species (and preferably, a mammalian species such as a human being). In certain embodiments, a "patient" refers to any animal host (including but not limited to, human and non-human primates, avians, reptiles, amphibians, bovines, canines, caprines, cavines, corvines, epines, equines, felines, hircines, lapines, leporines, lupines, murines, ovines, porcines, racines, vulpines, and the like, including, without limitation, domesticated livestock, herding or migratory animals or birds, exotics or zoological specimens, as well as companion animals, pets, and any animal under the care of a veterinary practitioner).

The term "e.g." as used herein, is used merely by way of example, without limitation intended, and should not be construed as referring only those items explicitly enumerated in the specification.

As used herein, the term "polypeptide" is intended to encompass a singular "polypeptide" as well as plural "polypeptides," and includes any chain or chains of two or more amino acids. Thus, as used herein, terms including, but not limited to "peptide," "dipeptide," "tripeptide," "protein," "enzyme," "amino acid chain," and "contiguous amino acid sequence" are all encompassed within the definition of a "polypeptide," and the term "polypeptide" can be used instead of, or interchangeably with, any of these terms. The term further includes polypeptides that have undergone one or more post-translational modification(s), including for example, but not limited to, glycosylation, acetylation, phosphorylation, amidation, derivatization, proteolytic cleavage, post-translation processing, or modification by inclusion of one or more non-naturally occurring amino acids. Conventional nomenclature exists in the art for polynucleotide and polypeptide structures. For example, one-letter and three-letter abbreviations are widely employed to describe amino acids: Alanine (A; Ala), Arginine (R; Arg), Asparagine (N; Asn), Aspartic Acid (D; Asp), Cysteine (C; Cys), Glutamine (Q; Gln), Glutamic Acid (E; Glu), Glycine (G; Gly), Histidine (H; His), Isoleucine (I; Ile), Leucine (L; Leu), Methionine (M: Met), Phenylalanine (F; Phe), Proline (P; Pro), Serine (S; Ser), Threonine (T; Thr), Tryptophan (W; Trp), Tyrosine (Y; Tyr), Valine (V; Val), and Lysine (K; Lys). Amino acid residues described herein are preferred to be in the "L" isomeric form. However, residues in the "D" isomeric form may be substituted for any L-amino acid residue provided the desired properties of the polypeptide are retained.

"Protein" is used herein interchangeably with "peptide" and "polypeptide," and includes both peptides and polypeptides produced synthetically, recombinantly, or in vitro and peptides and polypeptides expressed in vivo after nucleic acid sequences are administered into a host animal or human subject. The term "polypeptide" is preferably intended to refer to all amino acid chain lengths, including those of short peptides of from about 2 to about 20 amino acid residues in length, oligopeptides of from about 10 to about 100 amino acid residues in length, and polypeptides including about 100 amino acid residues or more in length. The term "sequence," when referring to amino acids, relates to all or a portion of the linear N-terminal to C-terminal order of amino acids within a given amino acid chain, e.g., polypeptide or protein; "subsequence" means any consecutive stretch of amino acids within a sequence, e.g., at least 3 consecutive amino acids within a given protein or polypeptide sequence. With reference to nucleotide and polynucleotide chains, "sequence" and "subsequence" have similar meanings relating to the 5'-to-3' order of nucleotides.

As used herein, the term "kit" may be used to describe variations of the portable, self-contained enclosure that includes at least one set of reagents, components, or pharmaceutically-formulated compositions to conduct one or more of the therapeutic methods of the invention. Optionally, such kit may include one or more sets of instructions for use of the enclosed reagents, such as, for example, in a laboratory or clinical application.

The term "about," as used herein, should generally be understood to mean "approximately", and typically refers to numbers approximately equal to a given number recited within a range of numerals. Moreover, all numerical ranges herein should be understood to include each whole integer within the range. In accordance with long standing patent law convention, the words "a" and "an" when used in this application, including the claims, denotes "one or more."

As used herein, "an effective amount" would be understood by those of ordinary skill in the art to provide a therapeutic, prophylactic, or otherwise beneficial effect.

EXAMPLES

The following examples are included to demonstrate illustrative embodiments of the invention. It should be appreciated by those of ordinary skill in the art that the techniques disclosed in this example represent techniques discovered to function well in the practice of the invention, and thus can be considered to constitute preferred modes for its practice. However, those of ordinary skill in the art should, in light of the present disclosure appreciate that many changes can be made in the specific embodiments which are disclosed and still obtain a like or similar result without departing from the spirit and scope of the invention.

Example 1 shRNA Knockdown of Differentially-Expressed Genes Experimental Procedures

In previously published results, the inventors described a breast cancer stem cell signature that comprised a set of 493 statistically significant, differentially expressed genes that were present in a tumorigenic subpopulation of breast cancer cells (Creighton et al. 2009). The biological confirmation of the significance of these differentially expressed genes was conducted using a shRNA-based gene knockdown approach, correlating the selective knockdown of target genes with mammosphere formation efficacy (MSFE), an in vitro assay for self-renewal. A library of shRNAs which targets the entire human genome (Open Biosystems, Boston, Mass., USA) was used to create a sub-library of shRNAs against the 493 differentially expressed genes in the tumorigenic signature. A total of 1124 shRNAs (~2-3 shRNA per gene), and appropriate control shRNAs that were encoded in the pGIPZ vector with a green fluorescent protein tag were selected and arrayed on 13×96-well microtiter plates.

These shRNAs were packaged into lentiviral particles using a second-generation lentiviral packaging system (Addgene, Cambridge, Mass., USA) in 293T cells plated on 96-well plates. The supernatant was then harvested for transduction and expression in a wide range of cell types. Specifically, lentiviruses were collected 3 days after transfection, frozen at −80° C. immediately, and then thawed for transducing two different breast cancer cell lines SUM159PT (American Type Culture Collection; Manassas, Va., USA) and BT549 (ATCC) with 8 biological replicates. Cells were plated in 13×96-well ultra-low attachment plates, at 2000 cells/well, with one shRNA being transduced per well using the Biomek 3000 automated workstation (Beckman Coulter; Brea, Calif. USA), in order to ensure reproducibility and accuracy.

The lentiviral transduction rate (~80-90%) in these cell lines was evaluated by fluorescence microscopy using the GFP tag in the pGIPZ vector. MSFE was then assessed in a high throughput screening approach of all 493 genes. The results were compared with negative empty vector and positive controls with γ-secretase inhibitor (MRK-003, Merck, Inc.), which have previously been shown to effectively decrease MSFE (Grudzien et al., 2010).

Confirmatory Screen of the Top Hits on of the Primary Screen.

Using the top 15 hits from the primary screen in 96-well plates, the data were reanalyzed by conducting the MFSE assay in a 24-well plate with n=12 replicates at the same time using a known concentration of virus (MOI of 10) in order to identify the most efficient shRNAs. Briefly, 5000 cells/well were plated in mammosphere medium and lentivirally-packaged shRNA at MOI of 10 was added to the cells. The MSFE was calculated by counting the cells on Day 3 using Gelcount® (Oxford Optronix; Oxford. UK). This method of screening in both the BT549 and SUM159 cell line allowed confirmation of the most significant genes, and permitted follow up with suitable in vivo xenograft studies.

In Vitro Nanoliposome-Packaged siRNA Studies.

To develop a more clinically relevant model, two of the identified candidates (MLF2 and RPL39L) were compared to Stat3 (positive control), and their siRNA sequences identified within the shRNA vector. These siRNAs were then packaged in nanoliposomes and tested for MSFE using the same protocol as above, except for the addition of packaged siRNA instead of lentiviral shRNA. (N.B. wherein shRNA requires a promoter and needs to be transcribed in order to function, siRNA functions by itself once incorporated into recipient cells).

Xenograft Studies.

In vivo studies were performed to document the effect of two of the targets identified in the screen using siRNA packaged in multistage nanoparticles in a triple negative (estrogen receptor/progesterone receptor/HER2 negative) cell line (SUM159), and in human cancer xenografts (BCM-2665) derived from biopsies of human primary breast cancers transplanted in SCID Beige mice (36 mice per xenograft line, 9 mice per treatment arm). When the tumors reached between 200-400 mm$^3$, mice were divided into six groups: (1) vehicle-treated; (2) chemotherapy-treated (day 1 with one dose of docetaxel 20 mg/mL by intraperitoneal (i.p.) injection; (3) siRNA against MLF2 packaged in nanoparticles (single injection i.v. on Day 1); 4) combination treatment with docetaxel (20 mg/mL i.p. on Day 1) and siRNA against MLF2 (single injection i.v. on Day 1); (5) siRNA against RPL39L packaged in nanoparticles (single injection iv. on Day 1): and (6) combination treatment with docetaxel (20 mg/mL i.p. on Day 1) and siRNA against inhibitor MLF2 (single injection i.v. on Day 1). Animals were sacrificed on Day 14. The tumors were harvested and analysis for downstream effects of treatment performed using mammosphere forming efficiency and FACS analysis.

TIC Analysis by FACS and MSFE.

The fraction of tumor-initiating cells in the xenograft tumors with the different treatment groups were processed by mincing the tumors and digesting them using collagenase type III, for 3 hrs at 37° C. to dissociate the tumors into single cells. Changes in CD44+/CD24/Lin− and Aldefluor® were analyzed, as previously described (Li et al., 2008). Briefly, cells were stained with primary antibodies anti-CD44 labeled APC (dilution 1:10, BD Biosciences. San Jose, Calif., USA), anti-CD24 labeled FITC (dilution 1:10, BD Biosciences), and H2KD PE was used to eliminate mouse cells and all lineage positive cells. Incubation was performed for 15 min on ice in HBSS (Hanks Balanced Salt Solution, GIBCO® Life Technologies, Grand Island, N.Y., USA) with 2% FBS for the antibodies and 45 min for Aldefluor® reagent (STEMCELL Technologies, Inc., Vancouver, BC, Canada). After incubation, cells were washed once with HBSS and were re-suspended in HBSS supplemented with 2% FBS. PI was added to the cells for "live/dead" gating prior to FACS analysis.

Mammosphere culture, an in vitro assay for stem cell self-renewal, was performed as previously described (Dontu et al., 2003; Dontu et al. 2005: Li et al., 2008). Single cells were plated in ultra-low attachment plates (Corning, Inc.; Acton, Mass., USA). The cells were plated at a density of 40,000 viable cells/mL for BCM-2665 in primary culture, and 10,000 cells/mL in secondary culture. For mammosphere culture, cells were grown in a serum-free mammary epithelial basal medium (MEGM) (Lonza, Inc., Allendale, N.J. USA) supplemented with B27 (Invitrogen, Inc., Carlsbad, Calif., USA), 20 ng/mL EF (BD Biosciences, Inc., San Jose, Calif., USA), 1% heparin (Sigma-Aldrich, St. Louis, Mo., USA) in a humidified incubator (10% $CO_2$:95% air, 37° C. for 14 days) as previously described (Li et al. 2008).

Statistical Analysis.

For shRNA knockdown studies, the mean and the standard deviation from all measurements of each plate for each replicated experiment were estimated. The Z-score was calculated by subtracting the mean of the plate values and dividing this difference by the standard deviation. One sample t-test was then utilized to test whether the mean score of each gene significantly differs from zero. For tumor volume fold-change comparisons, one-way Anova was used to compare different treatment groups. This was followed by Tukey analysis for a pairwise comparison of different treatment groups. For the tumor recurrence studies, events were defined as first appearance of tumor >50 $mm^3$ after completion of treatment. Time to recurrence was derived by Kaplan-Meier method, with differences compared using the generalized Mann-Whitney-Wilcoxon rank-sum test.

Table 1 shows sixteen exemplary genes targeted by the siRNA molecules of the present invention. This table also shows the nucleotide sequences of the sense and antisense strands of the 16 resulting siRNAs. Table 2 lists the names of the genes referred to in Table 1 by their genetic loci.

TABLE 1

EXEMPLARY SIRNA-TARGETED GENES

|  |  | Name (Sense) | Sequence (Sense) 5'-to-3' | SEQ ID NO: |
|---|---|---|---|---|
|  |  | Scrambled_sense | ATCTCGCTTGGGCGAGAGTAAG | SEQ ID NO: 1 |
| STAT3 | signal transducer and activator of transcription 3 | STAT3_88502sense | CCAAGTTCATGGCCTTAGGTAG | SEQ ID NO: 2 |
| MLF2 | Myeloid leukemia factor 2 | MLF2_sense | CCCTGATGGATCCCTTTGCTAT | SEQ ID NO: 3 |
| MAGI3 | Membrane associated guanylate kinase, WW and PDZ domain containing 3 | MAGI3_sense | CCCTTCTGAGGTCTACCTGAAA | SEQ ID NO: 4 |
| SHB | Src homology 2 domain containing adaptor protein B | SHB_sense | ACCTTCTTTGCTGGCTTTATTA | SEQ ID NO: 5 |
| HN1L | Hematological and neurological expressed 1-like (C20ORF23) | HN1L_sense | CGCCTGTATTTGGAAGATTTAA | SEQ ID NO: 6 |
| KLF16B | Kinesin family member 16B | KIF16B_sense | CGGCTGAGAAGTTTCAGATATT | SEQ ID NO: 7 |
| GNAZ | Guanine nucleotide binding protein (G protein), alpha z polypeptide | GNAZ_sense | CGCTAAGTGTCTTGGTATTTAA | SEQ ID NO: 8 |
| PLCH1 | phospholipase C. eta 1 | PLCH1_sense | CGCTCAGTACCTGAAAGGAATA | SEQ ID NO: 9 |
| ZTBT16 | Zinc finger and BTB domain containing-16 | ZBTB16_sense | ACCCTTCAGTCTCCACTTCATT | SEQ ID NO: 10 |
| MAP7 | microtubule-associated protein 7 | MAP7_sense | ATCTTACATAATGTATTTATAA | SEQ ID NO: 11 |
| MARVELD2 | MARVEL domain containing 2 | MARVELD2_sense | ATGCTACTATCCGTTATTTAAT | SEQ ID NO: 12 |
| TRBV19 | T cell receptor beta variable orphans on chromosome 9 | TRBV19_sense | AACCCTGAGTTGTGAACAGAAT | SEQ ID NO: 13 |
| Stat3 | Signal transducer and activator of transcription 3 | STAT3/ 262105_sense | ACGGCGTCCAGTTCACTACTAA | SEQ ID NO: 14 |
| RPL39L | Ribosomal protein L39-like | RPL39L_sense | ACGATTCCTGGCCAAGAAACAA | SEQ ID NO: 15 |

TABLE 1-continued

EXEMPLARY SIRNA-TARGETED GENES

| | | Name (Sense) | Sequence (Sense) 5'-to-3' | SEQ ID NO: |
|---|---|---|---|---|
| HMBX3 | HMG box domain containing 3 [Homo sapiens] (KIAA) | HMGXB3_sense | GCCTGTCTATGTGGTAGAT | SEQ ID NO: 16 |
| | | Scrambled_anti | CTTACTCTCGCCCAAGCGAGAG | SEQ ID NO: 17 |
| STAT3 | signal transducer and activator of transcription 3 | STAT3_88502anti | CTACCTAAGGCCATGAACTTGA | SEQ ID NO: 18 |
| MLF2 | Myeloid leukemia factor 2 | MLF2_anti | ATAGCAAAGGGATCCATCAGGA | SEQ ID NO: 19 |
| MAGI3 | Membrane associated guanylate kinase, WW and PDZ domain containing 3 | MAGI3_anti | TTTCAGGTAGACCTCAGAAGGA | SEQ ID NO: 20 |
| SHB | Src homology 2 domain containing adaptor protein B | SHB_anti | TAATAAAGCCAGCAAAGAAGGG | SEQ ID NO: 21 |
| HN1L | Hematological and neurological expressed 1-like (C20ORF23) | HN1L_anti | TTAAATCTTCCAAATACAGGCA | SEQ ID NO: 22 |
| KLF16B | Kinesin family member 16B | KIF16B_anti | AATATCTGAAACTTCTCAGCCT | SEQ ID NO: 23 |
| GNAZ | Guanine nucleotide binding protein (G protein), alpha z polypeptide | GNAZ__anti | TTAAATACCAAGACACTTAGCT | SEQ ID NO: 24 |
| PLCH1 | phospholipase C, eta 1 | PLCH1_anti | TATTCCTTTCAGGTACTGAGCA | SEQ ID NO: 25 |
| ZTBT16 | Zinc finger and BTB domain containing-16 | ZBTB16_anti | AATGAAGTGGAGACTGAAGGGC | SEQ ID NO: 26 |
| MAP7 | microtubule-associated protein 7 | MAP7_anti | TTATAAATACATTATGTAAGAG | SEQ ID NO: 27 |
| MARVELD2 | MARVEL domain containing 2 | MARVELD2_anti | ATTAAATAACGGATAGTAGCAG | SEQ ID NO: 28 |
| TRBV19 | T cell receptor beta variable orphans on chromosome 9 | TRBV19_anti | ATTCTGTTCACAACTCAGGGTC | SEQ ID NO: 29 |
| stat3 | Signal transducer and activator of transcription 3 | STAT3/262105_anti | TTAGTAGTGAACTGGACGCCGG | SEQ ID NO: 30 |
| RPL39L | Ribosomal protein L39-like | RPL39L_anti | TTGTTTCTTGGCCAGGAATCGC | SEQ ID NO: 31 |
| HMBX3 | HMG box domain containing 3 [Homo sapiens] (KIAA) | HMGXB3_anti | ATCTACCACATAGACAGGC | SEQ ID NO: 32 |

TABLE 2

| Locus | Gene Name |
|---|---|
| RPL39L | Ribosomal protein L39-like |
| MLF2 | Myeloid leukemia factor 2 |
| STAT3 | Signal transducer and activator of transcription 3 |
| MAP7 | Microtubule-associated protein 7 |
| MARVELD2 | MARVEL domain containing 2 |
| HN1L | Hematological and neurological expressed 1-like (C20ORF23) |
| TRBV | T cell receptor beta variable orphans on chromosome 9 |
| GNAZ | Guanine nucleotide binding protein (G protein), alpha z polypeptide |
| KLF16B | Kinesin family member 16B (C16ORF23) |
| ZTBT16 | Zinc finger and BTB domain containing-16 |
| PLCH1 | Phospholipase C, Eta 1 |
| MAGI3 | Membrane associated guanylate kinase, WW and PDZ domain containing 3 |
| SHB | Src homology 2 domain containing adaptor protein B |
| HMBX3 | HMG box domain containing 3 [Homo sapiens] (KIAA) |

TABLE 3

| Gene_sbRNA | GENE | SUM 159 Z-score | SUM 159 p < 0.01 | SUM 159 $0.01 \leq p < 0.05$ | SUM 159 $0.05 \leq p < 0.1$ | BT 549 Z-score | BT 549 p < 0.0 | BT 549 $0.01 \leq p < 0.05$ | BT 549 $0.05 \leq p < 0.1$ | Significant |
|---|---|---|---|---|---|---|---|---|---|---|
| MAG13_172_0143_BDave5_C4_5 | MAG13 | 0.756 | | 1 | | 0.858 | | | 1 | 2 |
| SHB_172_0484_BDave_F2_8 | SHB | -0.276 | | 1 | | -0.417 | | | 1 | 2 |
| AA_GSI_pos1_1 | GS11 | -2.026 | 1 | | | -0.731 | | | 1 | 3 |
| AA_GSI_pos1_10 | GS11 | -1.697 | | 1 | | -0.719 | | | 1 | 3 |
| AA_GSI_pos1_6 | GS11 | -1.904 | | 1 | | -0.688 | | | 1 | 3 |
| AA_GSI_pos2_13 | GS12 | -1.857 | 1 | | | -0.397 | | | 1 | 3 |
| AA_GSI_pos2_5 | GS12 | -1.923 | 1 | | | -0.463 | | | 1 | 3 |
| C16orf34_172_0256_BDave1_H12_1 | C16orf34 | -0.611 | | | 1 | -0.598 | | 1 | | 4 |
| C20orf23_172_0534_BDave1_A6_1 | C20orf23 | 0.413 | | | 1 | 0.280 | 1 | | | 4 |
| GNAZ_172_0024_BDave9_E2_9 | GNAZ | 0.847 | | | 1 | 1.026 | | 1 | | 4 |
| PLCH1_172_0207_BDave7_F2_7 | PLCH1 | -0.395 | | | 1 | -0.457 | | 1 | | 4 |
| ZBTB16_172_0522_BDave13_G1_13 | ZBTB16 | 0.677 | | | 1 | 1.585 | | 1 | | 4 |
| AC_GAPDH_neg1_4 | GAPDH1 | 0.697 | | | 1 | 1.101 | | 1 | | 5 |
| KIAAD194_172_0473_BDave11_C8_11 | KIAAD194 | -0.412 | | 1 | | -0.874 | 1 | | | 6 |
| MAP7_172_0417_BDave_F4_5 | MAP7 | -0.547 | | 1 | | -0.599 | 1 | | | 6 |
| MARVELD2_172_0055_BDave5_F9_5 | MARVELD2 | -0.649 | | 1 | | -0.709 | 1 | | | 6 |
| NTN4_172_0664_BDave7_D2_7 | NTN4 | -0.541 | 1 | | | -0.882 | 1 | | | 6 |
| RPL39L_172_0645_BDave7_D2_7 | RPL39L | -1.480 | | 1 | | -0.558 | 1 | | | 6 |
| TRBV19_172_0012_BDave14_B2_14 | TRBV19 | -1.434 | | 1 | | -0.665 | 1 | | | 6 |
| AA_GSI_pos1_11 | GS11 | -2.078 | 1 | | | -0.675 | | 1 | | 7 |
| AA_GSI_pos1_8 | GS11 | -1.850 | 1 | | | -0.519 | | 1 | | 7 |
| AA_GSI_pos2_10 | GS12 | -2.139 | 1 | | | -0.685 | | 1 | | 7 |
| AA_GSI_pos2_8 | GS12 | -1.971 | 1 | | | -0.894 | | 1 | | 7 |

TABLE 4

LIST OF SHRNA TARGETS CONFIRMED TO WORK IN BOTH CELL LINES

| Sample No. | Gene ID | Description |
|---|---|---|
| 1 | RPL39L | Ribosomal protein L39-like |
| 2 | MLF2 | Lyeloid Luekemia Factor 2 |
| 3 | KLF16B | Kinesin Family Member 16B |
| 4 | STAT3 | Signal Transducer and Activator of Transcription 3 |
| 5 | GAPDH | Glyceraldehyde-3-Phosphate Dehydrogenase |

Example 2

Increase of TIC Population in Xenografts after Docetaxel Treatment

Figure 4A:
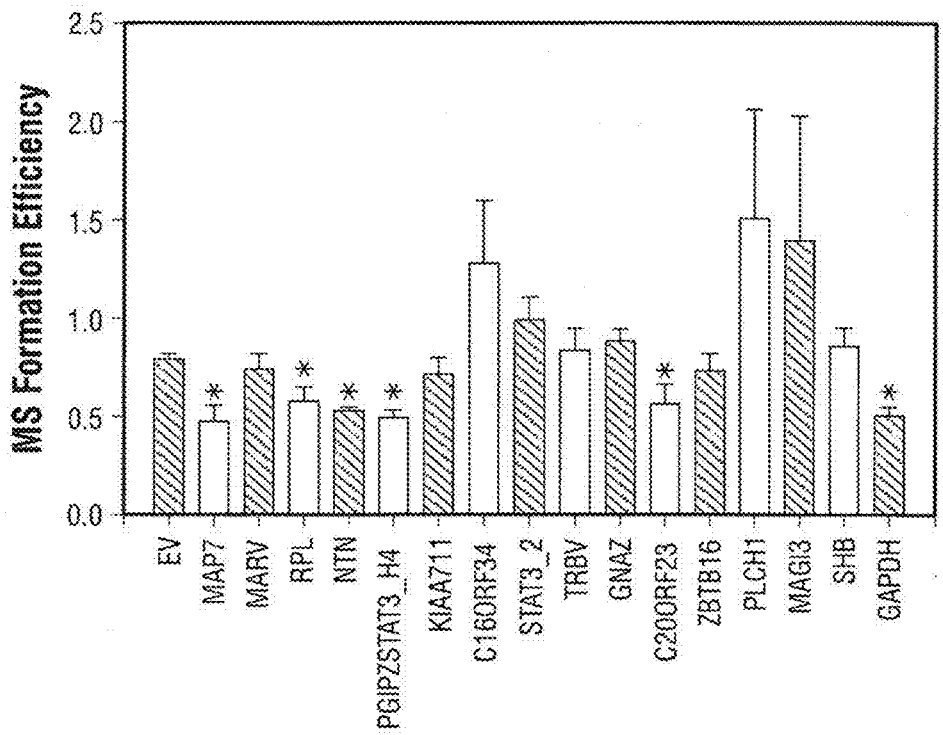
FIG. 4A and FIG. 4B show the confirmation of targets using fixed amount of virus (MOI of 10) in a standard 24-well mammosphere-forming efficiency assay using cell lines BT549 and SUM159: the finalized list of shRNA targets after screening both cell lines are listed in Table 4.
Figure 4B:
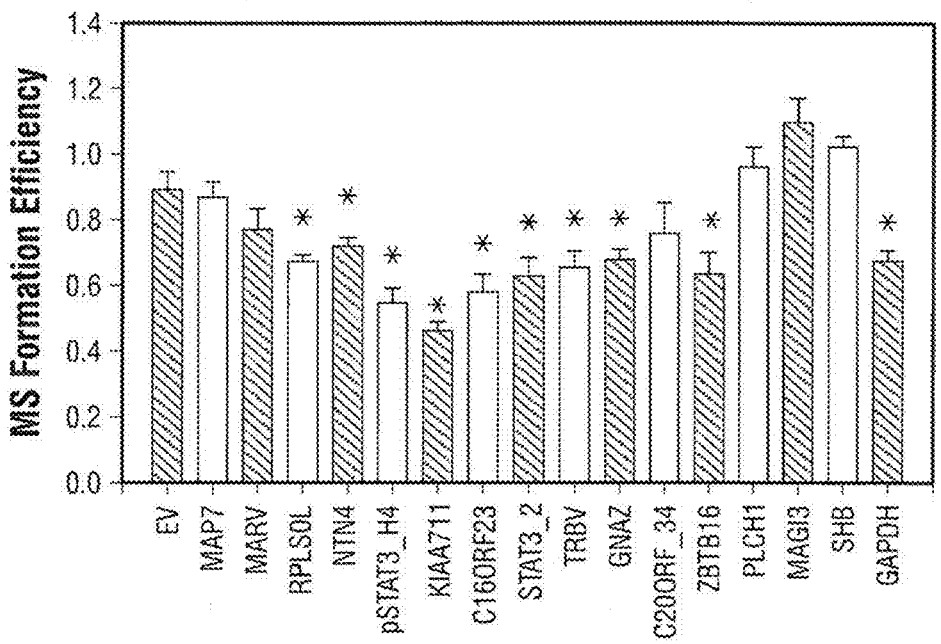
Figure 5A:
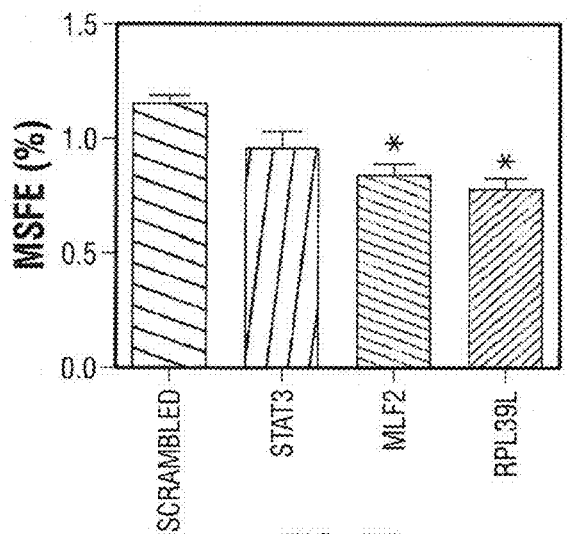
FIG. 5A, FIG. 5B, and FIG. 5C show nanoparticle-encapsulated siRNA targeting the same sequence as the lentiviral vector. Results obtained for two targets, RPL39L and MLF2, are depicted both in vitro, and in vivo.
Figure 5B:
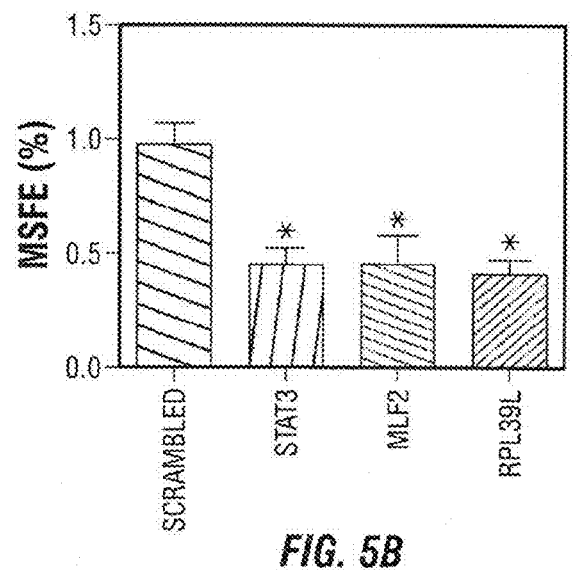
Figure 5C:
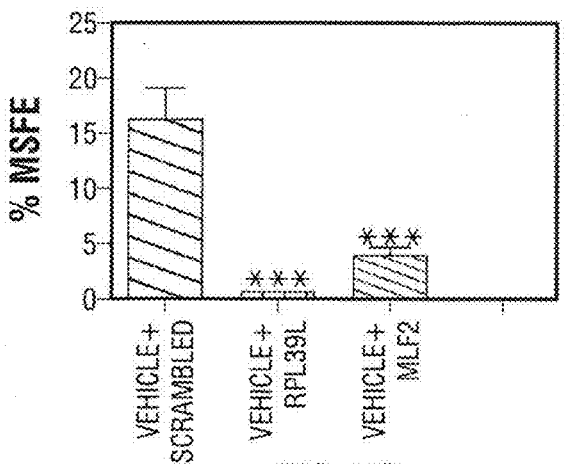

SCID/Beige mice were inoculated with BCM-2665A human primary tumor tissues. After tumors reached 1 cm³ in size, the tumor mice were treated with 20 mg/kg docetaxel. Significant inhibition of tumor growth was observed in the next 14 days (FIG. 4B, left panel). The residual tumor tissues were collected at the end of the experiment, treated with collagenase, and single cells were stained with Aldefluor® reagent (ALDF). Positive staining by ALDF is one of the characteristic markers for TIC. The percentage of ALDF-positive cells was higher in the docetaxel-treated tumor, than in the control samples.

MDS-Delivered siRNA Nanotherapeutics Targeting Therapy-Resistant TICs.

To develop siRNA nanotherapeutics targeting TIC, studies have been conducted to confirm the essential roles of the candidate TIC genes. Exemplary siRNA oligonucleotides specific for STAT3, MFL2, and RPL39L were formulated into nanoliposomes, which were then loaded into porous silicon MSV particles. For in vitro assay, BT549 and SUM159 cells were incubated with MSV/siRNA, and primary and secondary MSFE was measured. Knockdown of MFL2 and RPL39L resulted in significant reduction of primary and secondary MSFE with both cell lines. For in vivo assessment, SCID/Beige mice were inoculated with SUM159 tumor, and treated with MDS/siRNA delivered by tail vein injection. Cells were then isolated from tumor mice 3 weeks later, and MSFE was measured. Dramatic reduction of MSFE was observed in mice treated with siRNA oligo-nucleotides specific to MFL2 and RPL39L. These studies indicate that 1) MDS/siRNA could successfully be delivered to tumor tissues effectively in vivo, 2) uptake of MDS/siRNA by TIC was efficient, and 3) MFL2 and RPL39L were essential genes for TIC.

Elimination of TICs by MDS-Delivered siRNA in Combination with Docetaxel.

In a pilot study (n=3), SCID/Beige mice carrying the BCM-2665A human xenograft tumor were treated with MDS/siRNA and the chemotherapy drug, docetaxel. The mice were sacrificed 2 weeks after treatment, and tumors were collected and processed for mammosphere formation assay and ALDF staining. Treatment with either MDS/

RPL39L or MDS/MLF2 resulted in reduction of ALDF-positive cells. Moreover, treatment with Docetaxel and MDS/RPL39L eliminated more ALDF-positive cells than single treatment with either reagent, indicating the combination treatment had a more profound effect on TICs.

Targeting and Delivery of shRNAs Against TICs Using Liposomes and Multistage Particles.

Porous silicon particles have been developed as an exemplary carrier to deliver nanotherapeutics, and their efficacy on tumor treatment has been demonstrated using mouse cancer models. The TIC targeting siRNAs of the present invention may be delivered to mammalian cells using one or more of these multistage particles (both in vitro and in vivo). Results indicate that the human-tumor-in-mouse models can replicate the TIC phenotype in human patients when treated with chemotherapy drugs, and mammosphere formation of TIC can be inhibited by MDS delivery of one or more of the identified siRNA oligonucleotides that have been shown to specifically target key TIC genes.

Knockdown of Gene Expression by MDS/siRNA In Vitro.

BT549 and SUM159 cells are cultured as attached cells. MDS carrying liposomal scramble siRNA or one or more gene-specific siRNA oligonucleotides are then added into cell culture at a conventional ratio (e.g. 100 particles per cell). Cells are then harvested 3 days later, and expression of the target genes examined by Western blot analysis. Cells are then stained with Annexin V, and separated by FACS analysis for signs of cellular apoptosis.

Assessment of TIC Phenotypes In Vitro.

SUM159 & BT549 cells are grown in low-attachment dishes to form mammospheres. MDS carrying liposomal scramble siRNA or gene-specific siRNA oligonucleotides may are into cell culture at a conventional ratio (e.g., 100 particles per cell). The number of primary mammospheres is then counted 4 days later, and the mammospheres are digested and split into two parts, from which equal numbers of cells are then cultured again in low-attachment dishes to form secondary mammospheres. The number of mammospheres is then counted 4 days later, and cells used for $CD44^+/CD24^{-/low}$ and ALDH1 analysis by conventional methods such as FACS.

Xenograft Treatment Assays:

Two triple-negative cell lines (including SUM159 and BCM2665A, which is a human-cancer-in-mouse xenograft line) may be used in such assays. Short-term (2-week) studies are performed to assess the effect of knockdown of gene expression on TIC viability, and tumor fragments of human xenografts may be transplanted into the cleared fat pad (right abdominal) of fifty 3- to 4-weeks-old SCID/Beige mice. When tumors reach 150-300 mm³, mice may be equally distributed according to size into seven groups (n=10) and treated with suitable test and control samples. An exemplary test regimen includes: 1) MDS/control siRNA (15 mg siRNA, i.v.), 2) MDS/MFL2 siRNA (15 mg siRNA, i.v.), 3) MDS/RPL39L siRNA (15 mg siRNA, i.v.), 4) docetaxel (20 mg/kg, ip.), 5) MDS/control siRNA plus docetaxel, 6) MDS/MFL2 siRNA plus docetaxel, and 7) MDS/RPL39L siRNA plus docetaxel. Total body weight and tumor volumes may be measured at appropriate (e.g., twice weekly) intervals. Mice are sacrificed after treatment (e.g., after 14 days), and tumors collected and examined using one or more conventional methods, including, for example, biomarker analysis.

Pathological Analysts:

Major organs may be collected at the end of the study, embedded into paraffin blocks, processed for H&E staining, or one or more additional assays such as TUNEL assay for apoptosis, Ki67 staining for cell proliferation, and the like. The presence of tumors was examined microscopically.

Expression Analysis of Target Genes and Assessment of TIC Biomarkers:

Knockdown of gene expression in tumors may be monitored by conventional methods, including, for example, quantitative RT-PCR. Alteration in frequency of TIC markers ($CD44^+/CD24^{-/low}$ and aldehyde dehydrogenase, ALDH1) is determined by flow cytometry (Li et al., 2008), and MSFE assayed as described herein.

Long-Term Treatment of siRNA to Assess Therapeutic Efficacy and Tumor Recurrence.

Xenograft Treatment Assays:

To generate enough cells for subsequent functional analysis, tumor fragments from three human breast cancer xenograft lines may be transplanted into the cleared fat pad (right abdominal) of seventy 3 to 4-week-old SCID/Beige mice. When tumors reach 150-300 mm³, mice are equally distributed according to size into 1 of 7 treatment groups (n=10) including: 1) MDS/control siRNA (15 mg siRNA biweekly, i.v.), 2) MDS/MFL2 siRNA (15 mg siRNA biweekly, i.v.), 3) MDS/RPL39L siRNA (15 mg siRNA biweekly, i.v.), 4) docetaxel (33 mg/kg weekly, i.p.), 5) MDS/control siRNA plus docetaxel, 6) MDS/MFL2 siRNA plus docetaxel, 7) MDS/RPL39L siRNA plus docetaxel. Total body weight and tumor volume is measured twice weekly. Mice are treated for 6 weeks unless maximum response has been reached during treatment. Maximum response is defined as complete disappearance of tumor, or no further decrease in tumor size after two cycles of treatment in any of the docetaxel combination groups. Mice are monitored twice-weekly after treatment has been stopped to determine recurrence in tumor volume and body weight. Outcomes of interest include time to treatment failure (defined as the time from randomization to tripling of tumor size), time to complete response (defined as time from randomization to complete disappearance of tumor), and time to relapse (defined as time from maximum response to greater than baseline). Data are analyzed using conventional survival analysis methods.

Statistical Considerations:

After log transformation, tumor growth (or regression) is analyzed using mixed general linear models. With nine mice per treatment group, this provides at least 90% power ($\alpha=5\%$) to detect standardized effect sizes of 0.75 or greater between any two treatment groups. For a 'representative' xenograft model, this translates to about 30% smaller tumors in an experimental group compared to a referent (i.e. combination vs. single agent).

Example 3

RPL39 and MLF2 Promote Tumor Initiation and Lung Metastasis

Triple negative breast cancer is the most aggressive and lethal form of cancer with no targeted therapy. To understand the mechanism of survival of these cancers, a gene signature was identified for breast cancer stem cells (BCSC) derived from patient biopsies. On selective shRNA knockdown of these genes, RPL39 and MLF2 were identified as the top candidates that affect BCSC self-renewal. Selective siRNA knockdown of RPL39 and MLF2 in human cancer xenografts, showed reduced tumor volume and lung metastases with a concomitant decrease in BCSC markers. Next generation RNA-seq confirmed mutations in RPL39 and MLF2 in 50% of lung metastases from breast cancer patients. Additionally, in vitro and in vivo siRNA knockdown of RPL39 and MLF2 showed decrease in nitric oxide synthase suggesting that the two novel cancer genes are driven by this pathway. These results lay the foundation for developing new therapies for these cancers with poor prognosis.

Triple negative breast cancer (TNBC) is defined by the lack of estrogen receptor (ER), progesterone receptor (PR) and human epidermal growth factor receptor 2 (HER2). TNBCs represent 15-20% of all breast cancers, and are associated with the worst outcomes and a higher likelihood of relapse (Haffty et al., 2006). Large-scale sequencing analyses of solid cancers have identified extensive heterogeneity within individual tumors (Gerlinger et al., 2012). This intratumoral heterogeneity (Campbell et al., 2008; Campbell et al., 2010; Shah et al., 2002) may contribute to treatment resistance and treatment failure. Recent studies indicate that such intratumoral heterogeneity is associated with heterogeneous protein function, which may foster tumor adaptation and therapeutic failure through Darwinian selection.

Cancer stem cells are identified as a sub-population of cells, responsible for tumor initiation and recurrence (Al-Hajj et al., 2003; Lapidot et al., 1994; Li et al., 2008: Singh et al., 2003; Smalley and Ashworth. 2003; Stingl and Caldas, 2007). Recently, three groups have independently provided functional evidence for the presence of cancer stem cells by lineage tracing experiments in glioblastomas, squamous skin tumors, and intestinal adenomas, suggesting the hierarchical nature of cancer (Chen et al., 2012, Drissens et al., 2012, Schepers et al., 2012). These observations are consistent with subpopulations of cancer stem cells (CSCs), within the bulk primary tumor that are resistant to conventional therapies through different adaptive mechanisms (Jones et al., 2004; Li et al., 2008; Creighton et al., 2010), with the potential for self-renewal and metastases. Consistent with these observations, a very few studies have determined the genetic profile of the cells that escape the primary cancer and evolve in distant metastatic sites (Gerlinger et al. 2012).

Breast cancer stem cells have been postulated to have an epithelial-mesenchymal transition (EMT) like phenotype (Mani et al., 2008). EMT induces metastatic properties of invasion, migration and dissemination in cancer cells (Polyak and Weinberg, 2009). Establishment of metastatic lesions following dissemination requires a permissive microenvironment in the target organs (Fidler, 2003; Gupta and Massague, 2006). The observation that the breast cancer cells in metastatic lesions have an epithelial phenotype has led to the speculation that the disseminated cancer cells undergo mesenchymal to epithelial transition (MET) that would favor metastasis (Chaffer et al., 2007; Hugo et al., 2007). Recently, it was reported that paracrine and autocrine signals induce and maintain mesenchymal and stem cells states in the breast (Scheel et al., 2011). These studies suggest an important role for EMT and MET in cancer stem cells and metastasis.

Thus, novel therapies are required to target breast cancer stem cells (BCSC), in order to prevent relapse and metastasis of breast cancer. It has been difficult to screen for targets of cancer stem cells of solid tumors because of their instability in cell culture (Fillmore and Kuperwasser, 2008). Previous screens have overcome the problem by the use of HMLER (human mammary epithelial cells transformed with V12H-Ras oncogene) to induce epithelial to mesenchymal transition and are thus enriched for BCSCs. This chemical library based approach has identified potential candidates that selectively target BCSCs as compared to chemotherapy (Gupta et al., 2009).

In order to discover new targets that are functionally integral in BCSC self-renewal and potentially in metastasis, selective lentiviral shRNA knockdown of 493 BCSC genes (Creighton et al., 2008) identified two novel genes (RPL39 and MFL2), which were relatively unknown in terms of their significance in cancer.

The development of treatments that target BCSCs has been highly challenging. In this example, a multistage delivery (MSV) strategy, consisting of biodegradable mesoporous silicon, together with nanoparticles (e.g., liposomes and micelles) incorporated with therapeutic agents such as siRNA has been used to demonstrate success in overcoming biological barriers, maximizing site-specific localization and release of therapeutics at the target tumor (Tanaka et al., 2010). In this example, the identification and characterization of two novel cancer genes essential in self-renewal and metastasis are described. The effect of silencing of these genes on primary human triple negative breast cancer stem cells and metastasis, and their mechanisms of action are also disclosed.

Experimental Procedures

Selective shRNA Knockdown of Differentially Expressed Genes.

Previously, a breast cancer stem cell signature was identified comprising 493 statistically significant differentially expressed genes (Creighton et al., 2009). The biological significance of this gene set was confirmed by conducting shRNA-based gene knockdown, and correlating the selective knockdown of target genes using mammosphere-forming efficiency (MSFE), an in vitro assay for self-renewal. As described in the previous examples, a library of shRNAs targeting the entire human genome (Open Biosystems, MA, USA) was used to create a sub-library of shRNAs against the differentially expressed genes in the tumorigenic signature. Using these genes along with appropriate control shRNAs, a total of 1124 shRNAs (~2-3 shRNA per gene) were tagged with green fluorescent protein, and encoded in pGIPZ vector, and then arrayed on to 13×96-well plates. These shRNAs were packaged into lentiviral particles using a second-generation lentiviral packaging system (Thermo-Fischer, USA) in 293T cells plated in 96-well plates. The supernatant was then harvested for transduction and expression in a wide range of cell types. Specifically, lentiviruses were collected 3 days after transfection, frozen immediately at −80° C., then thawed for transducing two different breast cancer cell lines SUM159 (Asterand, Detroit, Mich., USA) and BT549 (American Type Culture Collection, Manassas, Va., USA) with eight biological replicates. The cells were plated in 13×96-well ultra-low attachment plates at 2000 cells/well with one shRNA being transduced per well, using the Biomek 3000 automated workstation (Beckman Coulter, Brea, Calif. USA), to ensure reproducibility and accuracy. The lentiviral transduction rate (~80-90%) in the cell lines was evaluated by quantification of fluorescence from the GFP tag in the pGIPZ vector, using a fluorescence microscope. The MSFE was then assessed in a high-throughput screening approach for all 493 genes. The results were compared with negative (empty vector) and positive control (gamma secretase inhibitor, against Notch pathway, MRK-003, Merck, Inc.) by the method of Grudzien et al. (2010).

Secondary Confirmation of Candidate Gene Targets.

The top 15 candidates from the primary screen were analyzed by MSFE assay in a 24-well plate with n=12 replicates using a known concentration of virus (MOI of 10) to identify the most efficient shRNAs. Briefly, 5000 cells/well were plated in mammosphere media, and lentivirally-packaged shRNA at MOI of 10 was added to the cells. The MSFE was calculated by counting the cells on Day 3 using Gelcount (Oxford Optronix, Oxford, UK), in order to select and confirm the most significant genes for further in vivo xenograft studies.

In Vitro Nanoliposomes Packaged siRNA Studies.

The siRNA sequences of two candidate genes RPL39 and MLF2 were packaged in nanoliposomes and the effects on MSFE determined in vitro, as described above, using packaged siRNA instead of lentiviral shRNA.

In Vitro Overexpression Studies.

Effect on MSFE and Proliferation:

Following transient overexpression of MLF2 and RPL39 in three different triple negative cell lines (SUM159, MDAMB231, and BT549), mammosphere formation and proliferation assays were performed. Briefly, for MSFE assay 5000 cells/well were transfected in suspension using lipofectamine reagent (Invitrogen, Corp., Carlsbad, Calif., USA). MSFE was determined by Gelcount (Oxford Optronix, Oxford, UK) after 72 hrs. Similarly, proliferation assays were performed in a 96-well plate with 100 cells/well in these triple-negative cell lines. Proliferation assays were performed using Wst-1 reagent 72-hrs' post-transfection.

Wound Healing Assay.

Plasmids overexpressing RPL39 and MLF2 genes were transfected at 2 g/mL concentration using reverse transfection protocol for lipofectamine. Transfected cells were allowed to attach in a monolayer for 24 hrs. followed by a scratch using a 1-mL pipette tip. The wound was allowed to heal for 24 hrs and images were taken using bright field microscope with attached camera. Data was then quantified using ImageJ software (available from the National Institutes of Health).

EMT/MET Analysis.

RPL39 and MLF2 were overexpressed in three cell lines (MDAMB231, BT549 and SUM159). Plasmids overexpressing RPL39 and MLF2 genes were transfected at 2 µg/mL concentration using reverse transfection protocol for lipofectamine and plated in (i) chamber slides (n=4/group) and (ii) 6-well plates (n=3/group). The cells in the chamber slides were allowed to grow for 48 hrs, followed by fixation using 50% methanol/acetone at −20° C. for 20 min. These cells were stained with hematoxylin and eosin and analyzed for changes in morphology. The cells in 6-well plates were also allowed to grow for 48 hrs, and RNA was extracted from them using the Qiagen RNA mini-kit (Qiagen, Inc., Valencia, Calif., USA). cDNA was prepared using iscript kit (Bio-Rad Inc, Hercules, Calif.). The cDNA was analyzed for gene expression of MET genes (SNAIL, N-cadherin, vimentin, fibronectin-1, occludin) using real time quantitative PCR using standard curve method. The PCR was run using SYBR Green assay buffer (Bio-Rad Inc, Hercules, Calif., USA) on an AB17900 analyzer (Applied Biosystems. Inc.).

In Vivo Xenograft Studies.

Long-term in vivo treatment efficacy studies: three million cells MDAMB231 cancer cells, which grow primary as well as metastatic tumors, were injected in the mammary fat pad of SCID-Beige mice and allowed them to grow to 150-300 mm³ tumors, and randomized them into 6 groups: (1) vehicle+scrambled siRNA. (2) vehicle+MLF2 siRNA. (3) vehicle+RPL39 siRNA, (4) docetaxel (20 mg/kg)+ scrambled siRNA, (5) docetaxel (20 mg/kg)+MLF2 siRNA, and (6) docetaxel (20 mg/kg)+RPL39 siRNA. Each injection was loaded with 15 µg of siRNA per animal. These groups received three cycles of treatment every 14 days apart starting at Day 0, and cationic liposome packaged siRNA was administered through tail vein injection thrice weekly.

Short-Term In Vivo Treatment Studies for Effect on Stem Cell Markers.

The effect of MLF2 and RPL39 using siRNA packaged in multistage nanoparticles in two different triple negative models were studied. SUM159 and a patient-derived human cancer xenograft (BCM2665) from a primary human breast cancer transplanted in SCID-Beige mice, the test group had 54 mice per xenograft line, and 9 mice per treatment arm. When tumor sizes reached 150 to 300 mm³, mice were divided into six groups: (1) vehicle-treated, (2) chemotherapy on day 0 with one dose of docetaxel 20 mg/kg by intraperitoneal (i.p.) injection. (3) siRNA against MLF2 packaged in nanoparticles (single injection intravenous (i.v.) on Day 1), (4) combination treatment with docetaxel (20 mg/kg i.p. on Day 1) and siRNA against MLF2 (single injection i.v. on Day 1), (5) siRNA against RPL39 packaged in nanoparticles (single injection i.v. on Day 1), and (6) combination treatment with docetaxel (20 mg/kg i.p. on Day 1) and siRNA against inhibitor MLF2 (single injection iv. on Day 1). The same dose (15 µg siRNA) was used in all experiments. Animals were sacrificed on Day 14. The tumors were harvested and analyzed for downstream effects on BCSC self-renewal using FACS analysis, and MSFE.

In Vivo Treatment Studies for Effect on Lung Metastasis.

3 million cells MDAMB231 cancer cells, stably transfected with luciferase, were injected in the mammary fat pad of SCID-beige mice and were randomized into 3 groups: (1) vehicle+scrambled siRNA, (2) vehicle+MLF2 siRNA, and (3) vehicle+RPL39 siRNA, and treated with siRNA packaged liposomes twice weekly for 6 weeks. The mice were injected with D-luciferin every week for 6 weeks to determine lung metastases using IVIS imaging (Perkin Elmer). The primary tumors were removed by week 5 to continue this study without increasing the primary tumor burden to 10% of body weight.

FACS Analysis and Mammosphere Formation Efficiency (MSFE).

The fraction of BCSCs in the xenograft tumors from the six treatment groups were processed by mincing and digesting the tumors using collagenase type III, for 3 hrs at 37° C. in order to dissociate the tumors into single cells. Changes in CD44+/CD24/Lin− and Aldefluor® were analyzed as described previously (Li et al., 2008). Briefly, cells were stained with primary antibodies antiCD44 labeled APC (dilution 1:10. BD Biosciences), anti-CD24-labeled FITC (dilution 1:10, BD Biosciences), and additionally with H2KD-labeled PE to eliminate all mouse, lineage-positive cells. The cells were incubated in HBSS (Hanks Balanced Salt Solution, GIBCO) for 15 min on ice with 2% FBS for the antibodies and 45 min for Aldefluor® reagent. Following incubation, cells were washed once with HBSS and re-suspended in HBSS supplemented with 2% FBS. Protease inhibitor (PI) was added to the cells for live/dead gating prior to FACS analysis.

Mammosphere formation efficiency, the in vitro assay for stem cell self-renewal, was performed as described previously (Dontu et al., 2003; Dontu et al., 2005; Li et al., 2008). Single cells were plated in ultra-low attachment plates (Corning, Acton, Mass., USA) at the density 40,000 viable cells/mL for BCM2665 in primary culture, and at the density 10,000 viable cells/mL in secondary culture. For mammosphere culture, cells were grown in serum-free mammary epithelial basal medium (MEGM) (Lonza, Inc.) supplemented with B27 (Invitrogen), 20 ng/mL EGF (BD Biosciences), and 1% heparin (Sigma Chemical Co.) in a humidified incubator (10% $CO_2$: 95% air, 37° C. for 14 days, as previously described (Li et al., 2008).

Western Blot Analysis.

In order to confirm the pathways involved in BCSC targeting, western blot analysis was conducted with siRNA knockdown and overexpression of RPL39 and MLF2 in three breast cancer cell lines (SUM159, BT549 and MDAMB231). Briefly, 30 µg of whole cell extracts were quantified and run on a 4-20% gel for 1 hr, and transferred onto nitrocellulose membranes. The primary antibodies were incubated overnight at the following dilutions eNOS (1:500), nNOS (1:500), and iNOS (1:1000) (Millipore, Bellerica, Mass., USA) followed by one-hour secondary antibody incubation, and development using chemiluminescence.

Evaluation and Normalization of Affymetrix Gene Chip Data.

The array data were evaluated using the commercial software suite, Partek® Genomics Suite® (St. Louis, Mo., USA). Specifically, data were normalized by using the RMA (robust multichip averaging) method. Gene expression levels were analyzed on a logarithmic scale. ANOVA was used to identify differentially expressed genes. Genes with p-value less than 0.05 in each comparison were selected for further functional and pathway analyses by Ingenuity® Pathway Analysis (IPA®) tools (Redwood City, Calif., USA).

RNA-Seq of Breast Cancer Patient Lung Metastases.

Briefly, total RNA was extracted from formalin-fixed paraffin-embedded (FFPE) tissue using EZNA FFPE RNA kit (Omega Biotek, Norcross, Ga., USA), and the integrity and purity of total RNA were assessed using an Agilent Bioanalyzer 2100. Then, 5 µg of total RNA was subjected to rRNA depletion using the RiboZero Human/Mouse/Rat kit (Epicenter Biotechnologies, Madison, Wis., USA) and cDNA was generated from the depleted RNA using the NEBNext mRNA Sample Prep kit (New England Biolabs). cDNA was profiled using Agilent Bioanalyzer, and subjected to Illumina library preparation using NEBNext reagents (New England Biolabs). The quality and quantity and the size distribution of the Illumina libraries were determined using an Agilent Bioanalyzer 2100. The libraries were then submitted for Illumina HiSeq2000 sequencing, according to standard procedures. Paired-end 90 or 100-nucleotide (nt) reads were generated and subjected to data analysis using the platform provided by DNAnexus (DNAnexus, Inc, Mountain View, Calif., USA). Reads were mapped to hg19 using TopHat version 2.0.4. Tophat provided options to allow 3 transcriptome mismatches, 10 genome read mismatches, and 10 read mismatches, and BowTie2 2.0.0-β7 options were set to "--b2-N 1--b2-D 20--b2-R 3--b2-mp 3,1". Post alignment, BAM tiles were run using Contraster analysis (Five3 Genomics LLC, Santa Cruz, Calif., USA) in Bam-Single mode for variant detection. In short, this method uses criteria including base quality, neighborhood quality, mapping quality, and duplicates to detect genotypes throughout the BAM file. Possible genotypes are assessed using the MAQ error model (Li et al., 2008), and these genotypes are fed to a Bayesian model incorporating a prior probability on the reference and the heterozygous rate of the human genome. The genotype with the highest likelihood is selected, and multiple metrics are computed to assess the quality and overall confidence of that genotype. All possible variants for each sample were extracted from the resulting variant call format file (VCF).

SIFT (Sorting Intolerant from Tolerant) Analysis for Mutation.

Human Protein analysis was performed using Protein Ensemble ENSP ID for MLF2 (ENSP 00000203630) and RPL39 (ENSP 00000355315) and the annotated RNA-seq amino acid substitutions. SIFT analysis identified two missense mutations in each gene, MLF2 (DI2H and R158W) and RPL39 (A14V and G50S), that encode proteins with amino acid substitutions predicted to be functionally damaging and potentially disease causing.

Confirmation of Mutations in RPL39 and MLF2 by Allele-Specific PCR Analysis.

The mutations identified using RNA-Seq were confirmed using competitive allele-specific PCR kit (Applied Biosystems, Carlsbad, Calif., USA). Briefly, the RNA prepared for RNA-seq from patient lung metastasis was used to prepare cDNA using the iScript™ cDNA synthesis kit (Bio-Rad, Inc., Hercules, Calif., USA). This cDNA was then analyzed for the presence of wild type or mutant allele using a custom-designed assay (Applied Biosystems).

Statistical Analysis.

In the shRNA knockdown experiments, the mean and standard deviation of all measurements from every replicated experiment of each plate were estimated. The Z-score was calculated by subtracting each individual value from the mean values of the plate and dividing the difference by standard deviation. One sample t-test was then utilized to test whether the mean score of each gene significantly differs from zero. Different treatment groups were compared by one-way ANOVA to determine statistical significance in the confirmatory shRNA, nanoliposome siRNA, and tumor volume fold-change experiments. This was followed by Tukey analysis for a pairwise comparison of the different treatment groups. In the tumor recurrence studies, events were defined as first appearance of tumor >50 mm$^3$ after completion of treatment. Time to recurrence was derived by the Kaplan-Meier method, with differences compared using the generalized Mann-Whitney-Wilcoxon rank-sum test.

Results

Identification of siRNA Targets for Tumor Initiating Cells of Breast Cancer.

Figure 6A:
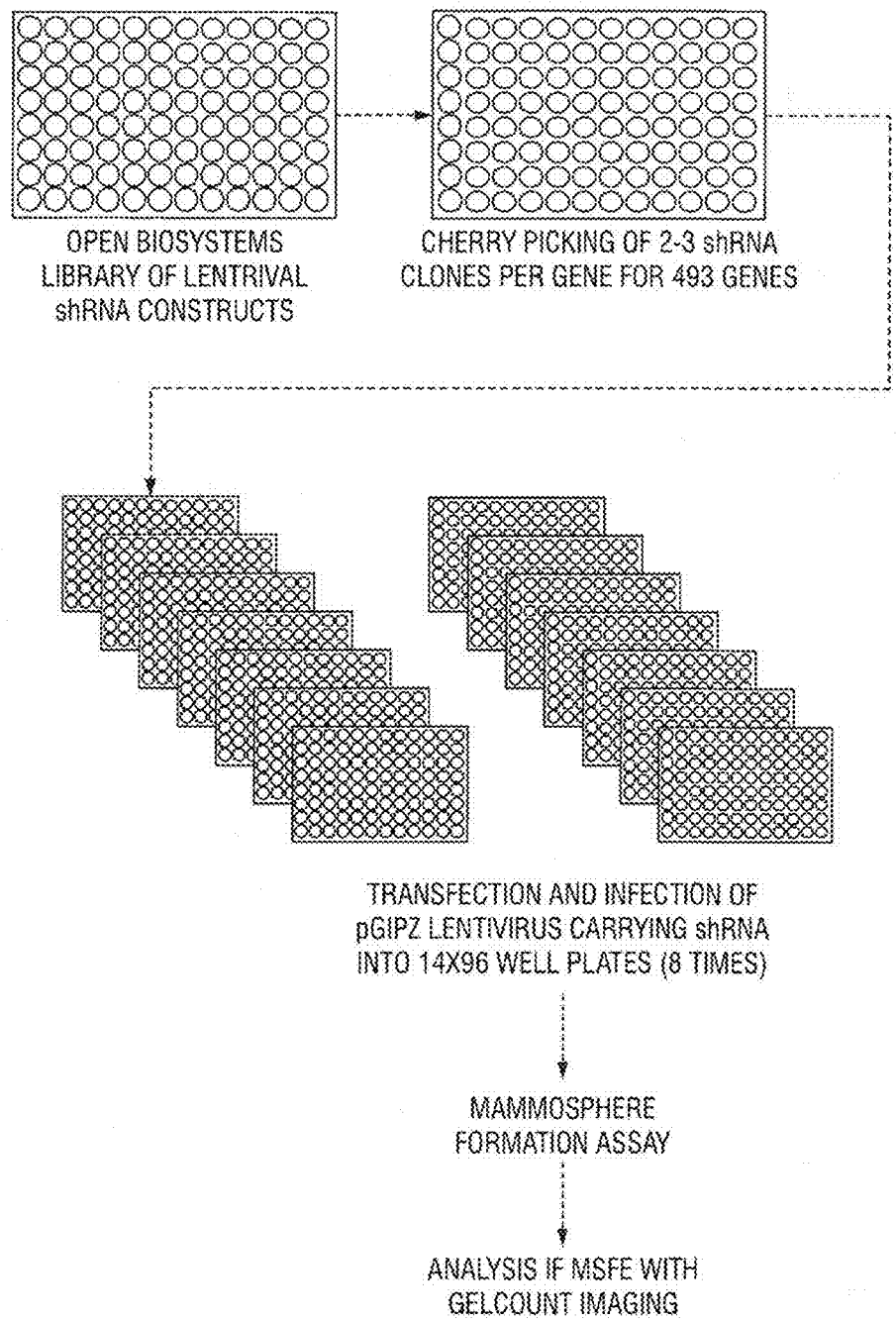
FIG. 6A, FIG. 6B and FIG. 6C show the identification of shRNA targets for breast cancer stem cells in TNBC.
Figure 6C:
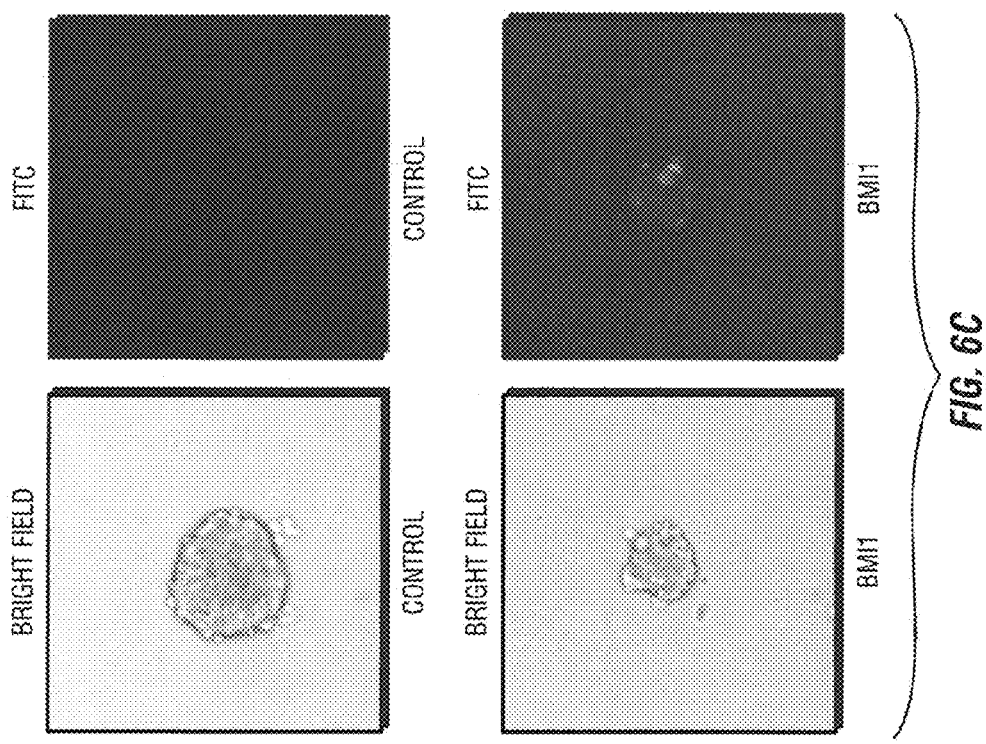
Figure 6B:
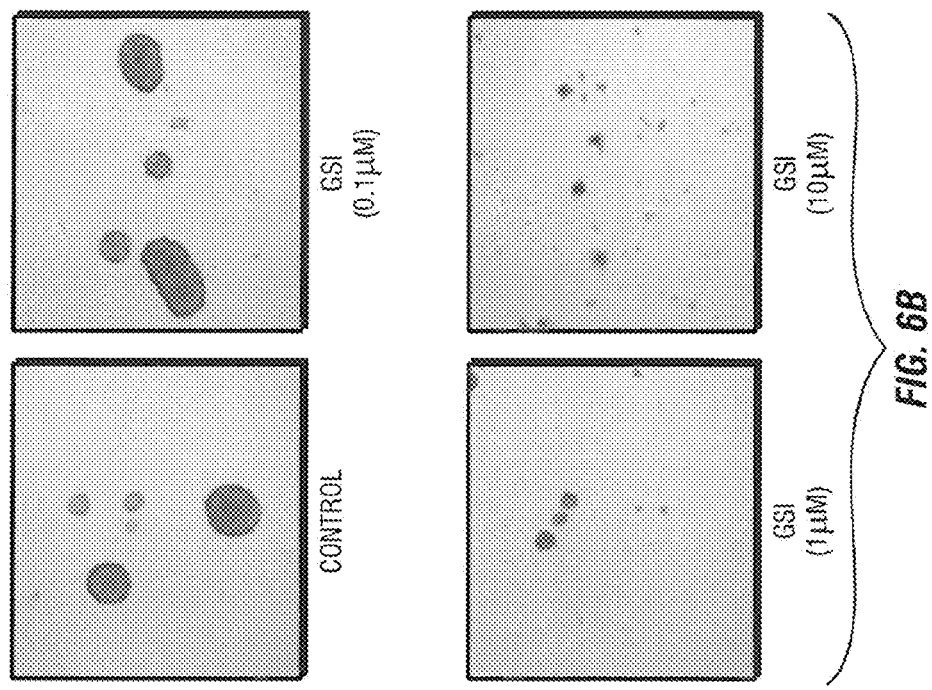

The shRNA library encompassing all 493 genes with 2-3 shRNAs per gene, along with empty vector and control siRNAs was converted to viral particles, using the pGIPZ lentiviral vector. Two triple-negative, breast-cancer cell lines, SUM159 and BT549, were treated with the viral particles, and allowed to grow in mammosphere (MS) media for 72 hrs prior to counting. The MS data was analyzed using Gelcount® (Oxford Optronix, UK), and statistical analysis performed using Mann-Whitney-Wilcoxon rank-sum test (FIG. 6A). The Notch pathway inhibitor MRK-003 (a γ-secretase inhibitor against Notch pathway. Merck, Inc.) dramatically reduced MS formation at 10 µM concentration, as known positive control (FIG. 6B). The number of GFP positive cells were counted, using shRNA directed at Bmi-1 as a transduction efficiency control, and determined the efficiency to be 85-90% (FIG. 6C, a representative figure for transduction). This was used to shortlist a set of target genes for breast cancer stem cells.

Candidate Target Genes.

Figure 7A:
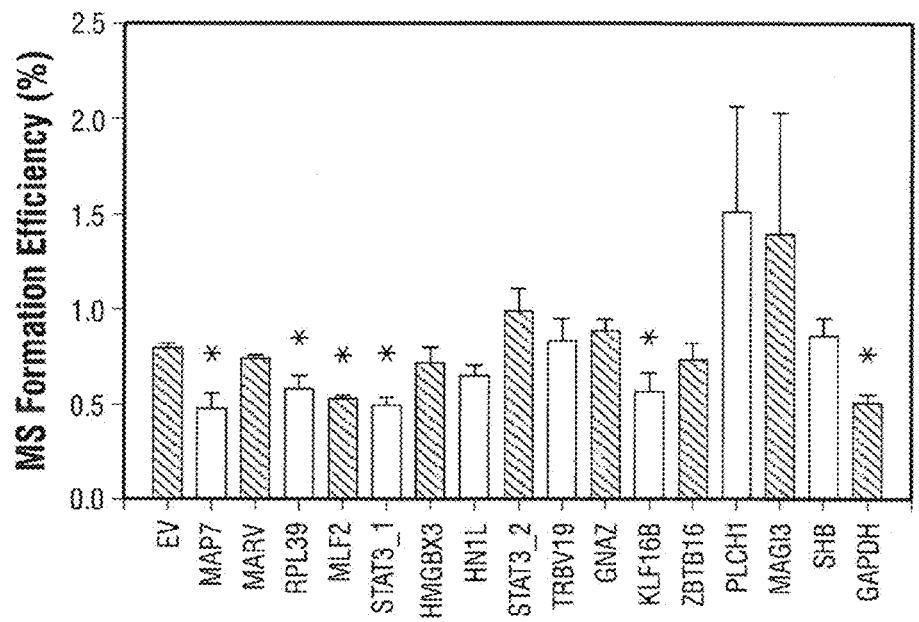
FIG. 7A, FIG. 7B, and FIG. 7C show confirmation of BCSC target genes and comparison of changes in mammosphere formation efficiency.
Figure 7B:
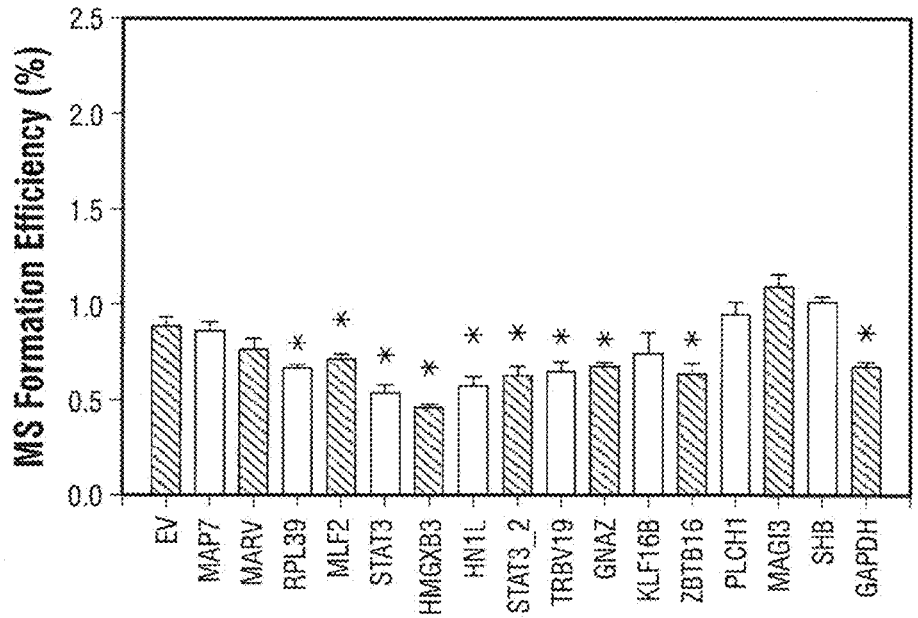
Figure 7C:
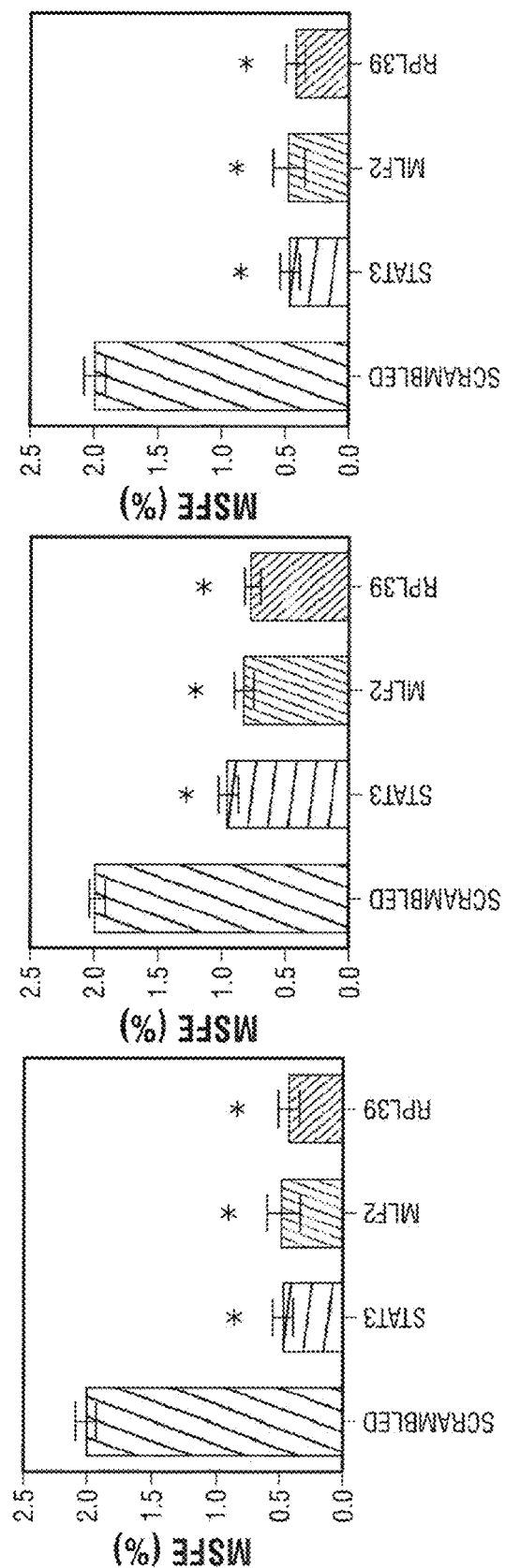

Using Mann-Whitney-Wilcoxon rank-sum test to compare rank scores with positive control GSI to identify the shRNAs that effectively decreased MS formation in one or both cell lines was performed. Only six shRNAs showed significantly reduced expression in both SUM159 and BT549 cell lines (p<0.05) (FIG. 7A). The possibility of eliminating other potential candidates due to high stringency was addressed by lowering the p-value to <0.1, and re-testing shRNAs by a defined low titer of the virus, and thereby expanding the list of genes to 15 candidate genes for further confirmation. The primary screen had been conducted in a 96-well setup with a quantity of virus titer to give multiplicity of infection (MOI) of 30-50. The top fifteen candidate genes were re-screened with MOI of 10 for n=4 replicates, using both SUM159 and BT4549 cell lines. This analysis re-confirmed that 7/15 genes in SUM159 and 9/15 genes in BT549 were efficient in reducing MSFE (FIG. 7B). To develop potential therapeutics, the corresponding siRNA sequences derived from these shRNA clones were identified, and the effects of these siRNAs on MSFE were tested in three cell lines: SUM159, BT549 and MDAMB231. RPL39 and MLF2 siRNA significantly reduced secondary MSFE in all three cell lines (FIG. 7C).

Long-Term In Vivo Xenograft Treatment Studies.

Figure 8A:
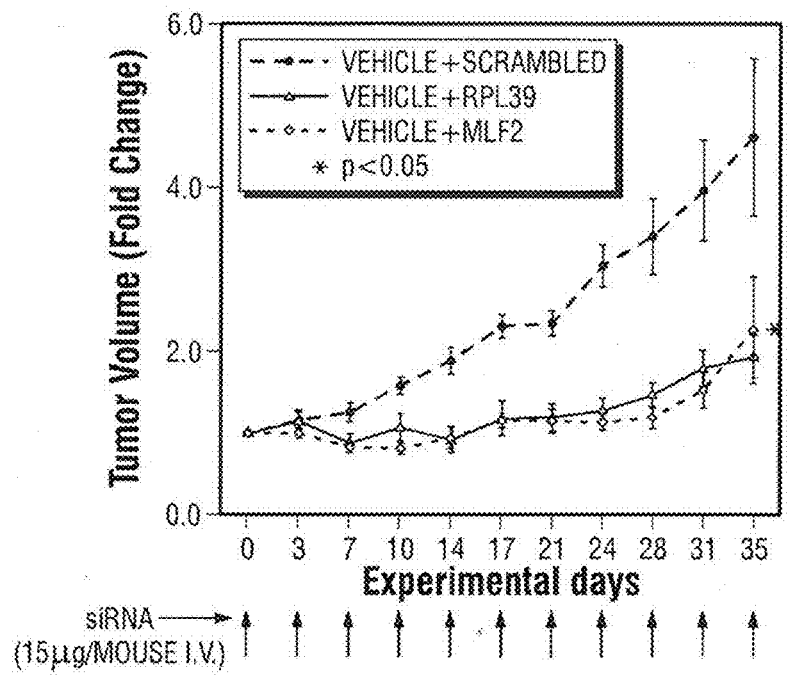
Figure 8B:
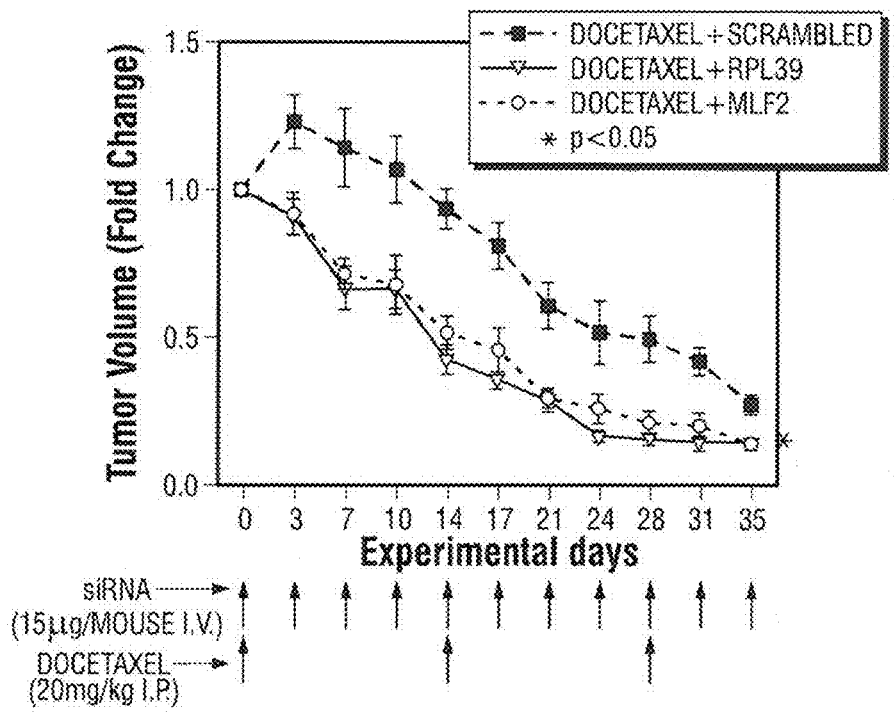
Figure 8C:
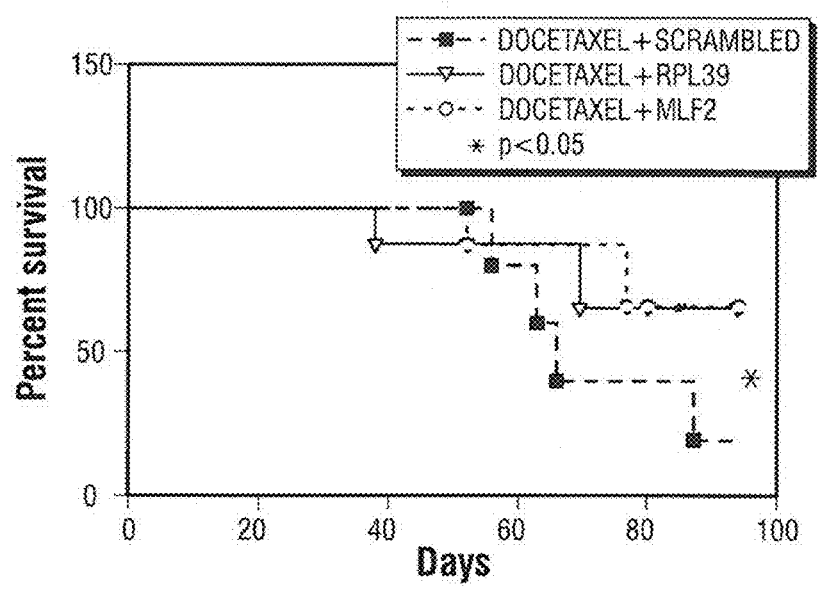
FIG. 8C shows the Kaplan Meir analysis of median survival of mice treated with docetaxel or combination therapy (docetaxel+RPL39/MLF2 siRNA)

Long-term treatment in vivo studies were initiated to measure the efficacy of these siRNAs in MDAMB231 tumor xenografts. Significant reduction in tumor volume was observed in RPL39 and MLF2 treated groups, compared to vehicle treated groups (FIG. 8A) ($p<0.05$. Mann-Whitney-Wilcoxon rank-sum test). Additionally, the combination of RPL39/MLF2 siRNAs and docetaxel significantly reduced tumor volume (FIG. 8B) ($p<0.05$, Mann-Whitney-Wilcoxon rank-sum test). More importantly, the combination of RPL39 or MLF2 siRNA with chemotherapy significantly prolonged median survival over chemotherapy alone ($p<0.05$) (FIG. 8C). This finding demonstrates the usefulness of the disclosed siRNAs as viable therapies for cancers such as that of the human breast.

Short-Term In Vivo Treatment Studies.

Figure 9A:
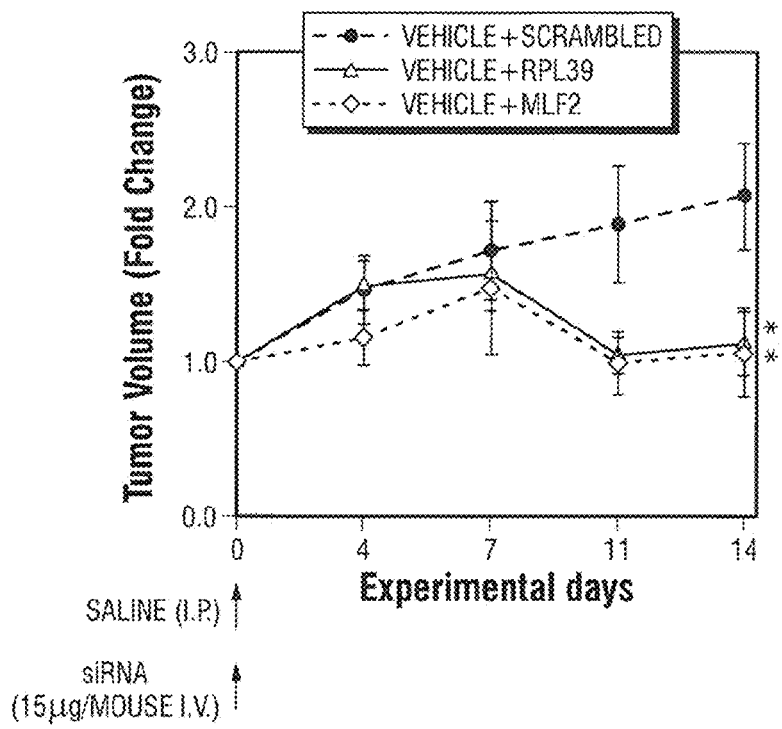
FIG. 9A, FIG. 9B, FIG. 9C, and FIG. 9D show short-term, in vivo treatment in siRNA SUM159 xenografts. Triple-negative breast cancer cell line SUM159 was injected into the mammary fat pad of SCID beige mice (n=9). These tumors were randomized into six groups: 1) vehicle+scrambled siRNA (15 μg, i.v.); 2) vehicle+RPL39 siRNA 15 μg (i.v.); 3) vehicle+MLF2 siRNA (15 μg (i.v.); 4) docetaxel (20 mg/kg, i.p.)+scrambled siRNA 15 μg (i.v.): 5) docetaxel (20 mg/kg, i.p.)+RPL39 siRNA 15 ltg (i.v.), and 6) docetaxel (20 mg/kg, i.p.)+MLF2 siRNA 15 μg (i.v.).
Figure 9B:
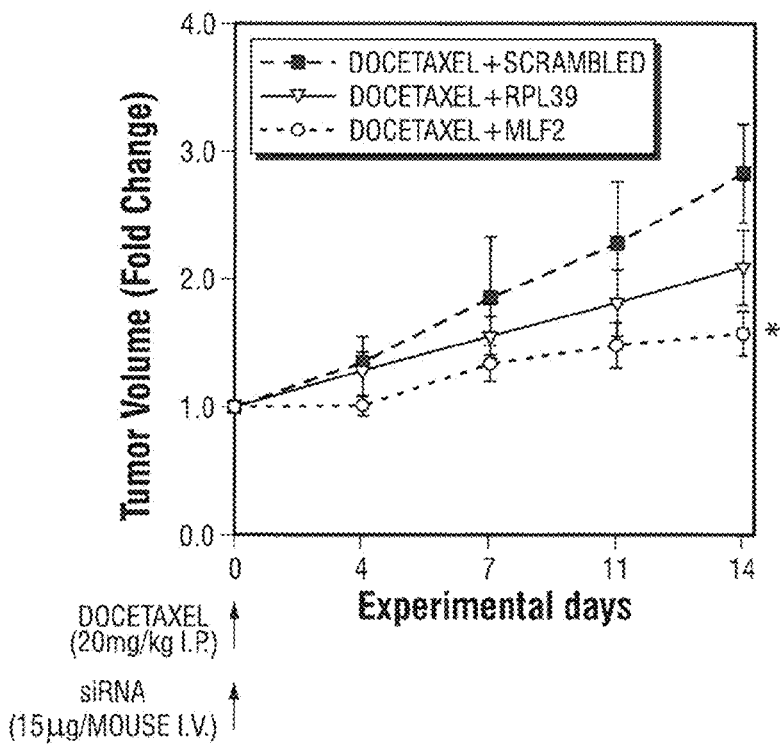
Figure 9C:
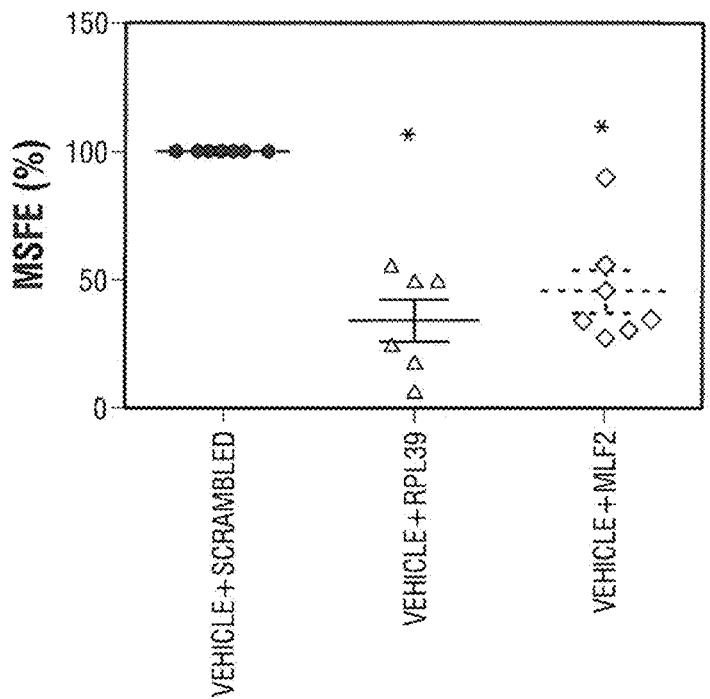
Figure 9D:
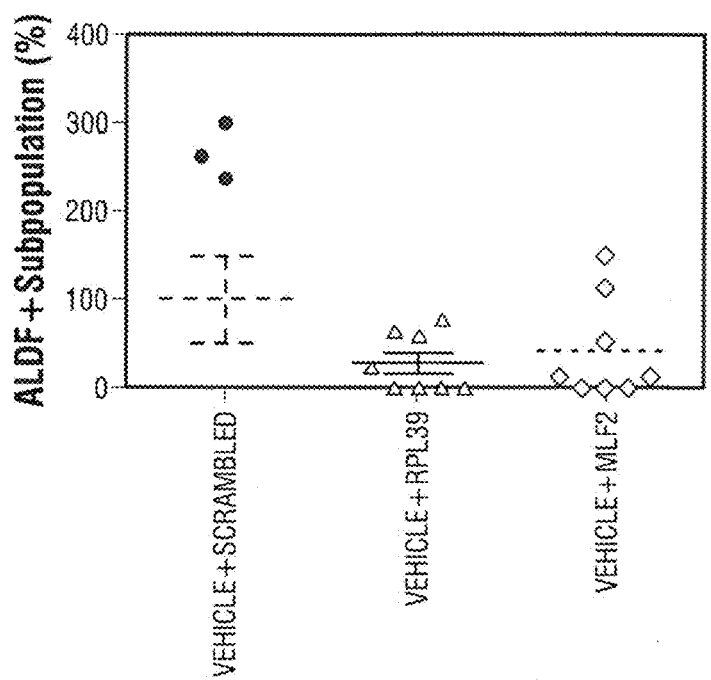
Figure 10A:
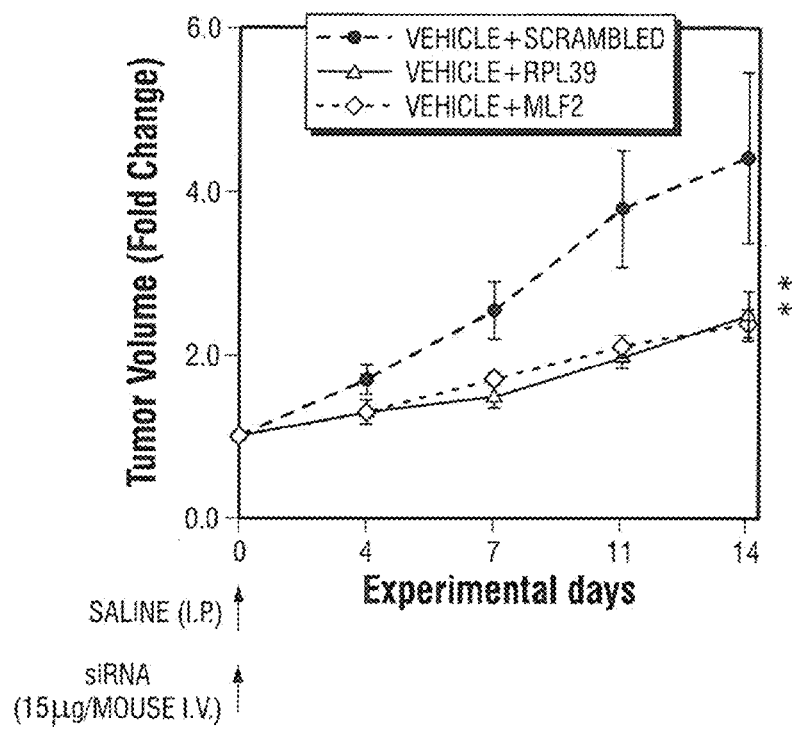
FIG. 10A, FIG. 10B, FIG. 10C, and FIG. 10D illustrate the short-term, in vivo treatment of siRNA in triple-negative, patient-derived human cancer in a murine model xenograft, BCM2665. BCM2665 cells were transplanted into cleared mammary fat pad of SCID beige mice (n=9). These tumors were randomized into the same six groups as stated in the preceding figure, and treated in a manner identical to the SUM159 xenografts.
Figure 10B:
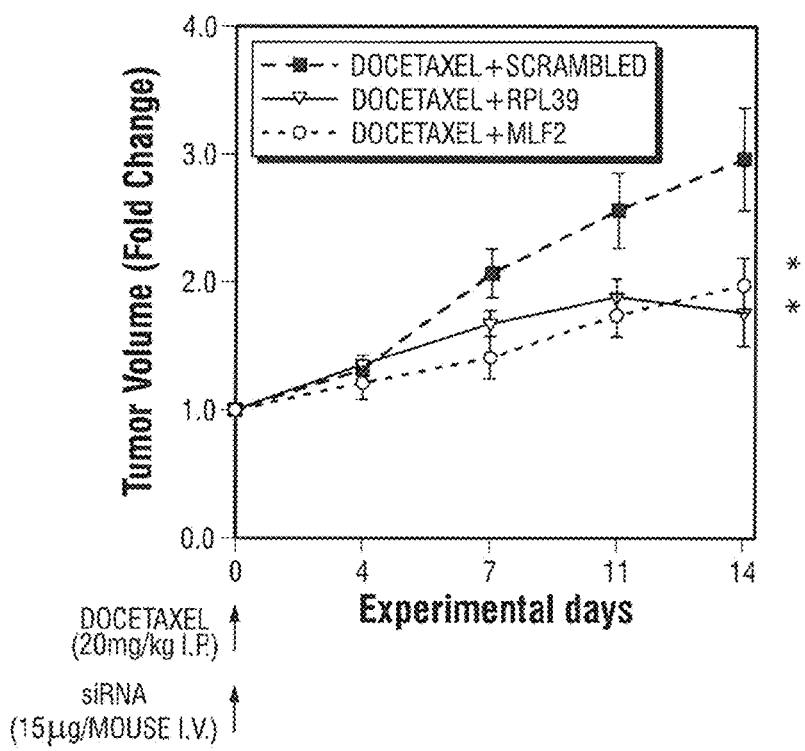
Figure 10C:
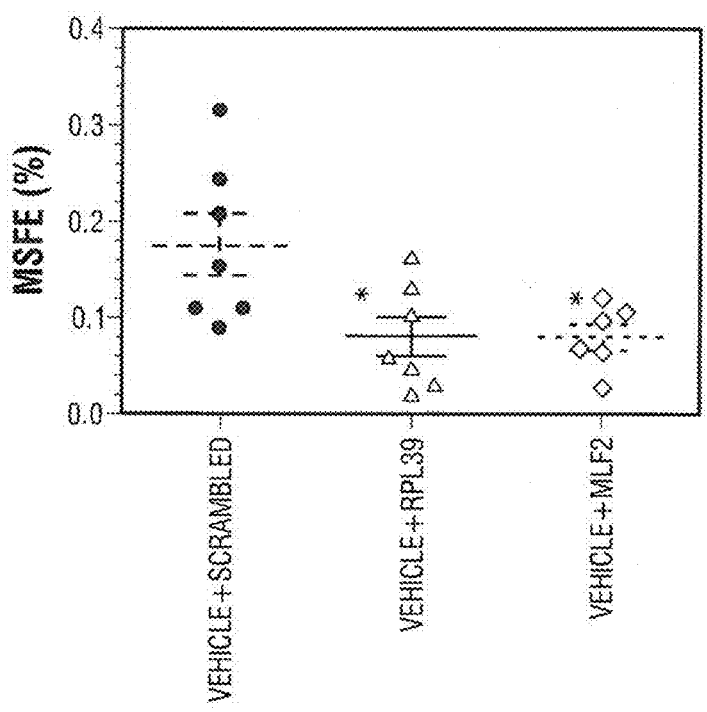
Figure 10D:
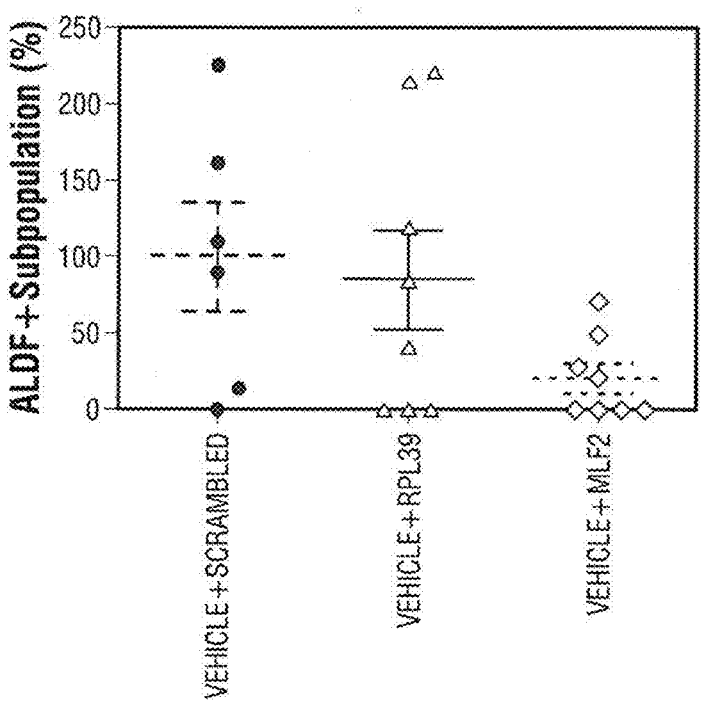

To determine the effect of RPL39 and MLF2 siRNAs on BCSC markers, a series of short-term studies were conducted in two triple negative breast cancer xenograft models: (i) SUM159, (human cancer cell line), and (ii) BCM2665 (patient derived triple negative human cancer in mice model). To improve the efficacy of siRNA delivery, a multistage vector (MSV) nanoparticle delivery platform was utilized, thus allowing for sustained release of siRNA with a single 2-weeks' dose (Tiscotti et al., 2009). Significant reduction in tumor volume was observed for both SUM159 and BCM2665 human-cancer-in-mouse xenograft treated with RPL39 and MLF2 siRNA alone, when compared to vehicle (FIG. 9A and FIG. 10A). Similarly, observations were obtained with the combination of siRNA+chemotherapy vs. standard-dose docetaxel chemotherapy (20 mg/kg) (FIG. 9B and FIG. 10B). With these short-term studies, standard assays were performed for BCSCs. Significant decrease in secondary MSFE with RPL39 and MLF2 siRNAs was observed (FIG. 9C and FIG. 10C). Concomitantly, reduction in Aldefluor® levels was observed in both SUM159 and BCM2665 xenografts. This reduction was not statistically significant due to the variability of expression of the marker (FIG. 9D and FIG. 10D).

Increase in Migration, Proliferation, and MSFE with Overexpression of RPL39 and MLF2.

Figure 11A:
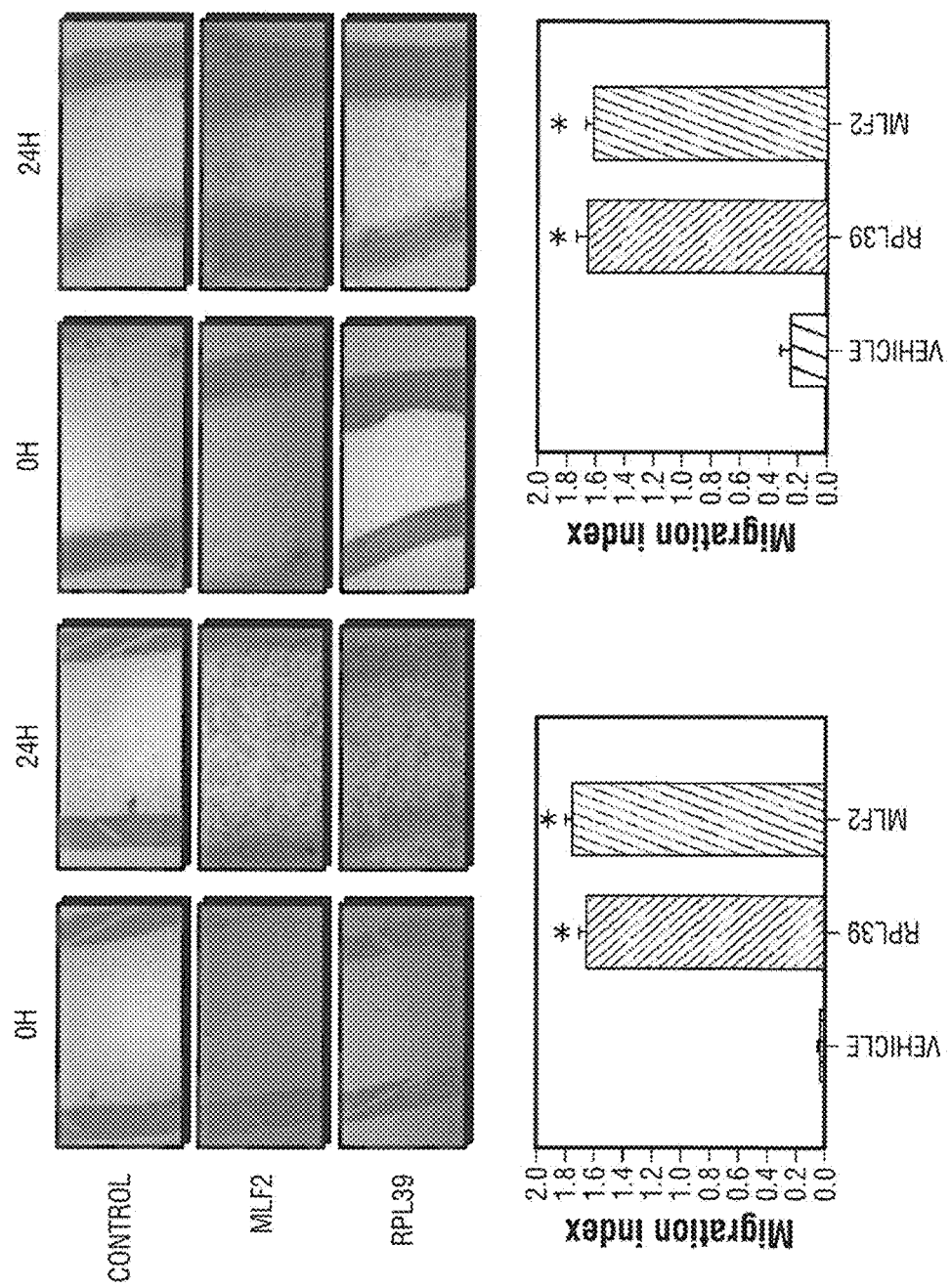

The cell migration properties of cells overexpressing RPL39 and MLF2 were investigated using wound healing assays. Overexpression of RPL39/MLF2 significantly increased the wound healing capacity of these cells. In addition, migration index showed a significant increase in both MDAMB231 and BT549 cells lines on RPL39 and MLF2 overexpression (FIG. 11A). Moreover, overexpression of MLF2 and RPL39 genes under MSFE conditions demonstrated a significant up regulation of MSFE, suggesting an important role for these genes in tumor initiation (FIG. 11B). Additionally, overexpression of RPL39 and MLF2 significantly induced proliferation in all three cell lines tested (FIG. 11C).

RPL39 and MLF2 Overexpression Induces Mesenchymal to Epithelial Transition (MET).

Figure 12A:
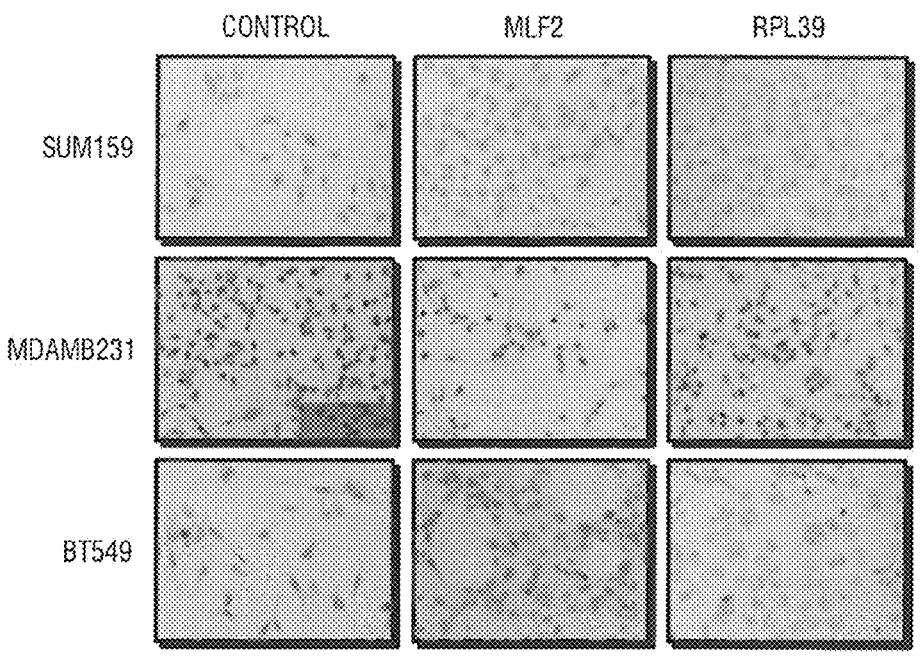
FIG. 12A and FIG. 12B show mesenchymal to epithelial transition with RPL39 and MLF2 genes overexpression.
Figure 12B:
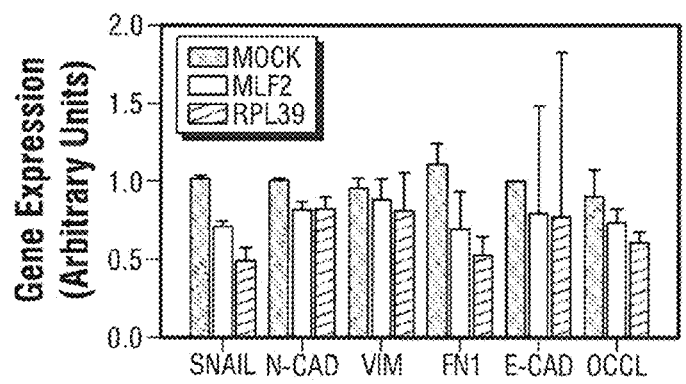
Figure 12B:
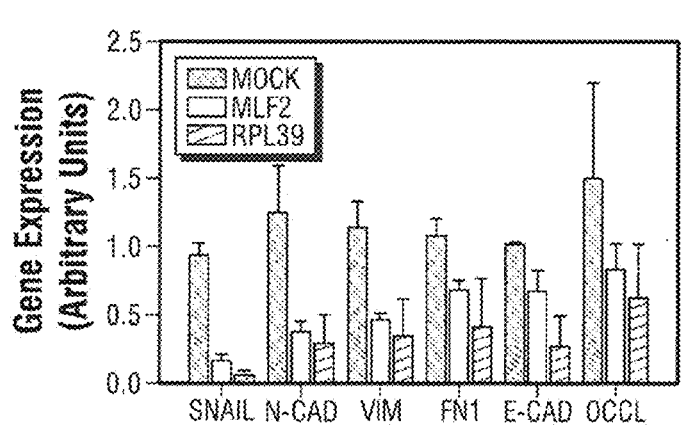

Overexpression of RPL39 and MLF2 in three triple negative cell lines demonstrates a change in morphology of the cells from mesenchymal-like to epithelial-like (FIG. 12A). Additionally, overexpression of these genes in three cell lines significantly reduces gene expression of MET cell lines, SNAIL, N-cadherin, vimentin, fibronectin-1 and occludin as determined by real time quantitative PCR (FIG. 12B).

Characterization of Two Target Genes.

Figure 13A:
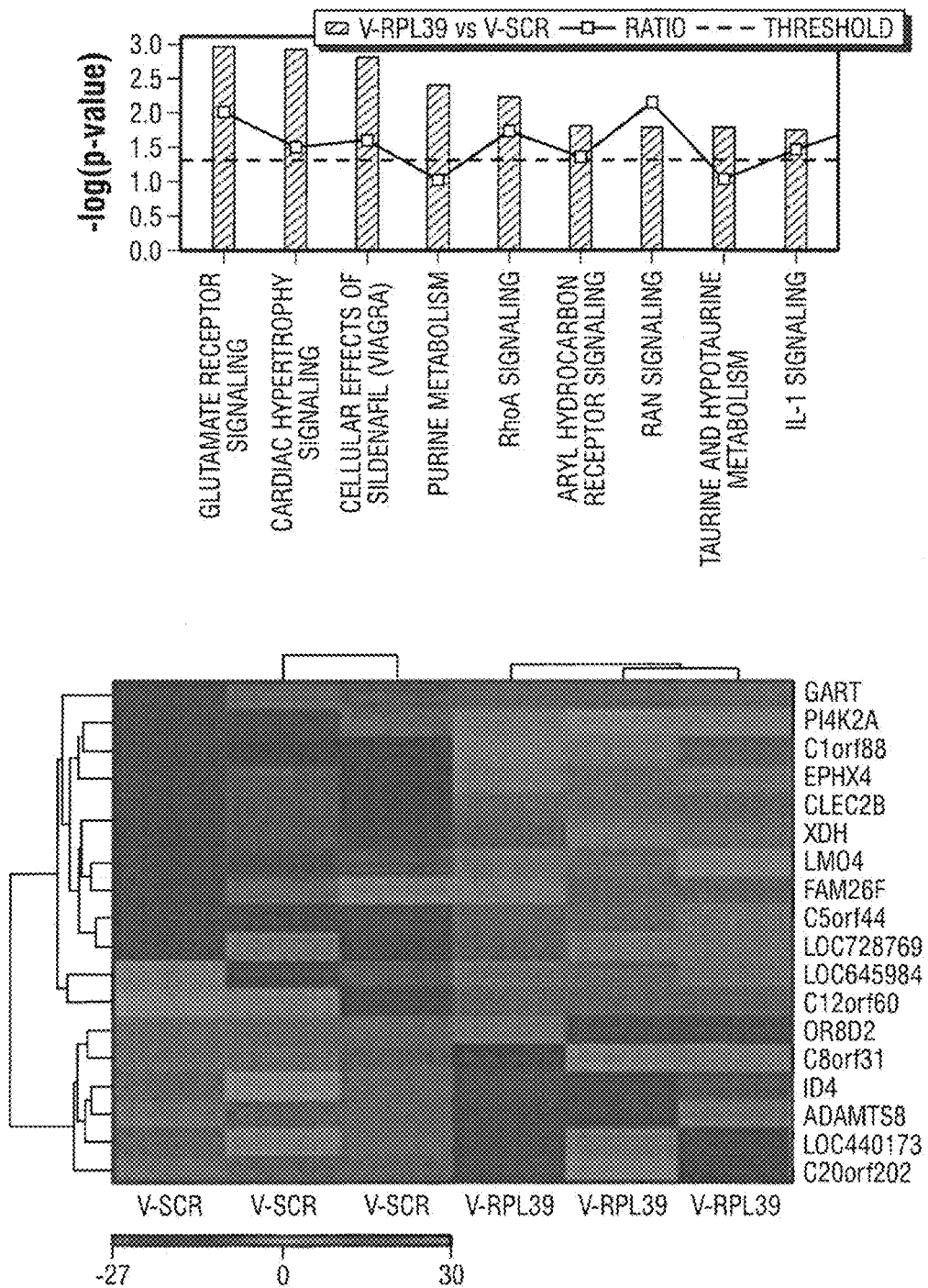
FIG. 13A and FIG. 13B show microarray analysis of a patient-derived human-cancer-in-mice model. BCM2665 treated with RPL39 and MLF2 siRNA. BCM2665 cells were transplanted into fat pad of SCID beige mice. These tumors were randomized into vehicle+scrambled siRNA (15 μg, i.v.), vehicle+RPL39 siRNA (15 μg, i.v.), and vehicle+MLF2 siRNA (15 μg, i.v.). These animal groups were injected intravenously with respective MDS/siRNA on Day 1 and then harvested on Day 14. The tumors were then analyzed by gene expression microarray. A representative picture depicting signaling pathways (IPA) and genes that are up- or down-regulated in RPL39 siRNA (FIG. 13A) as compared to scrambled siRNA is shown.
Figure 13B:
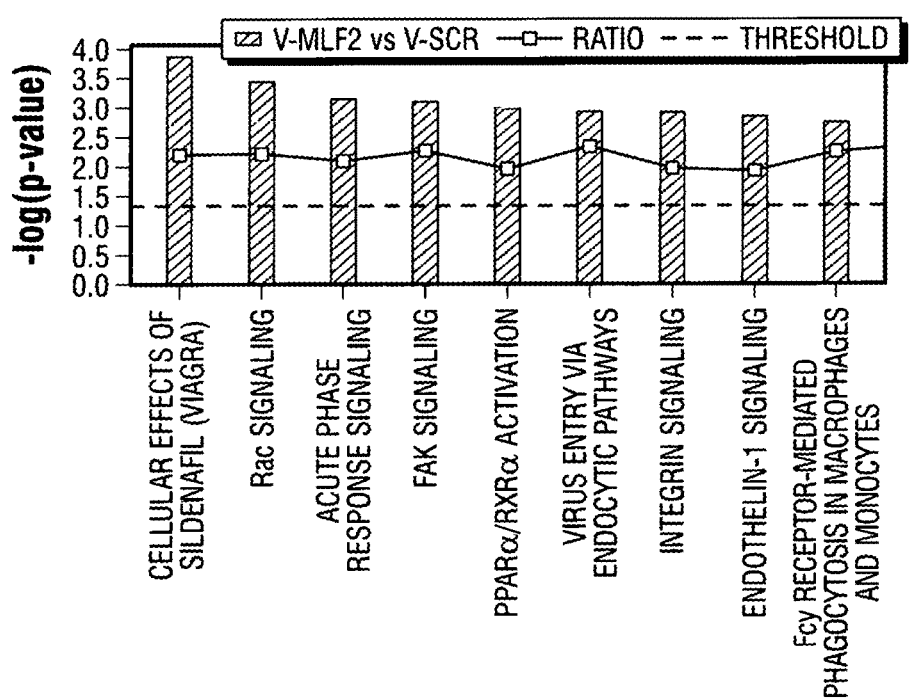
Figure 13:
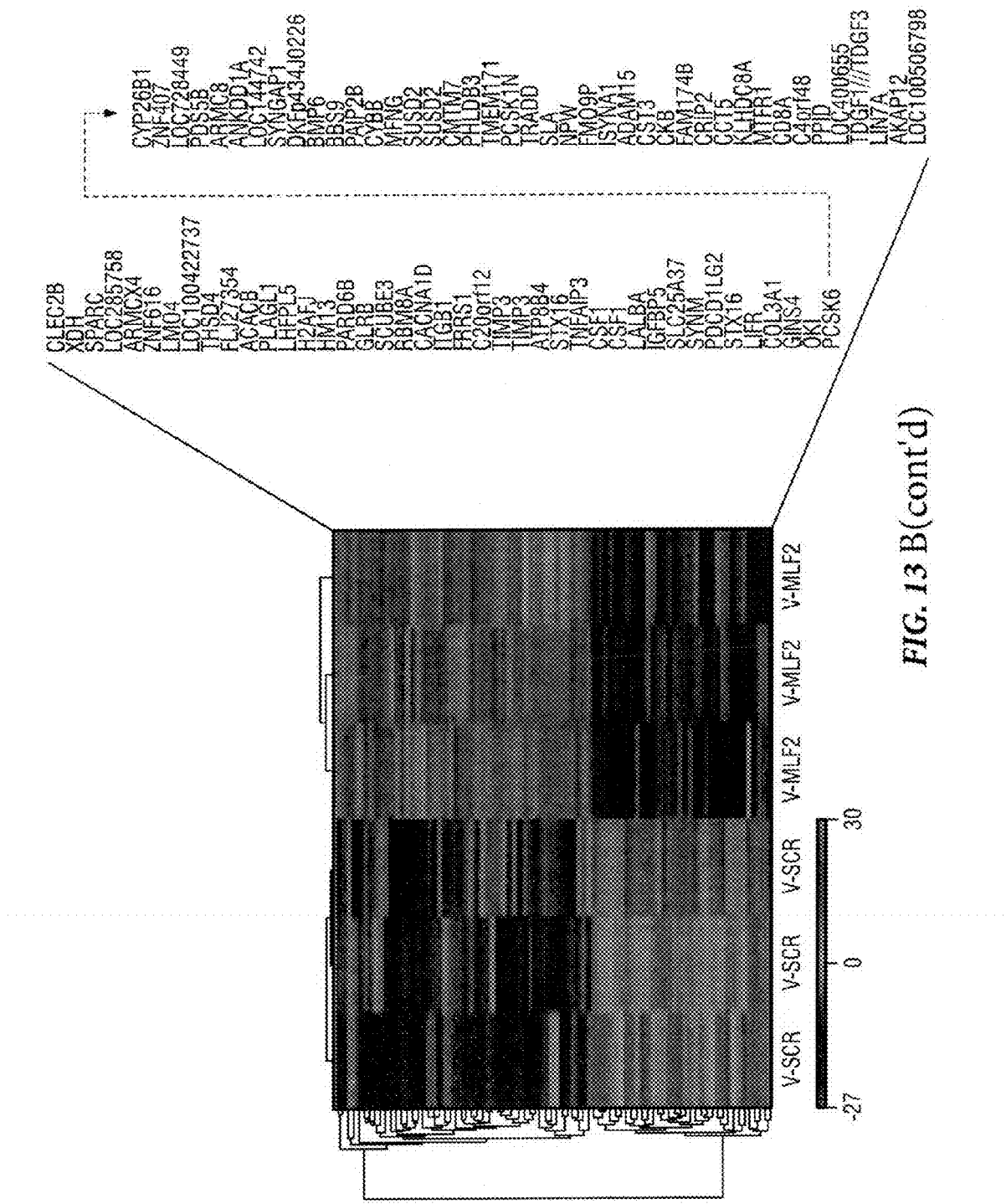

RPL39 and MLF2 are relatively novel cancer-related genes with little described in the literature. To characterize the mechanism of action, siRNA treated human-cancer-in-mice xenograft BCM2665 was analyzed for alterations in gene expression by microarray profiling. Ingenuity Pathway analysis of RPL39- and MLF2-siRNA treated vs. vehicle treated samples was performed. The top signaling pathways in both siRNA-treated samples showed differential expression of "cellular effects of sildenafil (Viagra)", reflecting nitric oxide signaling (NOS) pathway (FIG. 13A and FIG. 13B). In addition, Rac, Rho, and Fak signaling along with purine metabolism were the other important signaling pathways identified by Ingenuity Analysis.

RPL 39 and MLF2 are Regulated Via Nitric Oxide Signaling Pathway.

Figure 14A:
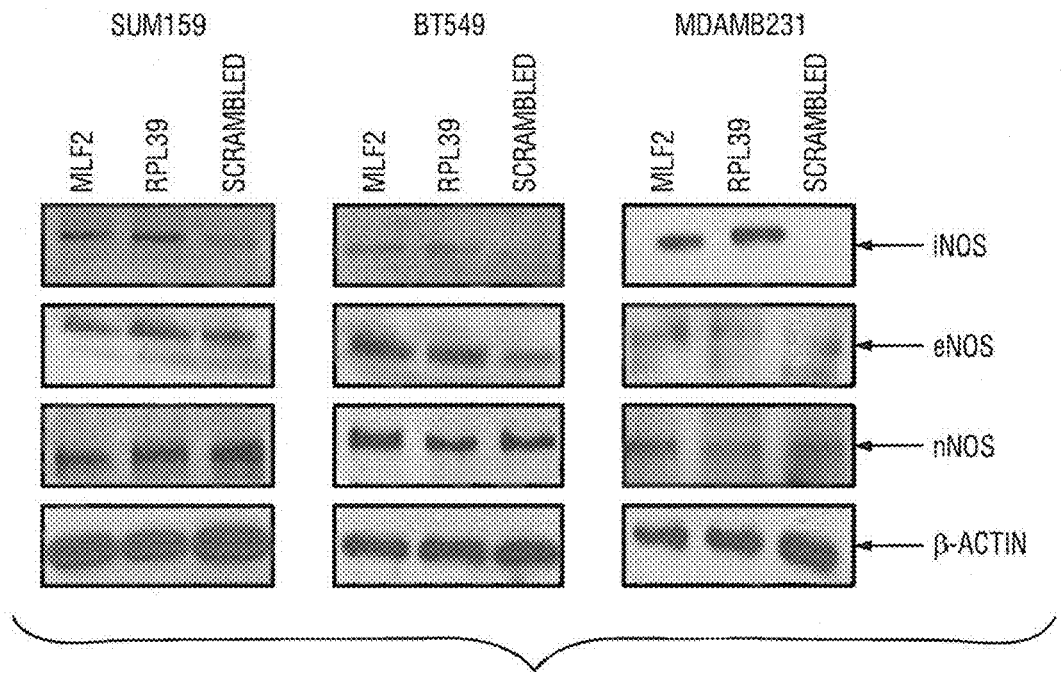
FIG. 14A and FIG. 14B show RPL39 and MLF2 genes are driven by nitric oxide signaling pathway. Downregulation or overexpression of RPL39 and MLF2 (in vitro) demonstrates the engagement of NO (nitric oxide) signaling pathway.
Figure 14B:
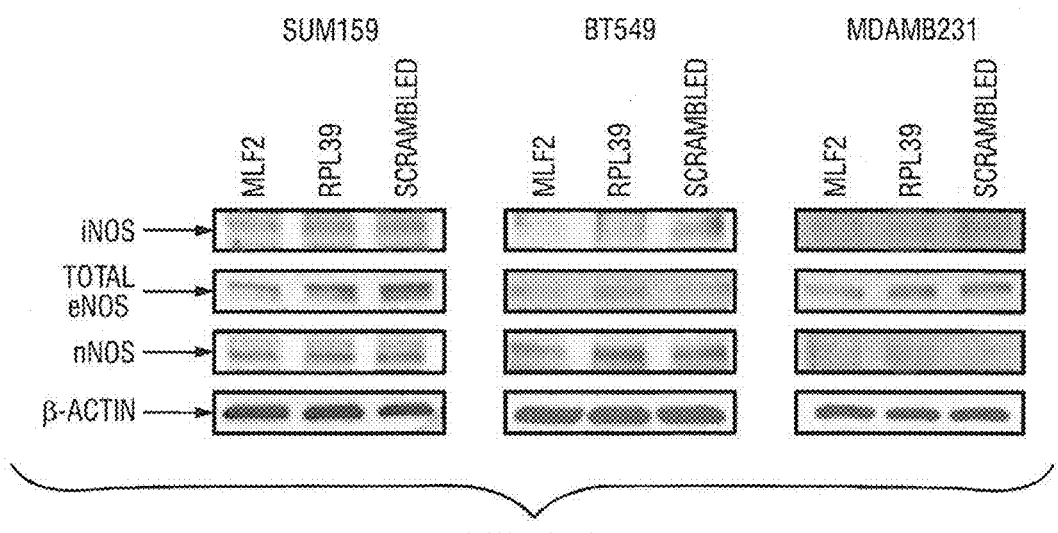

Nitric oxide signaling ["cellular effects of sildenafil (Viagra)"] was the top signaling pathway identified by microarray analysis in both RPl39- and MLF2-siRNA treated in vivo xenograft samples. To confirm this observation, and to characterize the nitric oxide synthase(s) involved, western blot analysis was performed in three triple-negative cell lines treated with in vitro siRNAs (RPL39 and MLF2) and blotted with iNOS, eNOS and nNOS antibodies. The results demonstrated a clear reduction in iNOS signaling, together with a decrease in eNOS, but no changes in nNOS (FIG. 14A). Consistent with earlier observations, overexpression of RPL39 and MLF2 also led to an increase in eNOS and iNOS signaling, but no change in nNOS (FIG. 14B).

Effect of siRNA Against RPL39 and MLF2 on Lung Metastases.

Figure 15A:
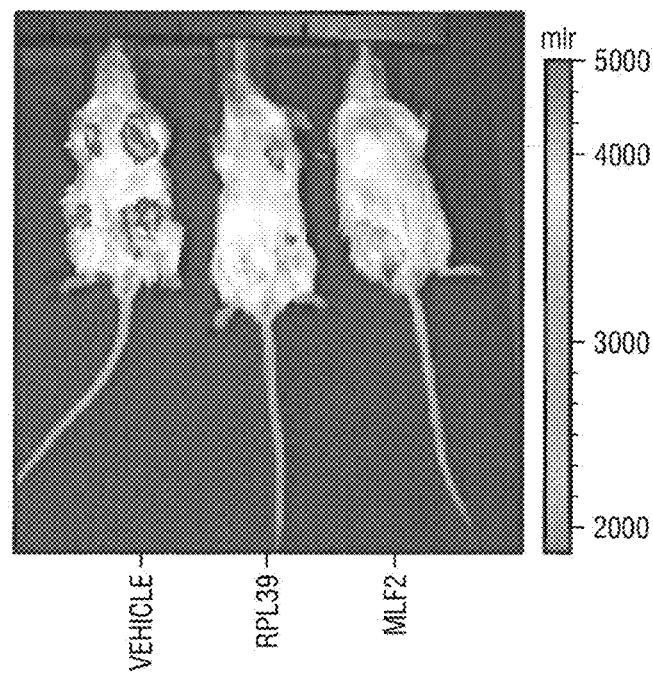
FIG. 15A, FIG. 15B, FIG. 15C, and FIG. 15D show lung metastasis is significantly decreased with RPL39 and MLF2 siRNA, with damaging mutations in lung metastasis for breast cancer patients.
Figure 15B:
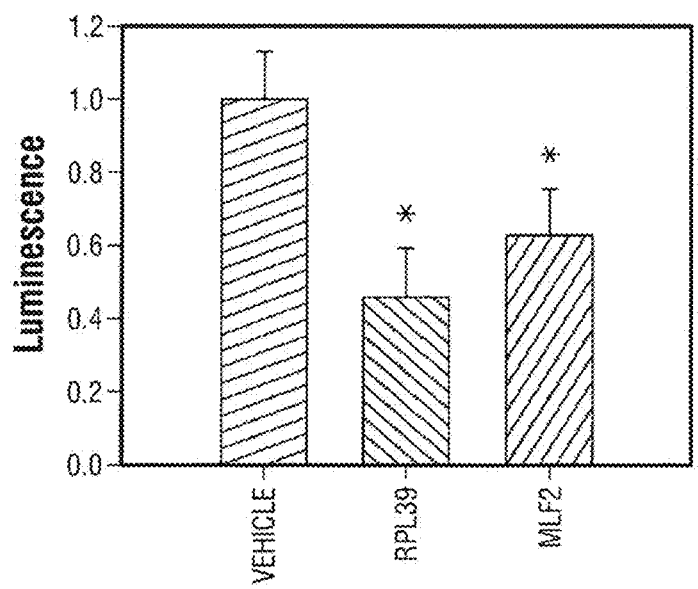

To assess the effects of RPL39 and MLF2 siRNA on lung metastasis, SCID-Beige mice were injected with luciferase-tagged MDAMB231 cells and treated with siRNA against RPL39 or MLF2 packaged in cationic liposomes, twice weekly simultaneously, and then sacrificed at week six. A representative image of RPL39 and MLF2 treated mice six-weeks after primary tumor injection is shown in FIG. 15A. IVIS imaging showed lung metastasis in-vivo in all the animals (12/12) treated with scrambled siRNA, whereas mice treated with RPL39 siRNA (5/11) and MLF2 siRNA (8/12) had significant reduction in lung metastasis $\chi^2$ test, RPL39: $p<0.05$: MLF2: $p<0.05$). Moreover, the luciferase analysis showed a significant reduction in luminescence upon treatment with RPL39 and MLF2 siRNAs respectively ($p<0.05$) (FIG. 15B). Together these results indicated a significant effect of RPL39 and MLF2 on lung metastasis.

Mutations in RPL39 and MLF2 in Human Lung Metastasis of Breast Cancer.

Figure 15C:
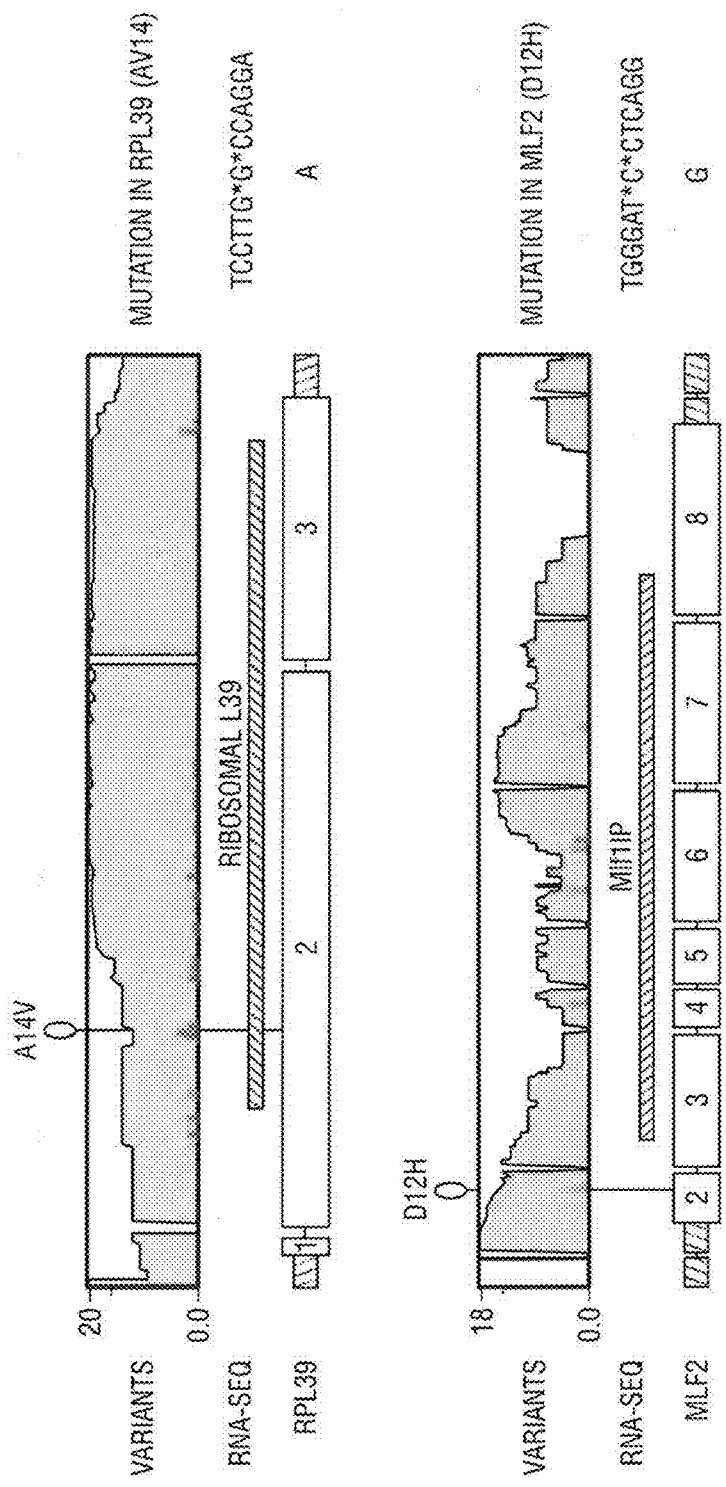
Figure 15D:
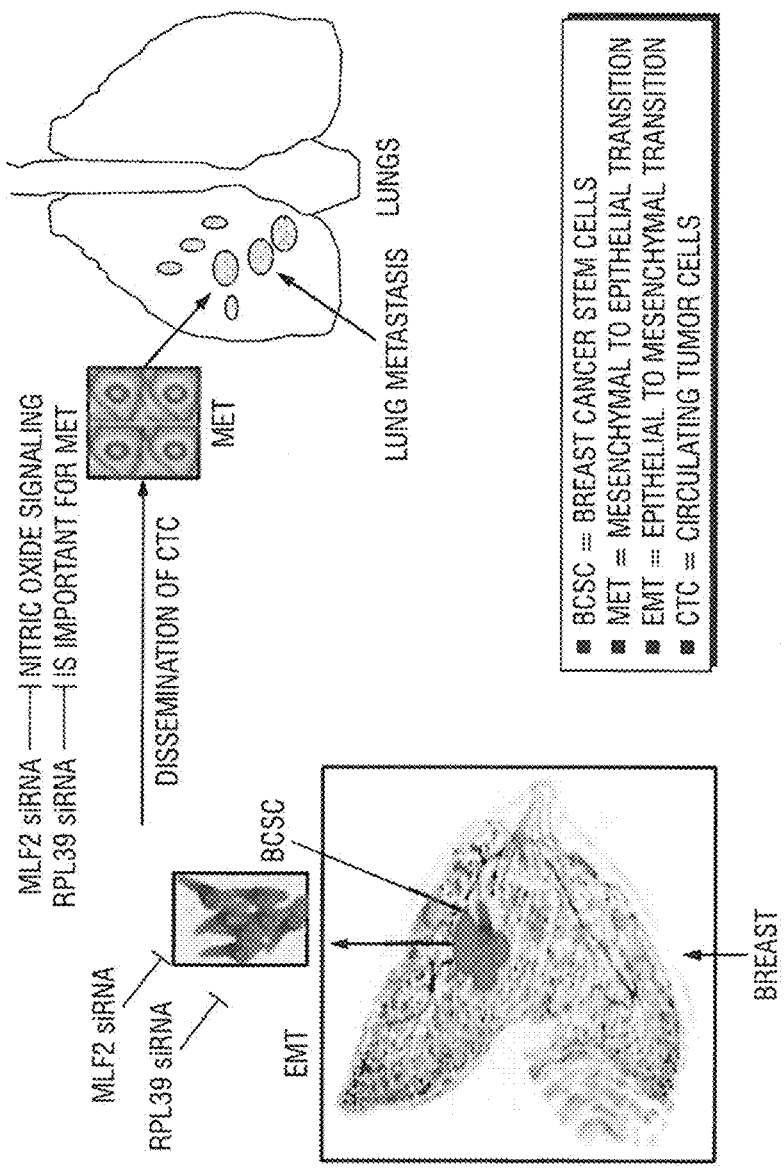

As a profound effect of siRNA against RPL39 and MLF2 were observed in the in vivo lung metastasis model, together with changes consistent with MET with overexpression of both candidate genes, next, lung metastases were analyzed from patients with breast cancer, for possible damaging mutations in RPL39 and MLF2. Eight de-identified samples were obtained from the tumor bank and analyzed for mutations in RPL39 and MLF2 gene using RNA-Seq. Four damaging mutations were determined by SIFT analysis, two each in RPL39 (A14V and G50S) and MLF2 (D12H and R158W). Mutations in MLF2 and RPL39 were then confirmed with competitive allele-specific PCR (A14V mutation in RPL39 and D12H mutation in MLF2) using cDNA prepared from the RNA derived from these human lung metastasis (FIG. 15C). Next, 493 breast cancer exome primary tumors downloaded from the TCGA CGHub were analyzed for mutations in either MLF2 or RPL39. A single sample harbored a silent somatic mutation found within MLF2, but no non-silent, somatic variants were seen in any of the samples for either MLF2 or RPL39.

Discussion

TNBC is characterized by an aggressive phenotype, with high relapse rates, and propensity for metastasis to lung and/or brain (Christiansen et al., 2012: Ray and Polite, 2010). There are no effective targeted therapies in TNBC. Therefore, there is an urgent need to design strategies that will effectively mitigate the chance of relapse and metastasis. In this example, the discovery of two relatively new cancer genes RPL39 and MLF2 is reported, and their importance in self-renewal and metastasis is described.

Recently, functional evidence for the presence of cancer stem cells was confirmed in glioblastomas (GBM), squamous skin tumors, and intestinal adenomas (Chen et al., 2012; Schepers et al., 2012; Driessens et al., 2012). Additionally, in the GBM model, this restricted subpopulation responsible for tumor re-growth was intrinsically resistant to chemotherapy (Chen et al., 2012).

A functional approach has been described herein that was useful in identifying novel targets for cancer stem cells. This screen was performed by shRNA knockdown of previously published gene signature, using high-throughput MSFE assay. To eliminate any false positives, the validity of these targets was reconfirmed using a lower titer of the virus. This stringent screening yielded two potential candidates, namely RPL39 and MLF2. RPL39 has been described as component of the 60S ribosomal complex located on chromosome X (XQ24), with a proposed role in spermatogenesis and translation (Uechi et al., 2002, Nadano et al., 2002). MLF2 is located on chromosome 12, and may participate in chromosomal aberrations and defense response (Kuefer et al., 1996). While very little is known about the role of RPL39 in cancer, there is limited information available on MLF2. A series of amino acid modifications of MLF2 on Ser 144, 152 and 238 (Molina et al., 2007; Nousianien et al., 2006; Daub et al., 2008), and a somatic mutation (p.Phe80Cys) has been described in colorectal cancer (Sjoblom et al., 2006).

A shRNA based high-throughput screening method was utilized for identifying target candidate genes. However, the use of lentivirus in shRNAs makes this approach therapeutically undesirable. Therefore, using the sequences derived from shRNA screening, siRNAs were designed against two of the candidate targets: RPL39 and MLF2. The efficacy of these siRNAs was first confirmed in vitro in three different triple-negative breast cancer cell lines. Then, siRNAs against RPL39/MLF2 packaged in cationic liposomes was tested using MDAMB231, a triple negative cell line with metastatic potential. A significant reduction in tumors treated with siRNAs against RPL39/MLF2 alone was demonstrated, as well as in combination with siRNA/chemotherapy. Additionally, a significant benefit in median survival in the mice treated with combination of chemotherapy and siRNA against RPL39/MLF2 was observed when compared with mice treated with chemotherapy alone. These observations both in vitro and in vivo demonstrate the efficacy of silencing RPL39/MLF2 in primary TNBC.

While the development of treatment strategies that target BCSCs is challenging and important, finding an efficient and reliable delivery system that ensures the treatment agents reach the right location is equally critical. To achieve this goal, multistage particles were utilized where target siRNAs were packaged in neutral liposomes, then loaded onto a nanoporous silicon vehicle. The MSV particle had been previously demonstrated to be eight-times more effective than standard liposomal delivery, known to overcome biological barriers, maximize site-specific localizations and release therapeutics at the target tumor (Tanaka et al., 2009). The other advantage of this delivery system is decrease in tail-vein injections to once every three weeks, thus enabling possible transition into a clinical setting.

These siRNA in MSV particles were effective in reducing cancer stem cells as defined by a reduction in MSFE and flow cytometry in SUM159 xenografts and in patient-derived human cancer-in-mice model system (BCM2665). These results suggest a role for RPL39 and MLF2 as potential targets in cancer. Overexpression of RPL39 and MLF2 in three triple negative cell lines showed increase in cell migration, proliferation and mammosphere formation, suggesting an important function for these two genes in tumor initiation and proliferation. Additionally, overexpression of these two candidate genes resulted in mesenchymal epithelial transition, as demonstrated by classic morphological changes as well as decrease in mesenchymal markers.

Because of the effect of RPL39 and MLF2 siRNA in the in vivo lung metastases model and the observed MET on overexpression of these genes, the inventors next sequenced lung metastases from patients with breast cancer for damaging mutations. Next-generation RNAseq analysis confirmed damaging mutations in RPL39 and MLF2 in 50% of the lung metastases analyzed from breast cancer patients. Interestingly in primary tumors from The Cancer Genome Atlas (TCGA) these mutations were not present, suggesting a specific role of RPL39 and MLF2 as potential metastases genes.

Comprehensive understanding of the mechanisms and functioning of RPL39 and MLF2 is a salient prerequisite for the confirmation of these two novel genes as cancer targets. By analyzing the patient-derived human-cancer-in-mice model BCM2665 tumors treated with RPL39/MLF2 siRNA using microarray analysis, it was observed that the primary pathway for both RPL39 and MLF2 was the nitric oxide signaling ("cellular effects of Sildenafil"). Overexpression of RPL39 and MLF2 followed by western blot analysis confirmed an increase in eNOS and iNOS signaling. Conversely, subsequent siRNA silencing of RPL39 and MLF2 demonstrated a decrease in eNOS and iNOS signaling. These data suggest an important role of nitric oxide (NO) in breast cancer stem cell self-renewal. Multiple studies have investigated the role of NO and cyclic guanosine monophosphate (cGMP) signaling in cancer biology. Paradoxically at higher concentrations NO is cytotoxic, while at a lower concentration NO could facilitate tumor growth (Ignarro et al., 1996; Wink et al., 1996; Grisham et al., 1999). Additionally, the cGMP-dependent (NO/sGC/cGMP pathway) and cGMP-independent (NO oxidative pathway) components may vary among different tissues and cell types (Criss et al., 1976: Kimura et al. 1975; Zhu et al., 2011). A better understanding of the role of NO/sGC/cGMP signaling molecules in tumor tissues and stroma is essential in order to better target NO pathway. Importantly, nitric oxide signaling in other solid cancers like glioblastoma multiforme (GBM) has been shown to play an important role in cancer stem cells through iNOS (Eyeler et al., 2011).

More recently, disruption of MET signaling in GBM stem cells both in vitro and in vive has demonstrated to promote tumor growth and invasiveness (Joo et al., 2012). In addition, hypoxia has been recognized to promote tumor angiogenesis, cancer invasion, therapeutic resistance, and enriches glioblastoma cancer stem cells (GSCs) around the hypoxic necrotic regions of GBM (Li et al., 2009; Jensen, 2009; Heddleston et al., 2009). Hypoxia through HIF1-α has been shown to regulate CD44 and its variants CD44v6, CD44v8, known markers of BCSCs. In addition, restrictive oxygen conditions are known to promote GSC phenotype and markers of self-renewal (McCord et al. 2009. Serda et al., 2009). This information together with recent reports that chronic fetal hypoxia alters iNOS signaling supports a hypoxia-NOS signaling axis (Dong et al., 2011). Changes like low oxygen concentration and increased iNOS signaling alter mesenchymal to epithelial transition, and thus form the basis of survival and promotion of BCSCs. The role of the tumor microenvironment, and reactive oxygen and nitrogen species may play a critical role in metastasis of breast cancer. In conclusion, two genes, RPL39 and MLF2, have been identified that target the breast cancer stem cells and affect lung metastasis. Evidence now suggests that RPL39 and MLF2 functions by altering the nitric oxide signaling pathway.

REFERENCES

The following references, to the extent that they provide exemplary procedural or other details supplementary to those set forth herein, are specifically incorporated herein in their entirety by express reference thereto:

Al-Hajj, M et al. "Therapeutic implications of cancer stem cells," *Curr. Opin. Genet. Dev.,* 14(1):43-47 (2004).

Al-Hajj, M et al., "Prospective identification of tumorigenic breast cancer cells," *Proc. Nat'l. Acad. Sci. USA,* 100(7): 3983-3988 (2003).

Ausubel, F et al. "*Short Protocols in Molecular Biology,* 3rd Ed.," Wiley & Sons, New York, N.Y. (1995).

Campbell, P J et al., "Identification of somatically acquired rearrangements in cancer using genome-wide massively parallel paired-end sequencing," *Nat. Genet.,* 40:722-729 (2008).

Campbell, P J et al., "The patterns and dynamics of genomic instability in metastatic pancreatic cancer," *Nature,* 467: 1109-1113 (2010).

Chaffer, C L et al., "Mesenchymal to epithelial transition in development and disease," *Cells Tissues Organs.* 185:7-19 (2007).

Christiansen, N et al., "Association between African-American race and outcomes in patients with nonmetastatic triple-negative breast cancer: a retrospective analysis by using results from the Georgia cancer specialist database." *Clin. Breast Cancer,* 12:270-275 (2012).

Creighton, C J et al. "Residual breast cancers after conventional therapy display mesenchymal as well as tumor-initiating features," *Proc. Nat'l. Acad. Sci. USA.* 106(33): 13820-13825 (2009).

Decuzzi, P et al. "Size and shape effects in the biodistribution of intravascularly injected particles," *J. Control. Release,* 141(3):320-327 (2009).

DeSantis, C et al. "Disparities in breast cancer prognostic factors by race, insurance status, and education," *Cancer Causes Control,* 21(9): 1445-1450 (2010).

Dong, Y et al. "Chronic fetal hypoxia produces selective brain injury associated with altered nitric oxide synthases," *Am. J. Obstet. Gynecol.,* 204:254-e216-228 (2011).

Dontu, G et al., "Stem cells in normal breast development and breast cancer," *Cell Prolif.,* 36(Suppl 1):59-72 (2003).

Dontu, G et al., "Stem cells in mammary development and carcinogenesis: implications for prevention and treatment," *Stem Cell Rev.,* 1:207-213 (2005).

Dykxhoorn, D M et al. "Killing the messenger: short RNAs that silence gene expression," *Nature Rev.,* 4:457-467 (2003).

Fidler, I J. "The pathogenesis of cancer metastasis: the 'seed and soil' hypothesis revisited,"*Nat. Rev. Cancer,* 3:453-458 (2003).

Fillmore, C M, and Kuperwasser, C, "Human breast cancer cell lines contain stem-like cells that self-renew, give rise to phenotypically diverse progeny and survive chemotherapy," *Breast Cancer Res.* 10:R25 (2008).

Gerlinger, M et al., "Intratumor heterogeneity and branched evolution revealed by multiregion sequencing," *N. Engl. J. Med.,* 366:883-892 (2012).

Giatromanolaki, A et al., "The CD44+/CD24− phenotype relates to 'triple-negative' state and unfavorable prognosis in breast cancer patients," *Med. Oncol.,* 28(3):745-752 (2011).

Grudzien, P et al., "Inhibition of Notch signaling reduces the stem-like population of breast cancer cells and prevents mammosphere formation," *Anticancer Res.,* 30:3853-3867 (2010).

Gupta, G P. and Massague. J. "Cancer metastasis: building a framework," *Cell,* 127:679-695 (2006).

Haffty, B G et al. "Locoregional relapse and distant metastasis in conservatively managed triple negative early-stage breast cancer," *J. Clin. Oncol.,* 24:5652-5657 (2006).

Hale, W G, and Markham, J P, "*The Harper Collins Dictionary of Biology*, Harper Perennial, New York, N.Y., USA (1991).

Hugo, H et al., "Epithelial-mesenchymal and mesenchymal-epithelial transitions in carcinoma progression,", *J. Cell Physiol.* 213:374-383 (2007).

Jugdaohsingh, R et al., "Dietary silicon intake and absorption," *Am. J. Clin. Nutr.,* 75(5):887-893 (2002).

Klopp, A H et al., "Mesenchymal stem cells promote mammosphere formation and decrease E-cadherin in normal and malignant breast cells," *PLoS One,* 5(8):e12180 (2010).

Lapidot, T et al., "A cell initiating human acute myeloid leukaemia after transplantation into SCID mice," *Nature,* 367:645-648 (1994).

Li, X et al. "Intrinsic resistance of tumorigenic breast cancer cells to chemotherapy,", *J. Natl. Cancer Inst.,* 100(9):672-679 (2008).

Liu, R et al., "The prognostic role of a gene signature from tumorigenic breast-cancer cells," *N. Engl. J. Med.* 356 (3):217-226 (2007).

Mani, S A et al., "The epithelial-mesenchymal transition generates cells with properties of stem cells," *Cell,* 133: 704-715 (2008).

Mukherjee, P et al., "Antiangiogenic properties of gold nanoparticles," *Clin. Cancer Res.* 11(9):3530-3534 (2005).

Polyak, K. and Weinberg, R A, "Transitions between epithelial and mesenchymal states: acquisition of malignant and stem cell traits," *Nat. Rev. Cancer,* 9:265-273 (2009).

Rao D D et al., "siRNA vs. shRNA: similarities and differences," *Adv. Drug. Dev. Rev.,* 61(9):746-759 (2009).

Ray, M, and Polite, B N, "Triple-negative breast cancers: a view from 10.000 feet," *Cancer J.,* 16:17-22 (2010).

Resetkova, E et al., "Prognostic impact of ALDH1 in breast cancer: a story of stem cells and tumor microenvironment," *Breast Cancer Res. Treat.,* 123(1):97-108 (2010).

Sambrook, J et al., *Molecular Cloning: A Laboratory Manual,* 3rd Ed., Cold Spring Harbor Press, Cold Spring Harbor, N.Y., USA (2001).

Serda, R E et al., "Mitotic partitioning of silicon microparticles," *Nanoscale,* 2:173-288 (2009).

Serda, R E et al., "The association of silicon microparticles with endothelial cells in drug delivery to the vasculature," *Biomaterials.* 30(13):2440-2448 (2009).

Serda, R E et al. "Quantitative mechanics of endothelial phagocytosis of silicon microparticles," *Cytometry,* 75(9):752-760 (2009).

Scheel, C et al., "Paracrine and autocrine signals induce and maintain mesenchymal and stem cell states in the breast," *Cell,* 145:926-940 (2011).

Shah, N P et al., "Multiple BCR-ABL kinase domain mutations confer polyclonal resistance to the tyrosine kinase inhibitor imatinib (STI571) in chronic phase and blast crisis chronic myeloid leukemia." *Cancer Cell,* 2:117-125 (2002).

Shipitsin, M et al., "Molecular definition of breast tumor heterogeneity," *Cancer Cell,* 11(3):259-273 (2007).

Singh, S K et al., "Identification of a cancer stem cell in human brain tumors," *Cancer Res.,* 63(18):5821-5828 (2003).

Singleton et al., "*Dictionary of Microbiology and Molecular Biology,* 2nd Ed." John Wiley and Sons, New York, N.Y., USA (1994).

Smalley, M, and Ashworth, A, "Stem cells and breast cancer: a field in transit." *Nat. Rev. Cancer,* 3:832-844 (2007).

Stingl, J, and Caldas, C, "Molecular heterogeneity of breast carcinomas and the cancer stem cell hypothesis," *Nat. Rev. Cancer,* 7:791-799 (2007).

Stratford, A L et al., "Targeting tumour-initiating cells to improve the cure rates for triple-negative breast cancer." *Expert Rev. Mol. Med.,* 12:e22 (2010).

Tanaka, T et al., "In vivo evaluation of safety of nanoporous silicon carriers following single and multiple dose intravenous administrations in mice," *Int. J. Pharm.,* 402(1-2):190-197 (2010).

Tanaka, T et al., "Sustained small interfering RNA delivery by mesoporous silicon particles." *Cancer Res.,* 70(9):3687-3696 (2010).

Tiezzi, D G et al., "CD44+/CD24− cells and lymph node metastasis in stage I and II invasive ductal carcinoma of the breast," *Med. Oncol.* 29(3):1479-1485 (2012).

Yu, F et al. "let-7 regulates self-renewal and tumorigenicity of breast cancer cells," *Cell,* 131(6):1109-1123 (2007).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are chemically and/or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A small interfering RNA molecule that comprises:
   (a) a duplex region; and
   (b) either no overhang region or at least one overhang region,
   wherein each overhang region has six or fewer nucleotides,
   wherein the duplex region consists of a sense region and an antisense region that together form the duplex region, and
   wherein the antisense region and the sense region are each 19 to about 30 nucleotides in length, and the antisense region comprises a nucleotide sequence that is greater than 95% identical to the entire sequence of SEQ ID NO: 32.

2. The small interfering RNA molecule of claim 1, wherein the antisense region and the sense region are each 19 to 25 nucleotides in length.

3. The small interfering RNA molecule of claim 1, wherein the molecule comprises at least one overhang region.

4. The small interfering RNA molecule of claim 1, wherein the antisense region comprises a nucleotide sequence that is 100% identical to the entire sequence of SEQ ID NO:32.

5. The small interfering RNA molecule of claim 1, comprised within a pharmaceutical formulation suitable for administration to a mammalian subject.

6. The small interfering RNA molecule of claim 5, wherein the pharmaceutical formulation further comprises a second, distinct small interfering RNA molecule.

7. The small interfering RNA molecule of claim 5, wherein the pharmaceutical formulation further comprises a first anti-cancer agent.

8. A small interfering ribonucleic acid molecule that is either a short hairpin RNA (shRNA) or an siRNA, wherein the shRNA or siRNA comprises an antisense region that is at least 95% identical to entire sequence of SEQ ID NO: 32.

9. A method of inhibiting the expression of HMGXB3 protein in a therapy-resistant human breast cancer tumor initiating cell, comprising contacting said cell with a sufficient amount of the small interfering ribonucleic acid molecule of claim 8 to inhibit the expression of the HMGBX3 protein in the cell.

10. The method of claim 9, further comprising introducing an effective amount of a second, distinct small interfering RNA into the human cell in need thereof.

* * * * *